US007985565B2

(12) United States Patent
Mayer et al.

(10) Patent No.: US 7,985,565 B2
(45) Date of Patent: Jul. 26, 2011

(54) METHOD OF NUCLEIC ACID AMPLIFICATION

(75) Inventors: Pascal Mayer, Geneva (CH); Laurent Farinelli, Vevey (CH); Eric H. Kawashima, Geneva (CH)

(73) Assignee: Illumina, Inc., San Diego, CA (US)

( * ) Notice: Subject to any disclaimer, the term of this patent is extended or adjusted under 35 U.S.C. 154(b) by 452 days.

(21) Appl. No.: 10/449,010

(22) Filed: Jun. 2, 2003

(65) Prior Publication Data
US 2005/0100900 A1    May 12, 2005

Related U.S. Application Data

(63) Continuation of application No. 09/402,277, filed as application No. PCT/GB98/00961 on Apr. 1, 1998, now abandoned.

(30) Foreign Application Priority Data

| Apr. 1, 1997 | (GB) | 9706528.8 |
| Apr. 1, 1997 | (GB) | 9706529.6 |
| Jun. 23, 1997 | (GB) | 9713236.9 |
| Jun. 23, 1997 | (GB) | 9713238.5 |

(51) Int. Cl.
*C12P 19/34* (2006.01)
*C12Q 1/68* (2006.01)
*C12M 1/34* (2006.01)
*C07H 21/02* (2006.01)
*C07H 21/04* (2006.01)

(52) U.S. Cl. ....... 435/91.2; 435/6; 435/91.1; 435/287.1; 435/287.2; 536/23.1; 536/24.3; 536/24.33

(58) Field of Classification Search ............. 435/6, 91.1, 435/91.2, 183, 283.1, 287.1, 287.2; 436/94, 436/501; 536/23.1, 24.3, 24.33, 25.3
See application file for complete search history.

(56) References Cited

U.S. PATENT DOCUMENTS

| 5,302,509 A | | 4/1994 | Cheeseman |
| 5,326,692 A | * | 7/1994 | Brinkley et al. .................. 435/6 |
| 5,405,746 A | | 4/1995 | Uhlen |
| 5,474,796 A | | 12/1995 | Brennan |
| 5,508,169 A | * | 4/1996 | Deugau et al. .................... 435/6 |
| 5,514,539 A | * | 5/1996 | Bukh et al. ......................... 435/5 |
| 5,547,839 A | | 8/1996 | Dower et al. |
| 5,589,332 A | | 12/1996 | Shih et al. |
| 5,616,478 A | | 4/1997 | Chetverin et al. |
| 5,629,158 A | | 5/1997 | Uhlen |
| 5,641,658 A | | 6/1997 | Adams et al. |
| 5,645,801 A | | 7/1997 | Bouma et al. |
| 5,645,994 A | | 7/1997 | Huang |
| 5,683,872 A | | 11/1997 | Rudert et al. |
| 5,690,894 A | | 11/1997 | Pinkel et al. |
| 5,753,439 A | | 5/1998 | Smith et al. |
| 5,795,714 A | * | 8/1998 | Cantor et al. ..................... 435/6 |
| 5,800,992 A | | 9/1998 | Fodor et al. |
| 5,830,663 A | | 11/1998 | Embleton et al. |
| 5,843,660 A | | 12/1998 | Schumm et al. |
| 5,922,574 A | | 7/1999 | Minter |
| 5,939,291 A | | 8/1999 | Loewy et al. |
| 5,976,802 A | | 11/1999 | Ansorge et al. |
| 6,060,288 A | * | 5/2000 | Adams et al. ................. 435/91.2 |
| 6,090,592 A | | 7/2000 | Adams et al. |
| 6,107,023 A | | 8/2000 | Reyes et al. |
| 6,280,949 B1 | | 8/2001 | Lizardi |
| 6,316,229 B1 | | 11/2001 | Lizardi et al. |
| 6,322,971 B1 | | 11/2001 | Chetverin et al. |
| 6,326,489 B1 | | 12/2001 | Church et al. |
| 6,406,893 B1 | | 6/2002 | Knapp et al. |
| 6,432,680 B1 | | 8/2002 | Lin et al. |
| 6,468,751 B1 | | 10/2002 | Adams et al. |
| 6,489,103 B1 | | 12/2002 | Griffiths et al. |
| 6,511,803 B1 | | 1/2003 | Church et al. |
| 7,115,400 B1 | | 10/2006 | Adessi et al. |
| 2005/0100900 A1 | | 5/2005 | Kawashima et al. |

FOREIGN PATENT DOCUMENTS

| DE | 4141178 | 6/1993 |
| EP | 0224126 | 6/1987 |
| EP | 0356021 | 2/1990 |
| EP | 0374665 | 6/1990 |
| EP | 0487104 | 5/1992 |
| EP | 0543484 | 5/1993 |
| EP | 0 665 293 A2 | 8/1995 |
| EP | 0701001 | 3/1996 |
| EP | 0763135 | 3/1997 |
| EP | 1019496 | 7/2000 |
| EP | 1482036 | 12/2004 |

(Continued)

OTHER PUBLICATIONS

Figure 1D from US Patent No. 6,060,288 with the examiner's handwritings.*
Fu et al., Sequencing double-stranded DNA by strand displacement, Nucleic Acids Research, 25:677-679 (1997).
Lockhart et al., Expression monitoring by hybridization to high-density oligonucleotide arrays, Nature Biotechnology, 14:1675-1680 (1996).
Oroskar et al., Detection of immobilized amplicons by ELISA-like techniques, Clinical Chemistry 42:1547-1555 (1996).
Yershov et al., DNA analysis and diagnostics on oligonucleotide microchips, Proc. Natl. Acad. Sci. USA, 93:4913-4918 (1996).
Notomi et al., Loop-mediated isothermal amplification of DNA, Nucleic Acids Research, 28:i-vii (2000).
Lizardi et al., Mutation detection and single-molecule counting using isothermal rolling-circle amplification, Nature Genetics,19:225-232 (1998).

(Continued)

*Primary Examiner* — Frank W Lu
(74) *Attorney, Agent, or Firm* — Tiffany B. Thomas

(57) ABSTRACT

A nucleic acid molecule can be annealed to an appropriate immobilized primer. The primer can then be extended and the molecule and the primer can be separated from one another. The extended primer can then be annealed to another immobilized primer and the other primer can be extended. Both extended primers can then be separated from one another and can be used to provided further extended primers. The process can be repeated to provide amplified, immobilized nucleic acid molecules. These can be used for many different purposes, including sequencing, screening, diagnosis, in situ nucleic acid synthesis, monitoring gene expression, nucleic acid fingerprinting, etc.

8 Claims, 27 Drawing Sheets

FOREIGN PATENT DOCUMENTS

| | | |
|---|---|---|
| GB | 2233654 | 1/1991 |
| WO | WO 87/06270 | 10/1987 |
| WO | WO 88/10315 | 12/1988 |
| WO | WO 89/01050 | 2/1989 |
| WO | WO 89/09282 | 10/1989 |
| WO | WO 90/02205 | 3/1990 |
| WO | WO 90/06042 | 6/1990 |
| WO | WO 90/09455 | 8/1990 |
| WO | WO 90/11369 | 10/1990 |
| WO | WO 91/06678 | 5/1991 |
| WO | WO 92/04469 | 3/1992 |
| WO | WO 92/10587 | 6/1992 |
| WO | WO 93/03151 | 2/1993 |
| WO | WO 93/04199 | 3/1993 |
| WO | WO 93/09250 | 5/1993 |
| WO | WO 93/21340 | 10/1993 |
| WO | WO 94/02634 | 2/1994 |
| WO | WO 94/05414 | 3/1994 |
| WO | WO 94/24312 | 10/1994 |
| WO | WO 95/12416 | 5/1995 |
| WO | WO 95/33073 | 12/1995 |
| WO | WO 96/04404 | 2/1996 |
| WO | WO 96/24688 | 8/1996 |
| WO | WO 96/27025 | 9/1996 |
| WO | WO 96/32504 | 10/1996 |
| WO | WO 96/34114 | 10/1996 |
| WO | WO 96/36737 | 11/1996 |
| WO | WO 97/19193 | 5/1997 |
| WO | WO 97/41256 | 11/1997 |
| WO | WO 97/45554 | 12/1997 |
| WO | WO 98/36094 | 8/1998 |
| WO | WO 98/44151 | 10/1998 |
| WO | WO 98/44152 | 10/1998 |
| WO | WO 98/45474 | 10/1998 |
| WO | WO 00/41524 | 7/2000 |
| WO | WO 00/75374 | 12/2000 |

OTHER PUBLICATIONS

Westin et al., Anchored multiplex amplification on a microelectronic chip array, Nature Biotechnology, 18:199-204 (2000).
Walker et al., Multiplex strand displacement amplification (SDA) and detection of DNA sequences from *Mycobacterium tuberculosis* and other mycobacteria, Nucleic Acids Research, 22:2670-2677 (1994).
Walker et al., Isothermal in vitro amplification of DNA by a restriction enzyme/DNA polymerase system, Proc. Natl. Acad. Sci., 89:392-396 (1992).
Walker, Empirical aspects of strand displacement amplification, PCR Methods Appl., 3:1-6 (1993).
Saunders et al., PCR amplification of DNA microdissected from a single polytene chromosome band: a comparison with conventional microcloning, Nucleic Acids Research, 17:9027-9037 (1989).
Ochman et al., Genetic Applications of an Inverse Polymerase Chain Reaction, Genetics, 120:621-623 (1988).
Steigerwald et al., Ligation-mediated PCR improves the sensitivity of methylation analysis by restriction enzymes and detection of specific DNA strand breaks, Nucleic Acids Research, 18:1435-1439 (1990).
Triglia et al., A procedure for in vitro amplification of DNA segments that lie outside the boundaries of known sequences, Nucleic Acids Research, 16:8186 (1988).
Ludecke et al., Cloning defined regions of the human genome by microdissection of banded chromosomes and enzymatic amplification, Nature, 338:348-350 (1989).
Sterky et al. Direct sequencing of bacterial artificial chrmomosomes (BACs) and prokaryotic genomes by biotin-capture PCR. Journal of Biotechnology 60:119-129 (1998).
Thomas et al. Affymetrix: genes on chips. Exp. Opin. Ther. Patents 8(5):503-8 (1998).
VanNess et al. A versatile solid support system for oligodeoxynucleotide probe-based hybridization assays. Nucleic Acids Research 19(12):3345-3350 (1991).
Vos et al. AFLP: a new technique for DNA fingerprinting. Nucleic Acids Research 23:4407-4414 (1995).

Winn-Deen et al. Non-radioactive detection of *Mycobacterium tuberculosis* LCR products in a microtitre plate format. Mol. Cell. Probes 7:179-186 (1993).
Wolf et al. Rapid hybridization kinetics of DNA attached to submicron latex particles. Nucleic Acids Research 15:2911-2926 (1987).
Yang et al., Covalent immobilization of oligonucleotides on modified glass/silicon surfaces for solid-phase DNA hybridization and amplification. Chemistry Letters 27:257-8 (1998).
Saiki et al. Genetic analysis of amplified DNA with immobilized sequence-specific oligonucleotide probes. Proc. Natl. Acad. Sci. 86:6230-6234 (1989).
Stamm et al. Sanchored PCR: PCR with cDNA coupled to a solid phase. Nucleic Acids Research 19(6):1350(1991).
Cheng et al., "Chip PCR. II, Investigation of different PCR amplification systems in microfabricated silicon-glass chips", Nucleic Acids Research 24:380-385, 1996.
Chirsey et al., "Covalent attachment of synthetic DNA to self-assembled monolayer films", Nucleic Acids Research 24 (15):3031-3039,1996.
Hahn et al., "Quantitative polymerase chain reaction with enzyme-linked immunosorbent assay detection of selectively digested amplified sample and control DNA" Anal. Biochem. 229:236-248, 1995.
Lamture et al., "Direct detection of nucleic acid hybridization on the surface of a charge coupled-device", Nucleic Acids Research 22(11):2121-2125, 1994.
Maskos et al., "Oligonucleotide hybridizations on glass supports: A novel linker for oligonucleotide synthesis and hybridization properties of oligonucleotides synthesized in situ", Nucleic Acids Research 20(7):1679-1684, 1992.
Oroskar et al., "Detection of immobilized amplicons by ELISA-like techniques" Clinical Chemistry 42(9):1547-1555, 1996.
Pease et al., "Light-generated oligonucleotides arrays for rapid DNA sequence analysis" Proc Natl. Acad. Sci. 91:5022-5026, 1994.
Pirrung et al., "Comparison of methods for photochemical phosphoramidite-based DNA synthesis", Journal of Organic Chemistry 60(20):6270-6276, 1995.
Abel et al. Fiber-optic evanescent wave biosensor for the detection of oligonucleotides. Anal. Chem. 68:2905-2912 (1996).
Babic et al. MutS interaction with mismatch and alkylated base containing DNA molecules detected by optical biosensor. Mutation Research 372:87-96 (1996).
Beattie et al. Hybridization of DNA targets to glass-tethered oligonucleotide probes. Molecular Biotechnology 4:213-225 (1995).
Blanchard et al., Oligonucleotide array synthesis using ink jets. Genome Science and Technology 1(3):225 (1996).
Bronk et al. Combined imaging and chemical sensing using a single optical imaging fiber. Anal. Chem. 67:2750-2757 (1995).
Chee et al. Accessing genetic information with high-density DNA arrays. Science 274(5287):610-614 (2001).
Chu et al. Derivatization of unprotected polynucleotides. Nucleic Acids Research 11(18):6513-6529 (1983).
Drmanac et al. Sequencing by hybridization: towards an automated sequencing of one million m13 clones arrayed on membranes. Electrophoresis 13:566-573 (1992).
Egan et al. Structural studies and chemistry of bacterial capsular polysaccharides. Investigations of phosphodiester-linked capsular polysaccharides isolated from *Haemophilus influenza* types a, b, c and f: NMR spectroscopic identification and chemical modification of end groups and the nature of base-catalyzed hydrolytic depolymerization. J. Am. Chem. Soc. 104:2898-2910 (1982).
Eggleston et al. A helicase assay based on the displacement of fluorescent, nucleic acid-binding ligands. Nucleic Acids Research 24(7):1179-1186 (1996).
Ferguson et al. A fiber-optic DNA biosensor microarray for the analysis of gene expression. Nature Biotechnology 14:1681-1684 (1996).
Fodor et al. Light-directed, spatially addressable parallel chemical synthesis. Science 251:767-773 (1991).
Ghosh et al. Covalent attachment of oligonucleotides to solid supports. Nucleic Acids Research 15:5353-5371 (1987).
Gilham, The synthesis of celluloses containing covalently bound nucleotides, polynucleotides and nucleic acids. Biochemistry 7(8):2809-2813 (1968).

Gingeras et al. Hybridization properties of immobilized nucleic acids. Nucleic Acids Research 15:5373-5390 (1987).

Guo et al. Direct fluorescence analysis of genetic polymorphisms by hybridization with oligonucleotide arrays on glass supports. Nucleic Acids Research 22(24):5456-5465 (1994).

Higuchi et al. Kinetic PCR analysis: real-time monitoring of DNA amplification reactions. Bio/Technology 11:1026-1030 (1993).

Joos et al. Covalent attachment of hybridizable oligonucleotides to glass supports. Analytical Biochemistry 247:96-101 (1997).

Kaneoka et al. Solid-phase direct DNA sequencing of allele-specific polymerase chain reaction-amplified HLA-DR genes. Biotechniques 10(1):30, 32, 34 (1991).

Kremsky et al. Immobilization of DNA via oligonucleotides containing an aldehyde or carboxylic acid group at the 5' terminus. Nucleic Acids Research 15(7):2891-2909 (1987).

Kulp et al. Polymer immobilized enzyme optrodes for the detection of penicillin. Anal. Chem. 59:2849-2853 (1987).

Lambert et al. cDNA library construction from small amounts of RNA using paramagnetic beads and PCR. Nucleic Acids Research 21(3):775-6 (1993).

Lund et al. Assessment of methods for covalent binding of nucleic acids to magnetic beads, Dynabeads™ and the characteristics of the bound nucleic acids in hybridization reactions. Nucleic Acids Research 16:10860-10881 (1988).

Manley et al. DNA-dependent transcription of adenovirus genes in a soluble whole-cell extract. PNAS 77 (7):3855-3859 (1980).

Maskos et al. Parallel analysis of oligodeoxyribonucleotide (oligonucleotide) interactions. I. Analysis of factors influencing oligonucleotide duplex formation. Nucleic Acids Research 20(7):1675-1678 (1992).

Munkholm et al. Polymer modification of fiber optic chemical sensors as a method of enhancing fluorescence signal for pH measurement. Anal. Chem. 58:1427-1430 (1986u.

O'Donnell-Maloney et al. The development of microfabricated arrays for DNA sequencing and analysis. Trends in Biotechnology 14:401-7 (1996).

Peeters et al. Comparison of four bi-functional reagents for coupling peptides to proteins and the effect of the three moieties on the immunogenicity of the conjugates. Journal of Immunological Methods 120:133-143 (1989).

Piunno et al., Fiber-optic DNA sensor for fluorometric nucleic acid determination. Anal. Chem. 67:2635-2643 (1995).

Rasmussen et al. Covalent immobilization of DNA onto polystyrene microwells: The molecules are only bound at the 5' end. Analytical Biochemistry 198:138-142 (1991).

Saiki et al. Enzymatic amplification of β-globin genomic sequences and restriction site analysis for diagnosis of sickle cell anemia. Science 230:1350-1354 (1985).

* cited by examiner

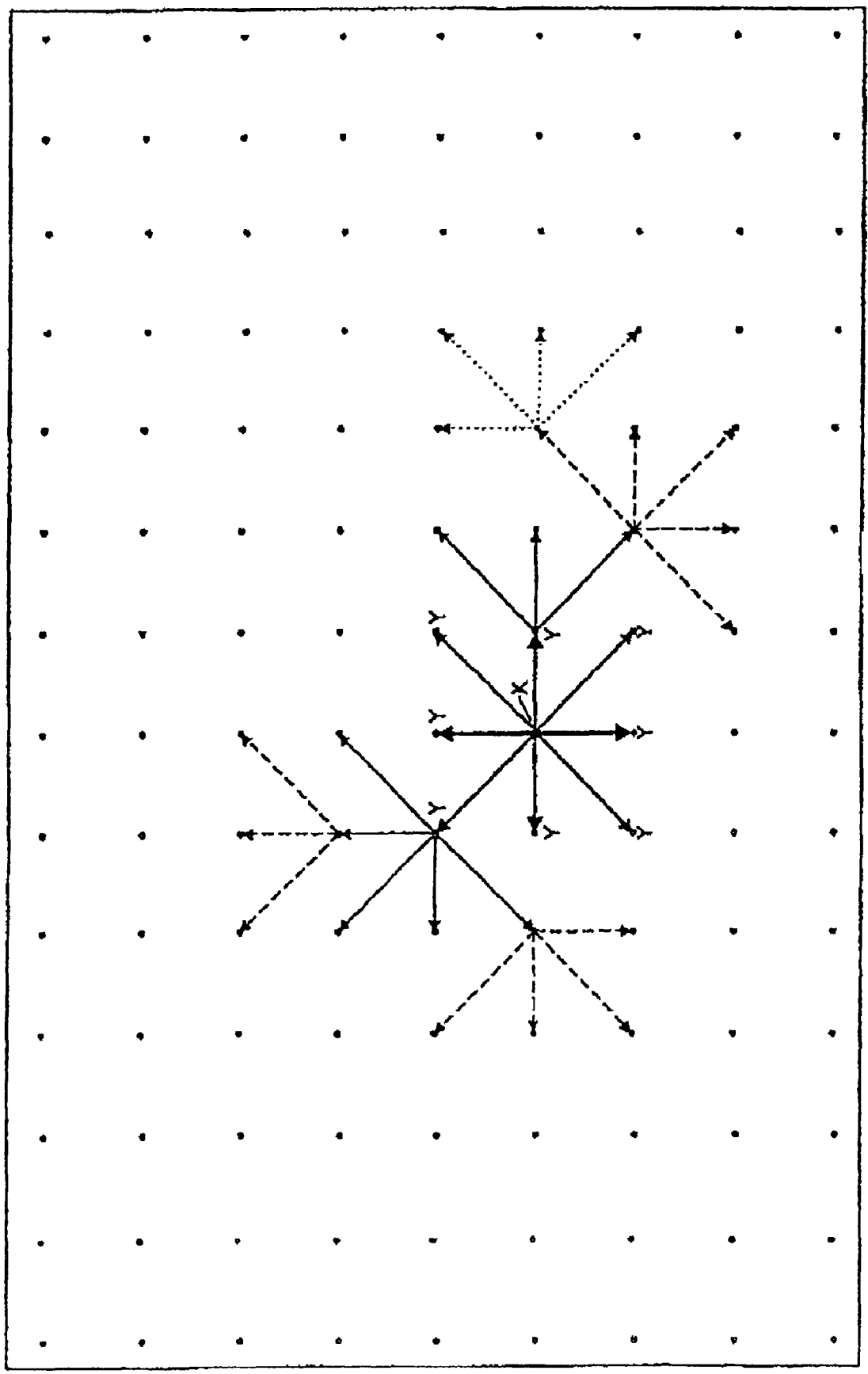
FIG. 2 SHOWS SCHEMATIC VIEW OF COLONY GROWTH

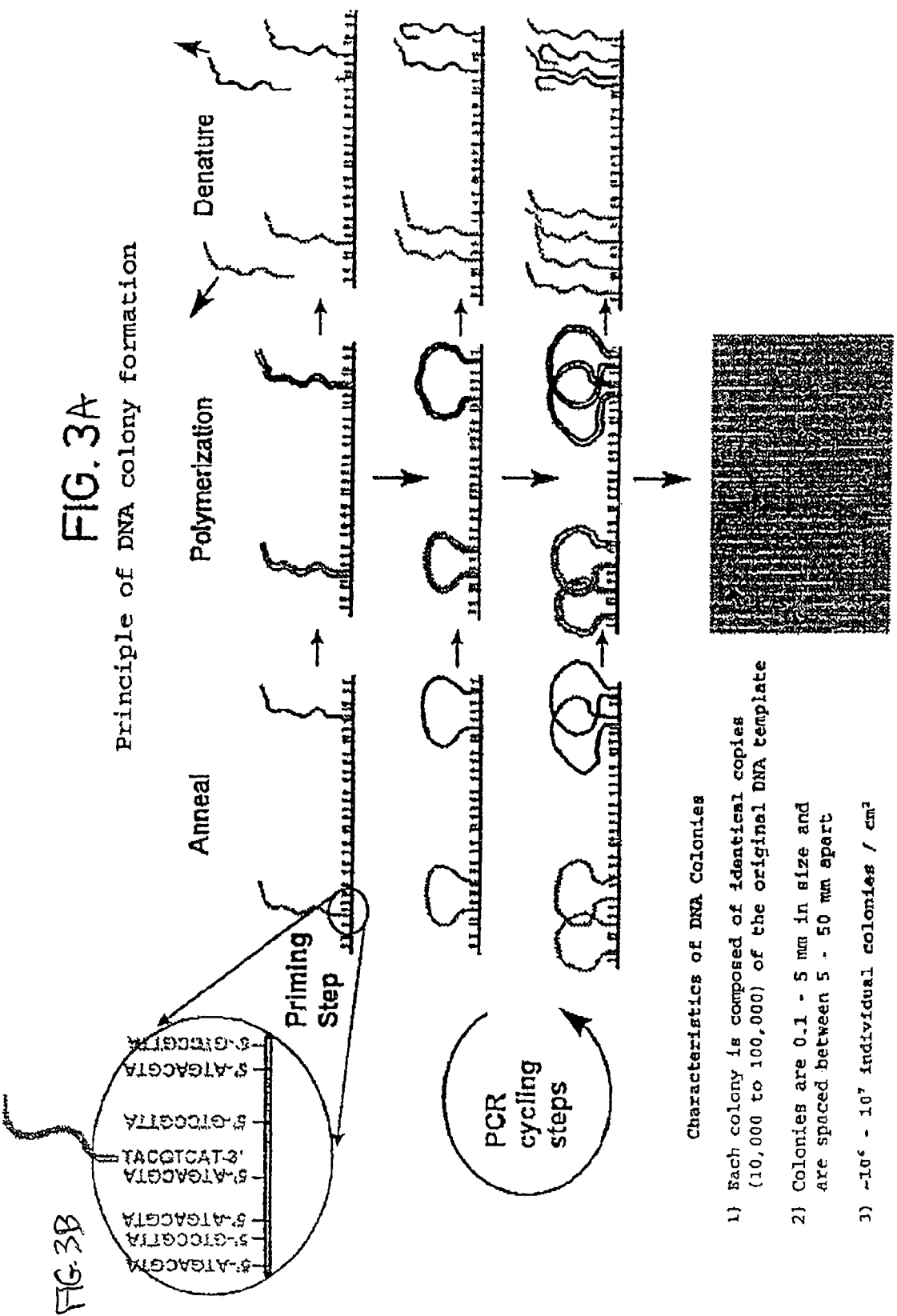

FIG. 7
ii) with template
FIG. 8
DNA amplification: detection of colonies by specific probe hybridisation
i) S1/S2 template ratio = 1/0
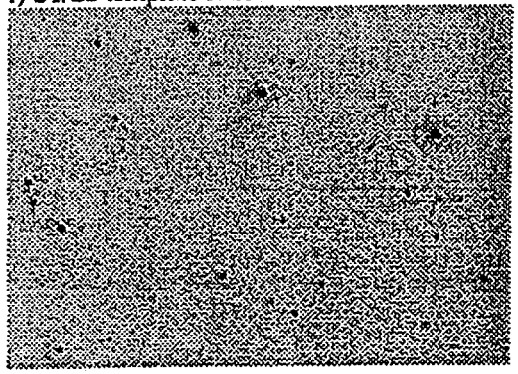
ii) S1/S2 template ration = 1/10
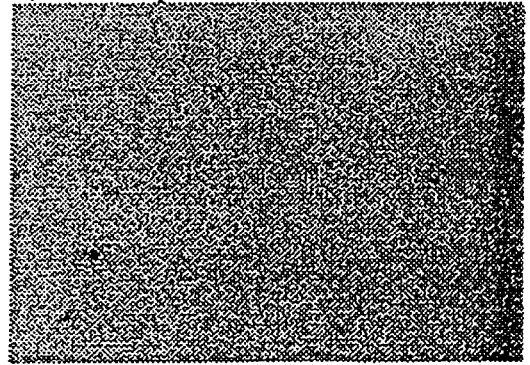
iii) S1/S2 template ratio = 0/1
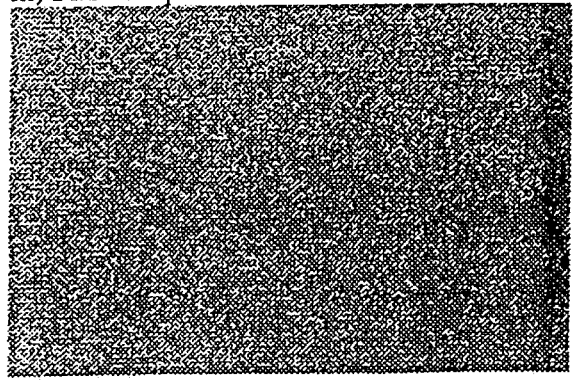

FIG. 10A
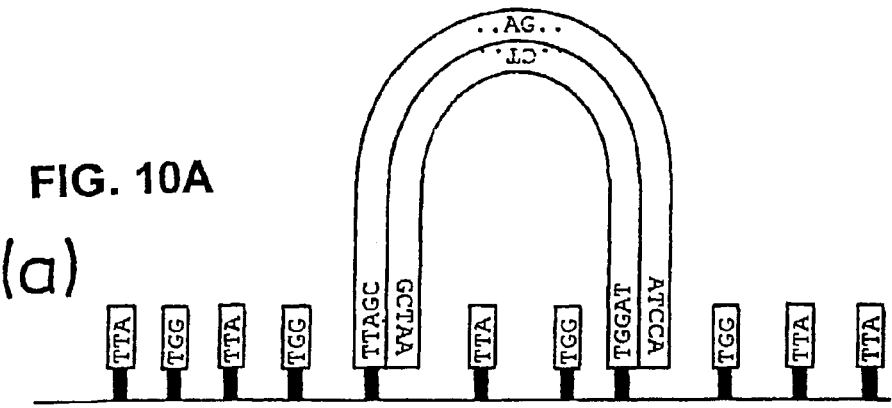
(a)
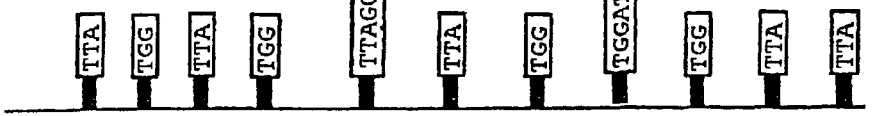
(b)
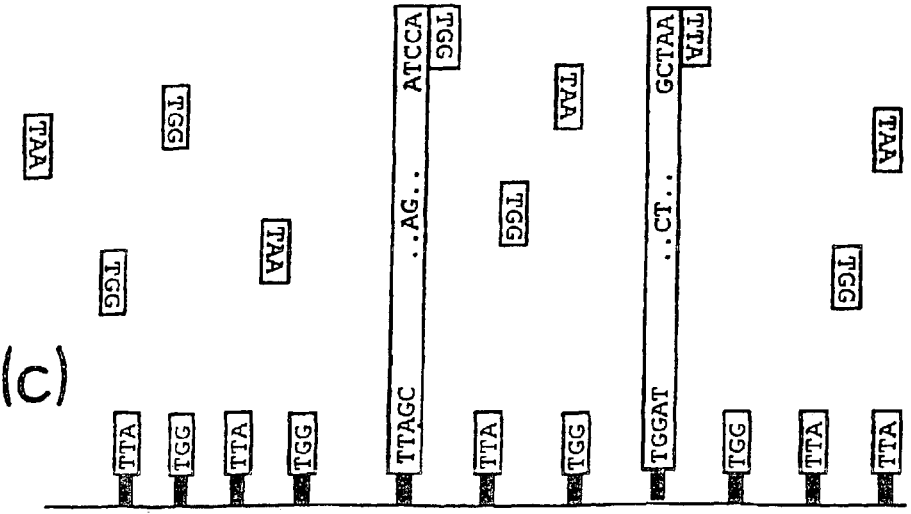
(c)

(iii) ↓
FIG. 10B
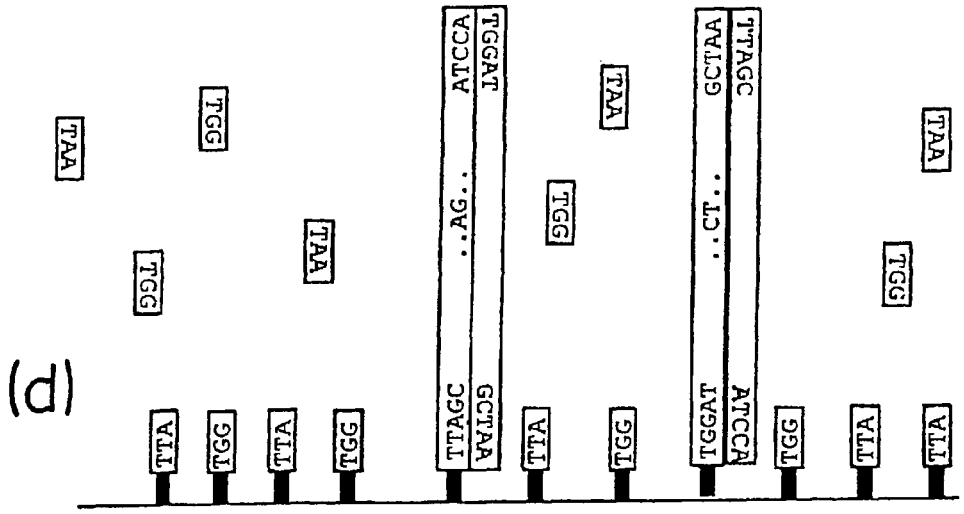
(d)
(iv) ↓
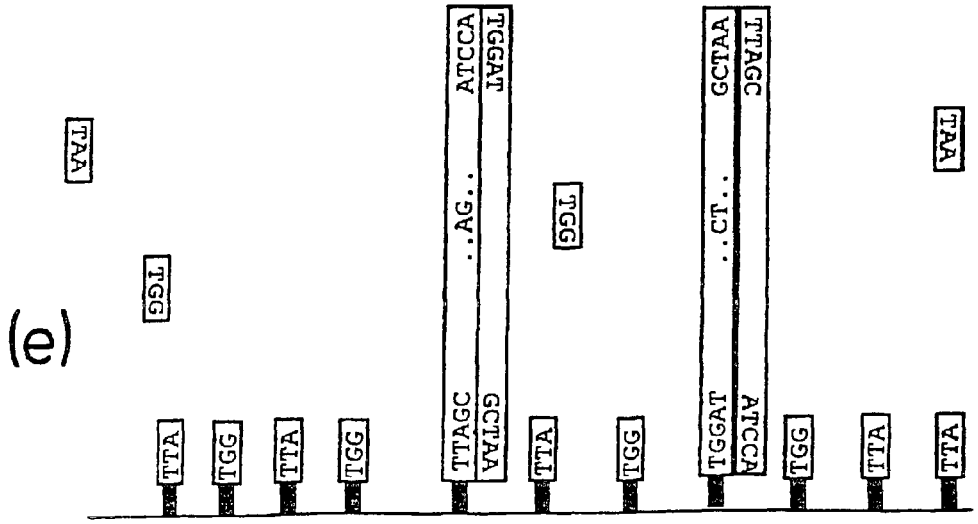
(e)

FIG. 11
A)
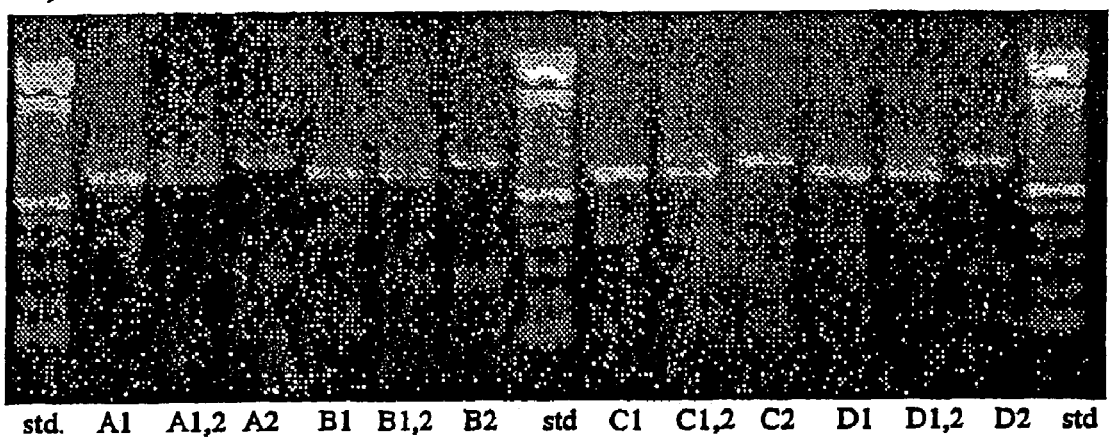
std.  A1  A1,2  A2  B1  B1,2  B2  std  C1  C1,2  C2  D1  D1,2  D2  std
B)
std.  E1  E1,2  E2  F1  F1,2  F2  std

FIG. 12A
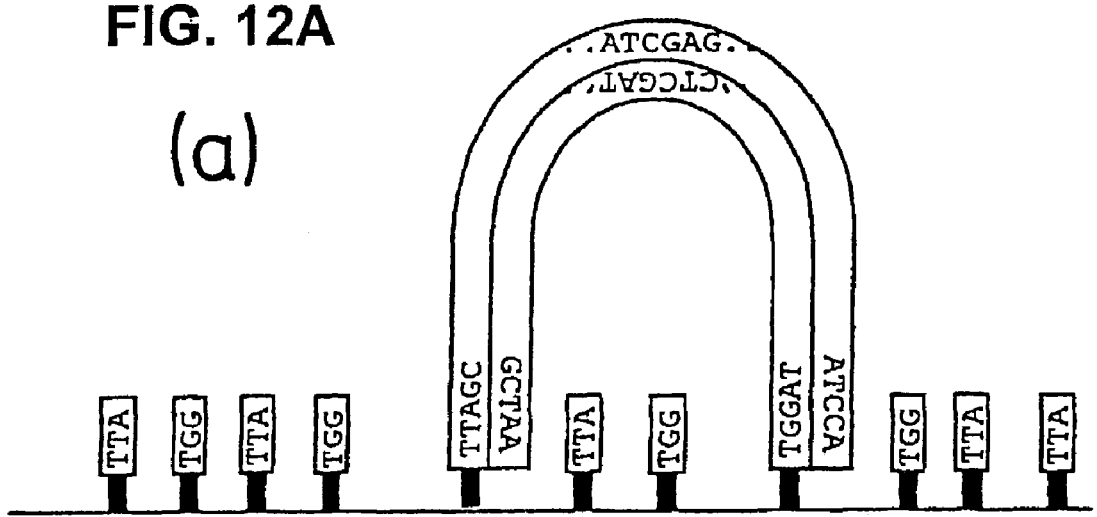
(a)
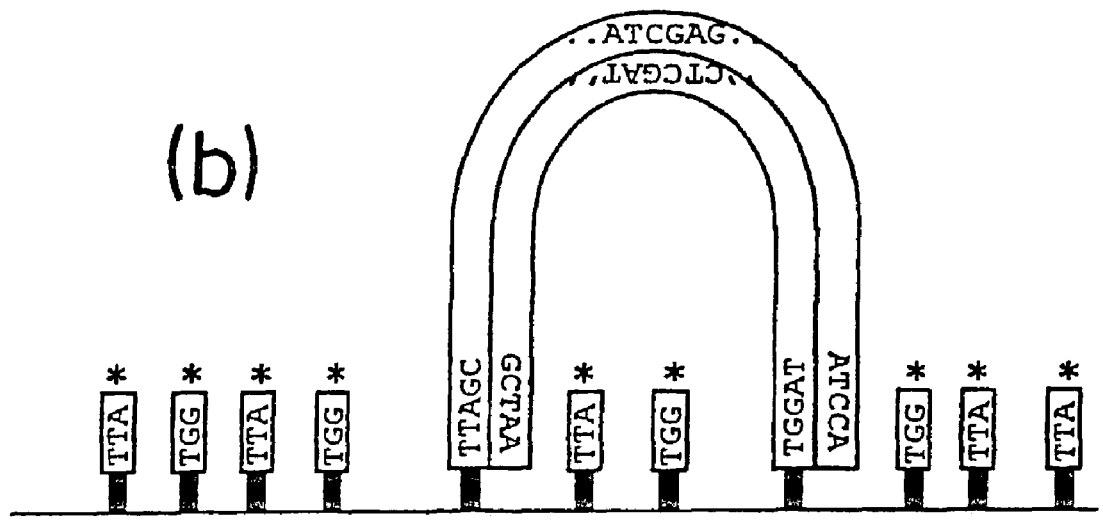
(b)

FIG. 12B
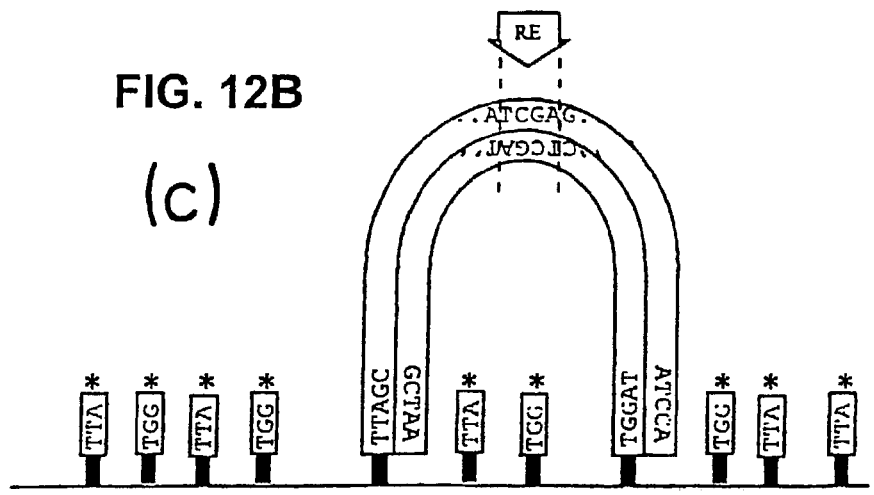
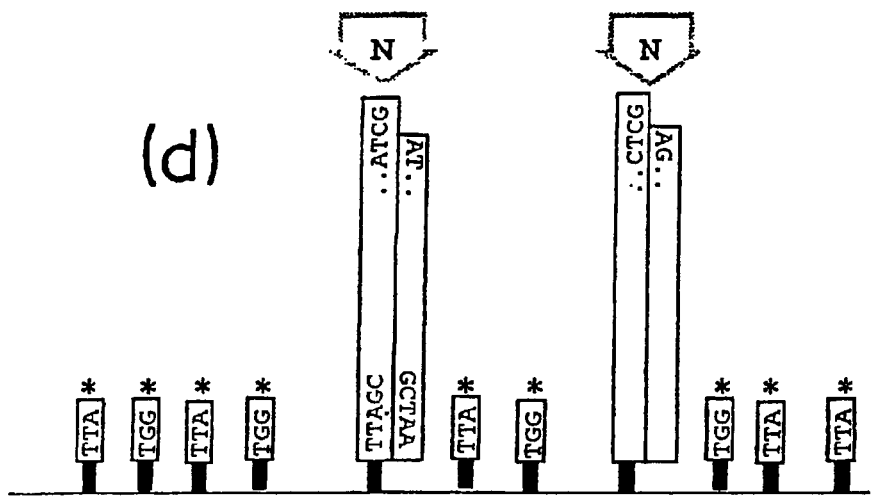
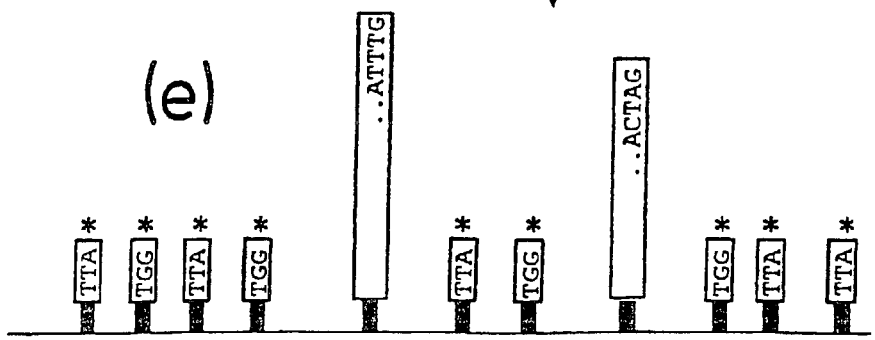

FIG. 12C
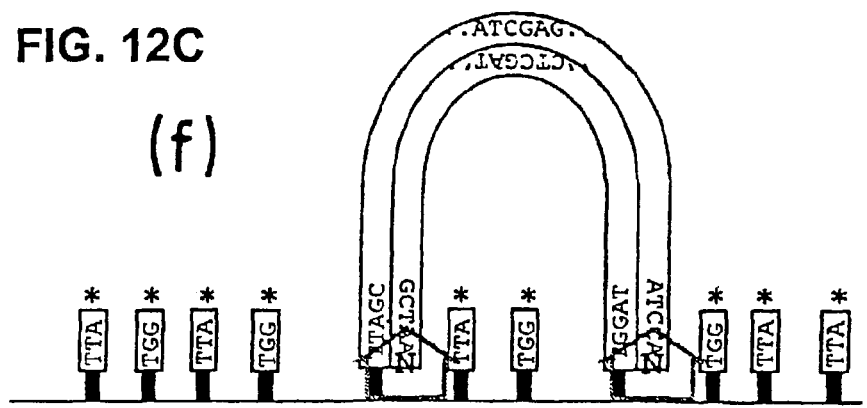
(f)
(iv)
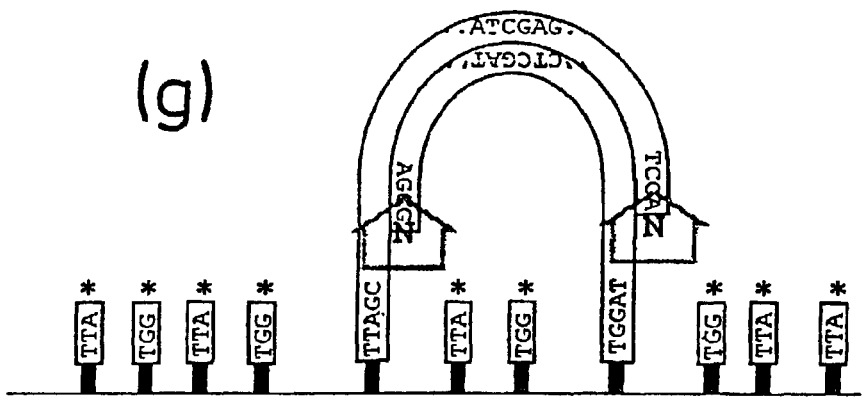
(g)
(v)
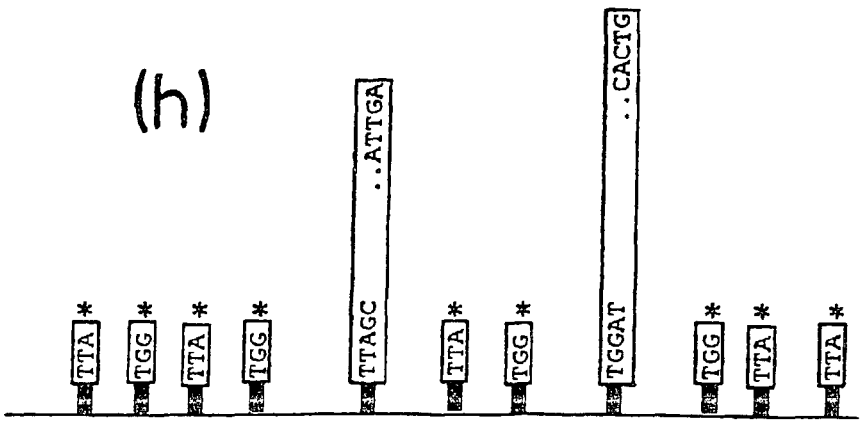
(h)

FIG. 13A
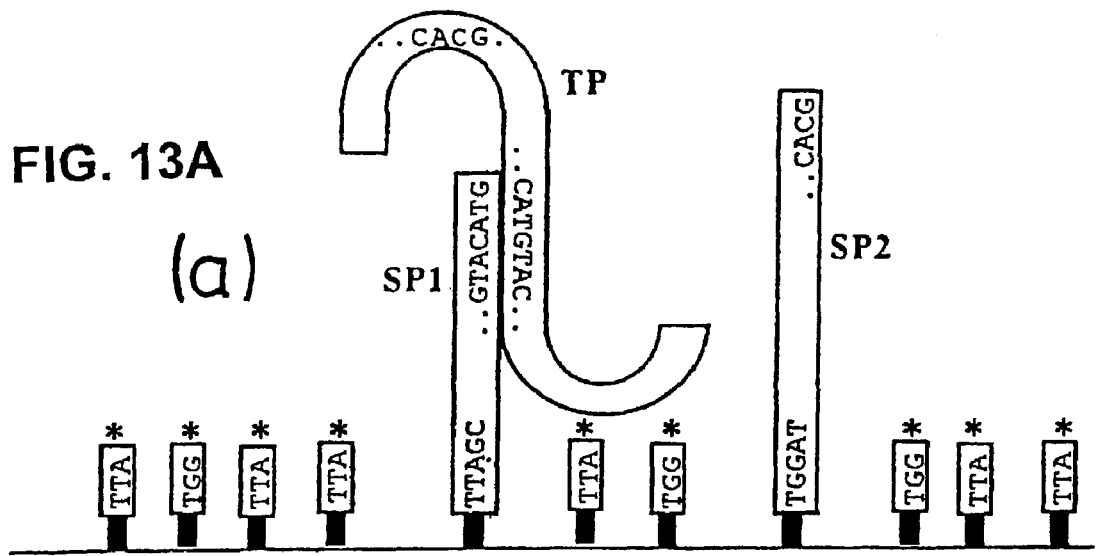
(a)
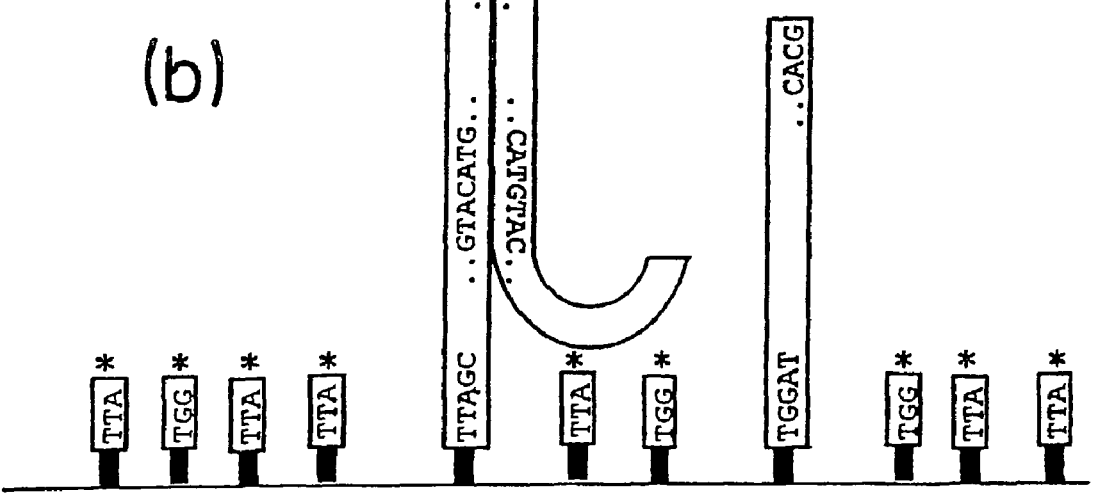
(b)

FIG. 14A
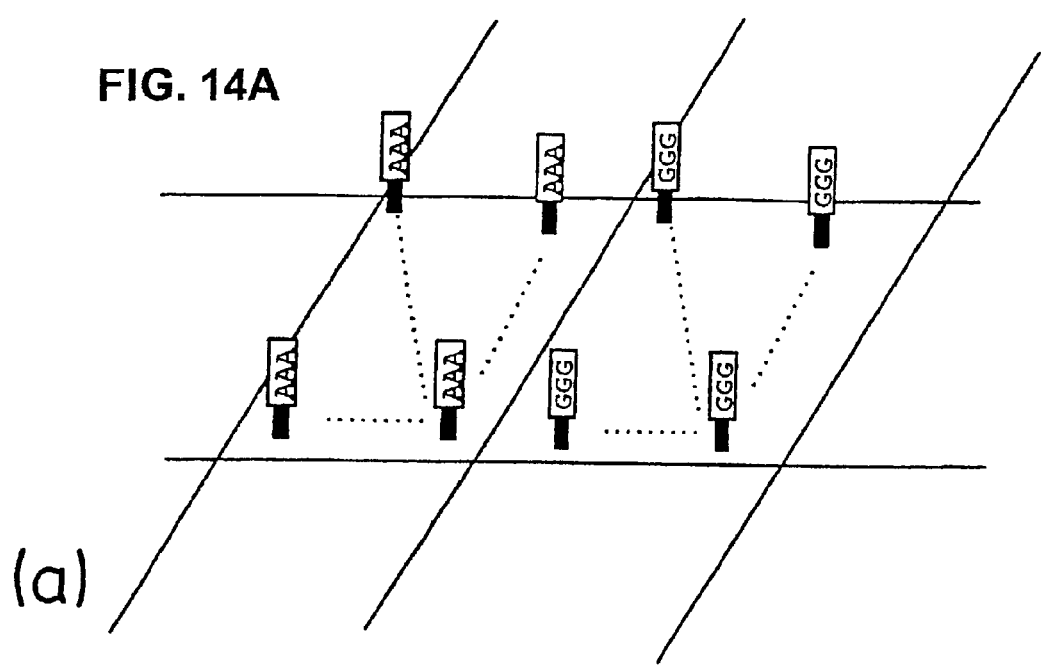
(a)
(i)
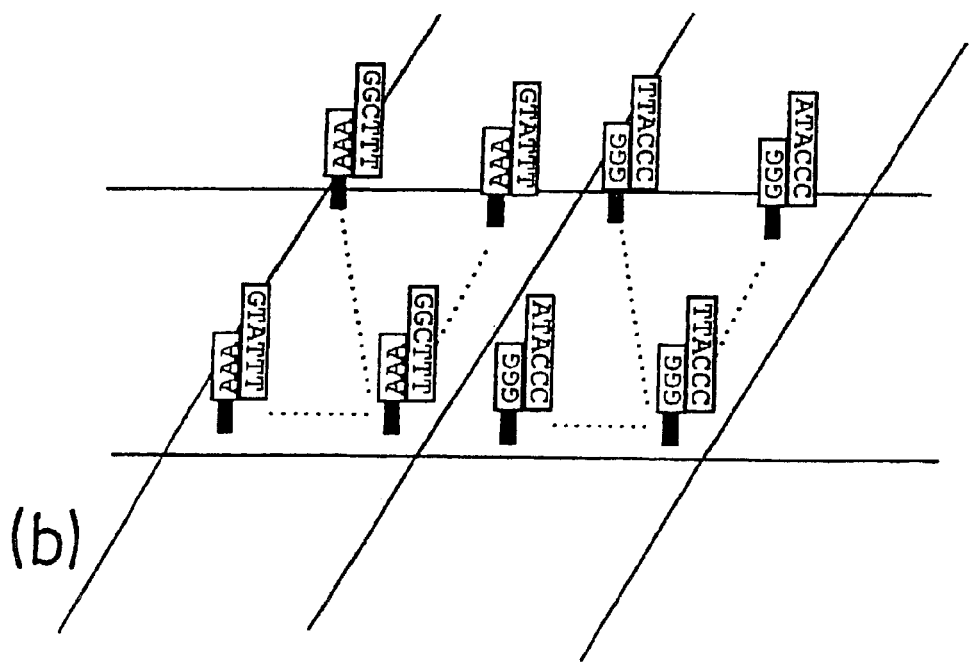
(b)
(ii)

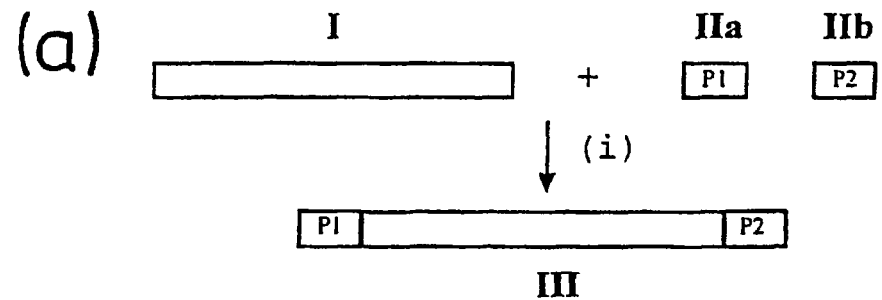
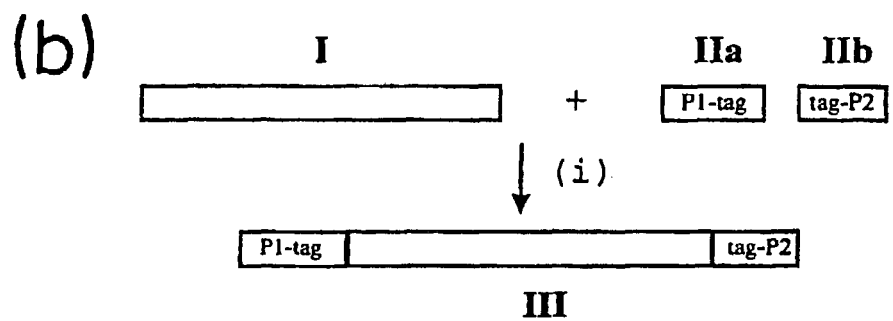
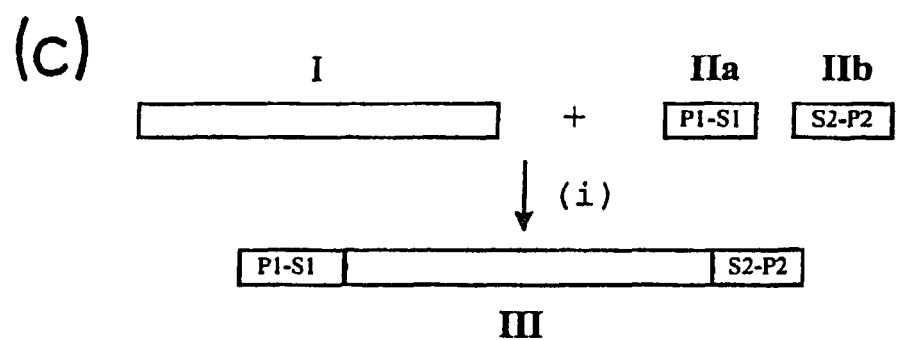
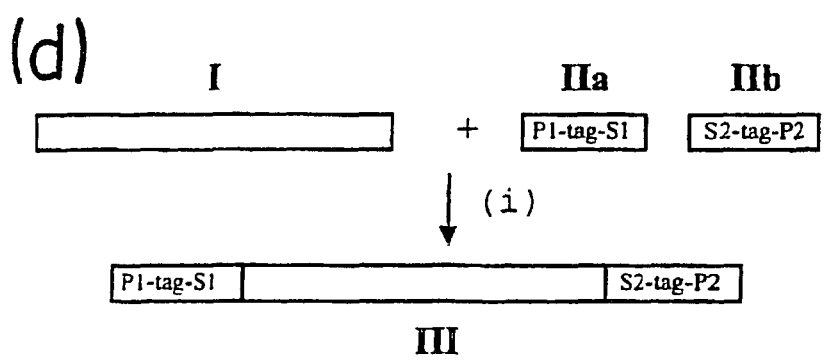
FIG. 15

FIG. 17
*in situ* Sequencing
(a)
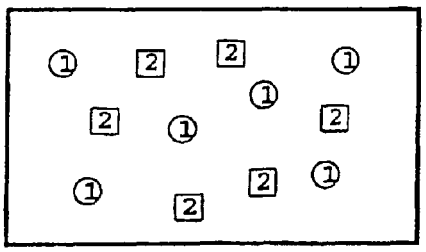
Two types of randomly arrayed DNA colonies
(b) step 1 add dGTP
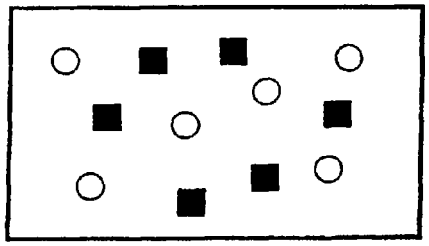
(c) step 2 add dATP
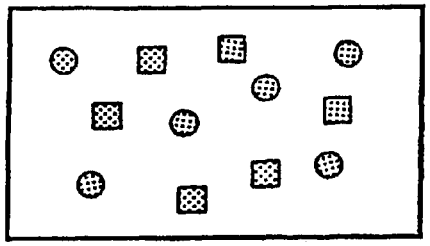
f)
(d) step 3 add dTTP
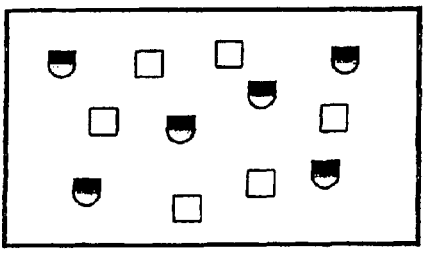
(e) step 4 add dCTP
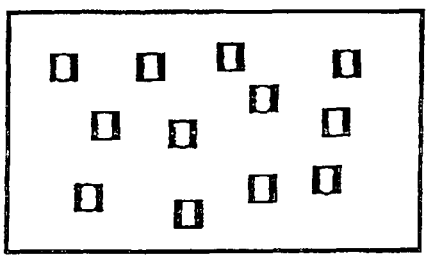
DNA sequence:
type 1: ATC
type 2: GAC

SEQUENCE LISTING (1) GENERAL INFORMATION:

(iii) NUMBER OF SEQUENCES: 16

(2) INFORMATION FOR SEQ ID NO: 1:

(i) SEQUENCE CHARACTERISTICS:
      (A) LENGTH: 30 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO: 1:

TTTTTTCACC AACCCAAACC AACCCAAACC                                           30

(2) INFORMATION FOR SEQ ID NO: 2:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 2:

TTTTTTAGAA GGAGAAGGAA AGGGAAAGGG                                           30

(2) INFORMATION FOR SEQ ID NO: 3:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 3:

AGAAGGAGAA GGAAAGGGAA AGGG                                                 24

(2) INFORMATION FOR SEQ ID NO: 4:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 4:

CCCTTTCCCT TCCTTCTCC TTCT                                                  24

(2) INFORMATION FOR SEQ ID NO: 5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 5:

GCGCGTAATA CGACTCACTA                                                      20

(2) INFORMATION FOR SEQ ID NO: 6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 6:

CGCAATTAAC CCTCACTAAA                                                      20

(2) INFORMATION FOR SEQ ID NO: 7:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 7:

```
TTTTTTCTCA CTATAGGGCG AATTGG                                  26
```

(2) INFORMATION FOR SEQ ID NO: 8:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 8:

```
TTTTTTCTCA CTAAAGGGAA CAAAAGCTGG                              30
```

(2) INFORMATION FOR SEQ ID NO: 9:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 9:

```
TTTTTTTTTT CACCAACCCA AACCAACCCA AACC                         34
```

(2) INFORMATION FOR SEQ ID NO: 10:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 10:

```
TTTTTTTTTT AGAAGGAGAA GGAAAGGGAA AGGG                         34
```

(2) INFORMATION FOR SEQ ID NO: 11:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 11:

```
CACCAACCCA AACCAACCCA AACCACGACT CACTATAGGG CGAA              44
```

(2) INFORMATION FOR SEQ ID NO: 12:

(i) SEQUENCE CHARACTERISTICS:
        (A) LENGTH: 44 base pairs

```
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 12:

AGAAGGAGAA GGAAAGGGAA AGGGTAAAGG GAACAAAAGC TGGA                44

(2) INFORMATION FOR SEQ ID NO: 13:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 13:

GGTGCTGGTC CTCAGTCTGT                                           20

(2) INFORMATION FOR SEQ ID NO: 14:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 14:

CCCGCTTACC AGTTTCCATT                                           20

(2) INFORMATION FOR SEQ ID NO: 15:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 15:

CTGGCCTTAT CCCTAACAGC                                           20

(2) INFORMATION FOR SEQ ID NO: 16:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 16:

CGATCTTGGC TCATCACAAT                                           20
```

METHOD OF NUCLEIC ACID AMPLIFICATION

CROSS-REFERENCE TO RELATED APPLICATIONS

This application is a continuation of U.S. application Ser. No. 09/402,277, filed Sep. 30, 1999, now abandoned, which is a §371 of PCT/GB98/00961, filed Apr. 1, 1998, the entire contents of each being incorporated herein.

This invention relates, inter alia, to the amplification of nucleic acids.

Molecular biology and pharmaceutical drug development now make intensive use of nucleic acid analysis (Friedrich, G. A. Moving beyond the genome projects, *Nature Biotechnology* 14, 1234 (1996)). The most challenging areas are whole genome sequencing, single nucleotide polymorphism detection, screening and gene expression monitoring. Currently, up to hundreds of thousands of samples are handled in single DNA sequencing projects (Venter, J. C., H. O Smith, L. Hood, A new strategy for genome sequencing, *Nature* 381, 364 (1996)). This capacity is limited by the available technology. Projects like the "human genome project" (gene mapping and DNA sequencing) and identifying all polymorphisms in expressed genes involved in common diseases imply the sequencing of millions of DNA samples.

With most of the current DNA sequencing technologies, it is simply not possible to decrease indefinitely the time required to process a single sample. A way of increasing throughput is to perform many processes in parallel. The introduction of robotic sample preparation and delivery, 96 and 384 well plates, high density gridding machines (Maier, E., S. Meierewer, A. R. Ahmadi, J. Curtis, H. Lehrach, Application of robotic technology to automated sequence fingerprint analysis by oligonucleotide hybridization, *Journal Of Biotechnology* 35, 191 (1994)) and recently the development of high density oligonucleotide arrays (Chee, M., R. Yang, E. Hubbell, A. Berno, X. C. Huang, D. Stern, J. Winkler, D. J. Lockhart, M. S. Morris, and S. P. A. Fodor, Accessing genetic information with high-density DNA arrays, *Science* 274(5287):610-614, (1996)) are starting to bring answers to the demand in ever higher throughput. Such technologies allow up to 50,000~100,000 samples at a time to be processed within days and even hours (Maier, E., Robotic technology in library screening, *Laboratory Robotics and Automation* 7, 123 (1995)).

In most known methods for performing nucleic acid analysis, it is necessary to first extract the nucleic acids of interest (e.g., genomic or mitochondrial DNA or messenger RNA (mRNA)) from an organism. Then it is necessary to isolate the nucleic acids of interest from the mixture of all nucleic acids and usually, to amplify these nucleic acids to obtain quantities suitable for their characterisation and/or detection. Isolating the nucleic fragments has been considered necessary even when one is interested in a representative but random set of all of the different nucleic acids, for instance, a representative set of all the mRNAs present in a cell or of all the fragments obtained after genomic DNA has been cut randomly into small pieces.

Several methods can be used to amplify DNA with biological means and are well known by those skilled in the art. Generally, the fragments of DNA are first inserted into vectors with the use of restriction enzymes and DNA ligases. A vector containing a fragment of interest can then be introduced into a biological host and amplified by means of well established protocols. Usually hosts are randomly spread over a growth medium (e.g. agar plates). They can then replicate to provide colonies that originated from individual host cells.

Up to millions of simultaneous amplification of cloned DNA fragments can be carried out simultaneously in such hosts. The density of colonies is of the order of 1 colony/mm$^2$. In order to obtain DNA from such colonies one option is to transfer the colonies to a membrane, and then to immobilise the DNA from within the biological hosts directly to the membrane (Grunstein, M. and D. S. Hogness, Colony Hybridization: A method for the isolation of cloned DNAs that contain a specific gene, *Proceedings of the National Academy of Science, USA,* 72:3961 (1975)). With these options however, the amount of transferred DNA is limited and often insufficient for non-radioactive detection.

Another option is to transfer by sterile technique individually each colony into a container (e.g., 96 well plates) where further host cell replication can occur so that more DNA can be obtained from the colonies. Amplified nucleic acids can be recovered from the host cells with an appropriate purification process. However such a procedure is generally time and labour consuming, and difficult to automate.

The revolutionary technique of DNA amplification using the polymerase chain reaction (PCR) was proposed in 1985 by Mullis et al. (Saiki, R., S. Scharf, F. Faloona, K. Mullis, G. Horn, H. Erlich and N. Arnheim, *Science* 230, 1350-1354 (1985) and is now well known by those skilled in the art. In this amplification process, a DNA fragment of interest can be amplified using two short (typically about 20 base long) oligonucleotides that flank a region to be amplified, and that are usually referred to as "primers". Amplification occurs during the PCR cycling, which includes a step during which double stranded DNA molecules are denatured (typically a reaction mix is heated, e.g. to 95° C. in order to separate double stranded DNA molecules into two single stranded fragments), an annealing step (where the reaction mix is brought to e.g., 45° C. in order to allow the primers to anneal to the single stranded templates) and an elongation step (DNA complementary to the single stranded fragment is synthesised via sequential nucleotide incorporation at the ends of the primers with the DNA polymerase enzyme).

The above procedure is usually performed in solution, whereby neither the primers nor a template are linked to any solid matrix.

More recently, however, it has been proposed to use one primer grafted to a surface in conjunction with free primers in solution in order to simultaneously amplify and graft a PCR product onto the surface (Oroskar, A. A., S. E. Rasmussen, H. N. Rasmussen, S. R. Rasmussen, B. M. Sullivan, and A. Johansson, Detection of immobilised amplicons by ELISA-like techniques, *Clinical Chemistry* 42:1547 (1996)). (The term "graft" is used herein to indicate that a moiety becomes attached to a surface and remains there unless and until it is desired to remove it.) The amplification is generally performed in containers (e.g., in 96 well format plates) in such a way that each container contains the PCR product(s) of one reaction. With such methods, some of the PCR product become grafted to a surface of the container having primers therein which has been in contact with the reactant during the PCR cycling. The grafting to the surface simplifies subsequent assays and allows efficient automation.

Arraying of DNA samples is more classically performed on membranes (e.g., nylon or nitro-cellulose membranes). With the use of suitable robotics (e.g., Q-bot™, Genetix ltd, Dorset BH23 3TG UK) it is possible to reach a density of up to 10 samples/mm$^2$. Here, the DNA is covalently linked to a membrane by physicochemical means (e.g., UV irradiation).

These technologies allow the arraying of large DNA molecules (e.g. molecules over 100 nucleotides long) as well as smaller DNA molecules. Thus both templates and probes can be arrayed.

New approaches based on pre-arrayed glass slides (arrays of reactive areas obtained by ink-jet technology (Blanchard, A. P. and L. Hood, Oligonucleotide array synthesis using ink jets, *Microbial and Comparative Genomics*, 1:225 (1996)) or arrays of reactive polyacrylamide gels (Yershov, G. et al., DNA analysis and diagnostics on oligonucleotide microchips, *Proceedings of the National Academy of Science, USA*, 93:4913-4918 (1996)) allow the arraying of up to 100 samples/mm$^2$. With these technologies, only probe (oligonucleotide) grafting has been reported. Reported number of samples/mm$^2$ are still fairly low (25 to 64).

Higher sample densities are achievable by the use of DNA chips, which can be arrays of oligonucleotides covalently bound to a surface and can be obtained with the use of microlithographic techniques (Fodor, S. P. A. et al., Light directed, spatially addressable parallel chemical synthesis, *Science* 251:767(1991)). Currently, chips with 625 probes/mm$^2$ are used in applications for molecular biology (Lockhart, D. J. et al., Expression monitoring by hybridisation to high-density oligonucleotide arrays, *Nature Biotechnology* 14:1675 (1996). Probe densities of up to 250 000 samples/cm$^2$ are claimed to be achievable (Chee, M. et al., Accessing genetic information with high-density DNA arrays, *Science* 274:610 (1996)). Currently, up to 132000 different oligonucleotides can be arrayed on a single chips of approximately 2.5 cm$^2$. Presently, these chips are manufactured by direct solid phase oligonucleotide synthesis with the 3'OH end of the oligo attached to the surface. Thus these chips have been used to provide oligonucleotide probes which cannot act as primers in a DNA polymerase-mediated elongation step.

When PCR products are linked to the vessel in which PCR amplification takes place, this can be considered as a direct arraying process. The density of the resultant array of PCR products is then limited by the available vessel. Currently available vessels are only in 96 well microtiter plate format. These allow only around ~0.02 samples of PCR products/mm$^2$ of surface to be obtained.

Using the commercially available Nucleolink™ system obtainable from Nunc A/S (Roskilde, Denmark) it is possible to achieve simultaneous amplification and arraying of samples in containers on the surface of which oligonucleotide primers have been grafted. However, in this case the density of the array of samples is fixed by the size of the vessel. Presently a density of 0.02 samples/mm$^2$ is achievable for the 96 well plate format. Increasing this density is difficult. This is apparent since, for instance, the availability of 384 well plates (0.08 samples/mm$^2$) suitable for PCR has been delayed due to technical problems (e.g. heat transfer and capillary effects during filling). It is thus unlikely that orders of magnitude improvements in the density of samples arrayed with this approach can be achieved in the foreseeable future.

The present invention aims to overcome or at least alleviate some of the disadvantages of prior art methods of nucleic acid amplification.

According to the present invention there is provided a method of nucleic acid amplification, comprising the steps of:
A. providing a plurality of primers that are immobilised but that have one end exposed to allow primer extension;
B. allowing a single stranded target nucleic acid molecule to anneal to one of said plurality of primers over part of the length of said single stranded nucleic acid molecule and then extending that primer using the annealed single stranded nucleic acid molecule as a template, so as to provide an extended immobilised nucleic acid strand;
C. separating the target nucleic molecule from the extended immobilised nucleic acid strand;
D. allowing the extended immobilised nucleic acid strand to anneal to one of said plurality of primers referred to in step A) and then extending that primer using the extended immobilised nucleic acid strand as a template, so as to provide another extended immobilised nucleic acid strand; and optionally,
E. separating the annealed extended immobilised nucleic acid strands from one another.

Preferably the method also comprises the step of:
F. using at least one extended immobilised nucleic acid strand to repeat steps D) and E), so as to provide additional extended immobilised nucleic acid strands and, optionally,
G. repeating step F) one or more times.

Desirably the single-stranded target nucleic acid sequence is provided by a method in which said single-stranded target nucleic acid is produced by providing a given nucleic acid sequence to be amplified (which sequence may be known or unknown) and adding thereto a first nucleic acid sequence and a second nucleic acid sequence; wherein said first nucleic acid sequence hybridises to one of said plurality of primers and said second nucleic acid sequence is complementary to a sequence which hybridises to one of said plurality of primers.

The second nucleic acid sequence may be a sequence that is the same as the sequence of one of the plurality of primers. Thus the single-stranded target nucleic acid squence may be provided by a method in which said single-stranded target nucleic acid is produced by providing a given nucleic acid sequence to be amplified (which sequence may be known or unknown) and adding thereto a first nucleic acid sequence and a second nucleic acid sequence; wherein said first nucleic acid sequence hybridises to one of said plurality of primers and said second nucleic acid sequence is the same as the-sequence of one of said plurality of primers.

The first and second nucleic acid sequences may be provided at first and second ends of said single-stranded target nucleic acid, although this is not essential.

If desired a tag may be provided to enable amplification products of a given nucleic acid sequence to be identified.

Colonies

The method of the present invention allows one or more distinct areas to be provided, each distinct area comprising a plurality of immobilised nucleic acid strands (hereafter called "colonies"). These areas can contain large numbers of amplified nucleic acid molecules. These molecules may be DNA and/or RNA molecules and may be provided in single or double stranded form. Both a given strand and its complementary strand can be provided in amplified form in a single colony.

Colonies of any particular size can be provided. However, preferred colonies measure from 10 nm to 100 µm across their longest dimension, more preferably from 100 nm to 10 µm across their longest dimension. Desirably a majority of the colonies present on a surface (i.e. at least 50% thereof) have sizes within the ranges given above.

Colonies can be arranged in a predetermined manner or can be randomly arranged. Two or three dimensional colony configurations are possible. The configurations may be regular (e.g. having a polygonal outline or having a generally circular outline) or they may be irregular.

Colonies can be provided at high densities. Densities of over one colony/mm$^2$ of surface can be achieved. Indeed densities of over $10^2$, over $10^3$ or even over $10^4$ colonies/mm$^2$ are achievable using the present invention. In preferred embodiments, the present invention provides colony densities of $10^{4-5}$ colonies/mm$^2$, more preferably densities of $10^{6-7}$ colonies/mm$^2$, thus offering an improvement of 3 to 4 orders of magnitude relative to densities achievable using many of the prior art methods. It is this property of the invention that allows a great advantage over prior art, since the high density of DNA colonies allows a large number of diverse DNA templates (up to $10^{6-7}$ colonies/mm$^2$, to be randomly arrayed and amplified.

Primers

The immobilised primers for use in the present invention can be provided by any suitable means, as long as a free 3'-OH end is available for primer extension. Where many different nucleic acid molecules are to be amplified, many different primers may be provided. Alternatively "universal" primers may be used, whereby only one or two different types of primer (depending upon the embodiment of the invention) can be used to amplify the different nucleic acid molecules. Universal primers can be used where the molecules to be amplified comprise first and second sequences, as described previously. The provision of universal primers is advantageous over methods such as those disclosed in WO96/04404 (Mosaic Technologies, Inc.) where specific primers must be prepared for each particular sequence to be amplified.

Synthetic oligodeoxynucleotide primers are available commercially from many suppliers (e.g. Microsynth, Switzerland, Eurogentech, Belgium).

Grafting of primers onto silanized glass or quartz and grafting of primers onto silicon wafers or gold surface has been described (Maskos, U. and E. M Southern, Oligonucleotide hybridizations on glass supports: a novel linker for oligonucleotide synthesis and hybridization properties of oligonucleotides synthesised in situ, *Nucleic Acids Research* 20(7):1679-84, 1992; Lamture, J. B., et. al. Direct-detection of nucleic-acid hybridization on the surface of a charge-coupled-device, *Nucleic Acids Research* 22(11):2121-2125, 1994; Chrisey, L. A., G. U. Lee, and C. E. Oferrall, Covalent attachment of synthetic DNA to self-assembled monolayer films, *Nucleic Acids Research* 24(15):3031-3039, 1996).

Grafting biotinylated primers to supports covered with streptavidin is another alternative. This grafting method is commonly used for bio-macromolecules in general.

Non covalent grafting of primers at the interface between an aqueous phase and a hydrophobic phase through an hydrophobic anchor is also possible for the present invention. Such anchoring is commonly used for bio-macromolecules in general (S. Terrettaz et al.: Protein binding to supported lipid membranes, *Langmuir* 9, 1361 (1993)). Preferred forms of such interfaces would be liposomes, lipidic vesicles, emulsions, patterned bilayers, Langmuir or Langmuir-Blodgett films. The patterns may be obtained by directed pattering on templates, e.g., silicon chips patterned through micro-lithographic methods (Goves, J. T. et al., Micropatterning Fluid Bilayers on Solid Supports, in *Science* 275,651 (1997)). The patterns may also be obtained by due to the self-assembly properties of "colloids", e.g., emulsions or latex particles (Larsen, A. E. and D. G. Grier, Like charge attractions in metastable colloidal crystallites, *Nature* 385,230 (1997)).

In the above methods, one, two or more different primers can be grafted onto a surface. The primers can be grafted homogeneously and simultaneously over the surface.

Using microlithographic methods it is possible to provide immobilised primers in a controlled manner. If direct synthesis of oligonucleotides onto a solid support with a free 3'-OH end is desired, then micro-lithographic methods can be used to simultaneously synthesise many different oligonucleotide primers (Pirrung, M. C. and Bradley, J. C. Comparison of methods for photochemical phosphoramidite-based DNA-synthesis. *Journal Of Organic Chemistry* 60(20):6270-6276, 1995). These may be provided in distinct areas that may correspond in configuration to colonies to be formed, (e.g. they may be several nanometers or micrometers across). Within each area, only a single type of primer oligonucleotide need be provided. Alternatively a mixture comprising a plurality of different primers may be provided. In either case, primers can be homogeneously distributed within each area. They may be provided in the form of a regular array.

Where areas initially comprise only one type of immobilised primer they may be modified, if desired, to carry two or more different types of primer. One way to achieve this is to use molecules as templates for primer extension that have 3' ends that hybridise with a single type of primer initially present and that have 5' ends extending beyond the 3' ends of said primers. By providing a mixture of templates with different sequences from one another, primer extension of one type of primer using the mixture of such templates followed by strand separation will result in different modified primers. (The modified primers are referred to herein as "extended" primers in order to distinguish from the "primary" primers initially present on a surface).

One, two or more different types of extended primer can be provided in this manner at any area where primary primers are initially located. Substantially equal portions of different templates can be used, if desired, in order to provide substantially equal proportions of different types of immobilised extended primer over a given area. If different proportions of different immobilised extended primers are desired, then this can be achieved by adjusting the proportions of different template molecules initially used accordingly A restriction endonuclease cleavage site may be located within the primer. A primer may also be provided with a restriction endonuclease recognition site which directs DNA cleavage several bases distant (Type II restriction endonucleases). (For the avoidance of doubt, such sites are deemed to be present even if the primer and its complement are required to be present in a double stranded molecule for recognition and/or cleavage to occur.) Alternatively a cleavage site and/or a recognition site may be produced when a primer is extended. In any event, restriction endonucleases can be useful in allowing an immobilised nucleic acid molecule within a colony to be cleaved so as to release at least a part thereof. As an alternative to using other restriction endonucleases, ribozymes can be used to release at least parts of nucleic acid molecules from a surface (when such molecules are RNA molecules). Other methods are possible. For example if a covalent bond is used to link a primer to a surface this bond may be broken (e.g. by chemical, physical or enzymatic means).

Primers for use in the present invention are preferably at least five bases long. Normally they will be less than 100 or less than 50 bases long. However this is not essential. Naturally occurring and/or non-naturally occurring bases may be present in the primers.

Target Nucleic Acid Molecules

Turning now to target nucleic acid molecules (also referred to herein as "templates") for use in the method of the present invention, these can be provided by any appropriate means. A target molecule (when in single-stranded form) comprises a first part having a sequence that can anneal with a first primer and a second part having a sequence complementary to a sequence that can anneal with a second primer. In a preferred embodiment the second part has the same sequence as the second primer.

The second primer may have a sequence that is the same as, or different from, the sequence of the first primer.

The first and second parts of the target nucleic acid molecules are preferably located at the 3' and at the 5' ends respectively thereof. However this is not essential. The target molecule will usually also comprise a third part located between the first and second parts. This part of the molecule comprises a particular sequence to be replicated. It can be from any desired source and may have a known or unknown (sometimes referred to as "anonymous") sequence. It may be derived from random fractionation by mechanical means or by limited restriction enzyme digestion of a nucleic acid sample, for example.

Further parts of the target molecules may be provided if desired. For example parts designed to act as tags may be provided. A "tag" is defined by its function of enabling a particular nucleic acid molecule (or its complement) to be identified.

Whatever parts are present, target nucleic acid molecules can be provided by techniques known to those skilled in the art of nucleic acid manipulation. For example, two or more parts can be joined together by ligation. If necessary, prior to ligation appropriate modifications can be made to provide molecules in a form ready for ligation. For example if blunt end ligation is desired then a single-strand specific exonuclease such as S1 nuclease could be used to remove single stranded portions of molecules prior to ligation. Linkers and/or adapters may also be used in nucleic acid manipulation. (Techniques useful for nucleic acid manipulation are disclosed in Sambrook et al, *Molecular Cloning*, $2^{nd}$ Edition, Cold Spring Harbor Laboratory Press (1989), for example.)

Once a template molecule has been synthesised it can be cloned into a vector and can be amplified in a suitable host before being used in the present invention. It may alternatively be amplified by PCR. As a further alternative, batches of template molecules can be synthesised chemically using automated DNA synthesisers (e.g. from Perkin-Elmer/Applied Biosystems, Foster City, Calif.).

It is however important to note that the present invention allows large numbers of nucleic acid molecules identical in sequence to be provided in a colony arising from a single molecule of template. Furthermore, the template can be reused to generate further colonies. Thus it is not essential to provide large numbers of template molecules to be used in colony formation.

The template can be of any desired length provided that it can participate in the method of the present invention. Preferably it is at least 10, more preferably at least 20 bases long. More preferably it is at least 100 or at least 1000 bases long. As is the case for primers for use in the present invention, templates may comprise naturally occurring and/or non-naturally occurring bases.

Reaction Conditions

Turning now to reaction conditions suitable for the method of the present invention, it will be appreciated that the present invention uses repeated steps of annealing of primers to templates, primer extension and separation of extended primers from templates. These steps can generally be performed using reagents and conditions known to those skilled in PCR (or reverse transcriptase plus PCR) techniques. PCR techniques are disclosed, for example, in "PCR: Clinical Diagnostics and Research", published in 1992 by Springer-Verlag.

Thus a nucleic acid polymerase can be used together with a supply of nucleoside triphosphate molecules (or other molecules that function as precursors of nucleotides present in DNA/RNA, such as modified nucleoside triphosphates) to extend primers in the presence of a suitable template.

Excess deoxyribonucleoside triphosphates are desirably provided. Preferred deoxyribonucleoside triphosphates are abbreviated; dTTP (deoxythymidine nucleoside triphosphate), DATP (deoxyadenosine nucleoside triphosphate), dCTP (deoxycytosine nucleoside triphosphate) and dGTP (deoxyguanosine nucleoside triphosphate). Preferred ribonucleoside triphosphates are UTP, ATP, CTP and GTP. However alternatives are possible. These may be naturally or non-naturally occurring. A buffer of the type generally used in PCR reactions may also be provided.

A nucleic acid polymerase used to incorporate nucleotides during primer extension is preferably stable under the pertaining reaction conditions in order that it can be used several times. (This is particularly useful in automated amplification procedures.) Thus, where heating is used to separate a newly synthesised nucleic acid strand from its template, the nucleic acid polymerase is preferably heat stable at the temperature used. Such heat stable polymerases are known to those skilled in the art. They are obtainable from thermophilic microorganisms. They include the DNA dependent DNA polymerase known as Taq polymerase and also thermostable derivatives thereof. (The nucleic acid polymerase need not however be DNA dependent. It may be RNA dependent. Thus it may be a reverse transcriptase—i.e. an RNA dependent DNA polymerase.)

Typically, annealing of a primer to its template takes place at a temperature of 25 to 90° C. Such a temperature range will normally be. maintained during primer extension. Once sufficient time has elapsed to allow annealing and also to allow a desired degree of primer extension to occur, the temperature can be increased, if desired, to allow strand separation. At this stage the temperature will typically be increased to a temperature of 60 to 100° C. [High temperatures can also be used to reduce non-specific priming problems prior to annealing. They can be used to control the timing of colony initiation, e.g. in order to synchronise colony initiation for a number of samples.] Alternatively, the strands maybe separated by treatment with a solution of low salt and high pH (>12) or by using a chaotropic salt (e.g. guanidinium hydrochloride) or by an organic solvent (e.g. formamide).

Following strand separation (e.g. by heating), preferably a washing step will be performed. The washing step can be omitted between initial rounds of annealing, primer extension and strand separation, if it is desired to maintain the same templates in the vicinity of immobilised primers. This allows templates to be used several times to initiate colony formation. (It is preferable to provide a high concentration of template molecules initially so that many colonies are initiated at one stage.)

The size of colonies can be controlled, e.g. by controlling the number of cycles of annealing, primer extension and strand separation that occur. Other factors which affect the size of colonies can also be controlled. These include the number and arrangement on a surface of immobilised primers, the conformation of a support onto which the primers are immobilised, the length and stiffness of template and/or primer molecules, temperature and the ionic strength and viscosity of a fluid in which the above-mentioned cycles can be performed.

Uses of Colonies

Once colonies have been formed they can be used for any desired purpose.

For example, they may be used in nucleic acid sequencing (whether partial or full), in diagnosis, in screening, as supports for other components and/or for research purposes (preferred uses will be described in greater detail later on). If desired colonies may be modified to provide different colonies (referred to herein as "secondary colonies" in order to distinguish from the "primary colonies" initially formed).

Surfaces Comprising Immobilised Nucleic Acid Strands

A surface comprising immobilised nucleic acid strands in the form of colonies of single stranded nucleic acid molecules is also within the scope of the present invention.

Normally each immobilised nucleic acid strand within a colony will be located on the surface so that an immobilised and complementary nucleic acid strand thereto is located on the surface within a distance of the length of said immobilised nucleic acid strand (i.e. within the length of one molecule). This allows very high densities of nucleic acid strands and their complements to be provided in immobilised form. Preferably there will be substantially equal proportions of a given nucleic acid strand and its complement within a colony. A nucleic acid strand and its complement will preferably be substantially homogeneously distributed within the colony.

It is also possible to provide a surface comprising single stranded nucleic acid strands in the form of colonies, where in each colony, the sense and anti-sense single strands are provided in a form such that the two strands are no longer at all complementary, or simply partially complementary. Such surfaces are also within the scope of the present invention. Normally, such surfaces are obtained after treating primary colonies, e.g., by partial digestion by restriction enzymes or by partial digestion after strand separation (e.g., after heating) by an enzyme which digests single stranded DNA), or by chemical or physical means, (e.g., by irradiating with light colonies which have been stained by an intercalating dye e.g., ethidium bromide).

Once single stranded colonies have been provided they can be used to provide double stranded molecules. This can be done, for example, by providing a suitable primer (preferably in solution) that hybridises to the 3' ends of single stranded immobilised molecules and then extending that primer using a nucleic acid polymerase and a supply of nucleoside triphosphates (or other nucleotide precursors).

Thus surfaces comprising colonies of non-bridged double stranded nucleic acid molecules are also within the scope of the present invention. (The term "non-bridged" is used here to indicate that the molecules are not in the form of the bridge-like structures shown in e.g. FIG. 1h.)

Using the present invention, small colonies can be provided that contain large numbers of nucleic acid molecules (whether single or double stranded). Many colonies can therefore be located on a surface having a small area. Colony densities that can be obtained may therefore be very high, as discussed supra.

Different colonies will generally be comprised of different amplified nucleic acid strands and amplified complementary strands thereto. Thus the present invention allows many different populations of amplified nucleic acid molecules and their complements to be located on a single surface having a relatively small surface area. The surface will usually be planar, although this is not essential.

Apparatuses

The present invention also provides an apparatus for providing a surface comprising colonies of the immobilised nucleic acid molecules discussed supra.

Such an apparatus can include one or more of the following:
a) means for immobilising primers on a surface (although this is not needed if immobilised primers are already provided);
b) a supply of a nucleic acid polymerase;
c) a supply of precursors of the nucleotides to be incorporated into a nucleic acid (e.g. a supply of nucleoside triphosphates);
d) means for separating annealed nucleic acids (e.g. heating means); and
e) control means for co-ordinating the different steps required for the method of the present invention.

Other apparatuses are within the scope of the present invention. These allow immobilised nucleic acids produced via the method of the present invention to be analysed. They can include a source of reactants and detecting means for detecting a signal that may be generated once one or more reactants have been applied to the immobilised nucleic acid molecules. They may also be provided with a surface comprising immobilised nucleic acid molecules in the form of colonies, as described supra.

Desirably the means for detecting a signal has sufficient resolution to enable it to distinguish between signals generated from different colonies.

Apparatuses of the present invention (of whatever nature) are preferably provided in automated form so that once they are activated, individual process steps can be repeated automatically.

The present invention will now be described without limitation thereof in sections A to I below with reference to the accompanying drawings.

It should be appreciated that procedures using DNA molecules referred to in these sections are applicable mutatis mutandis to RNA molecules, unless the context indicates otherwise.

It should also be appreciated that where sequences are provided in the following description, these are written from 5' to 3' (going from left to right), unless the context indicates otherwise.

The figures provided are summarised below:

FIG. 2 illustrates how colony growth using a method of the present invention can occur.

FIGS. 3A and 3B illustrate the principle of the method used to produce DNA colonies using the present invention. It also illustrates the annealing, elongation and denaturing steps that are used to provide such colonies.

FIG. 7 shows actual DNA colonies produced via the present invention.

FIG. 8 shows actual DNA colonies produced via the present invention.

FIG. 10A and FIG. 10B illustrate a method to synthesise additional copies of the original nucleic acid strands using nucleic acid strands present in colonies. The newly synthesised strands are shown in solution but can be provided in immobilised form if desired.

FIG. 11A and FIG. 11B show the PCR amplification of DNA from DNA found in the pre-formed DNA colonies.

FIG. 12A, FIG. 12B, and FIG. 12C illustrate how secondary primers can be generated from DNA colonies.

Figure 13B:
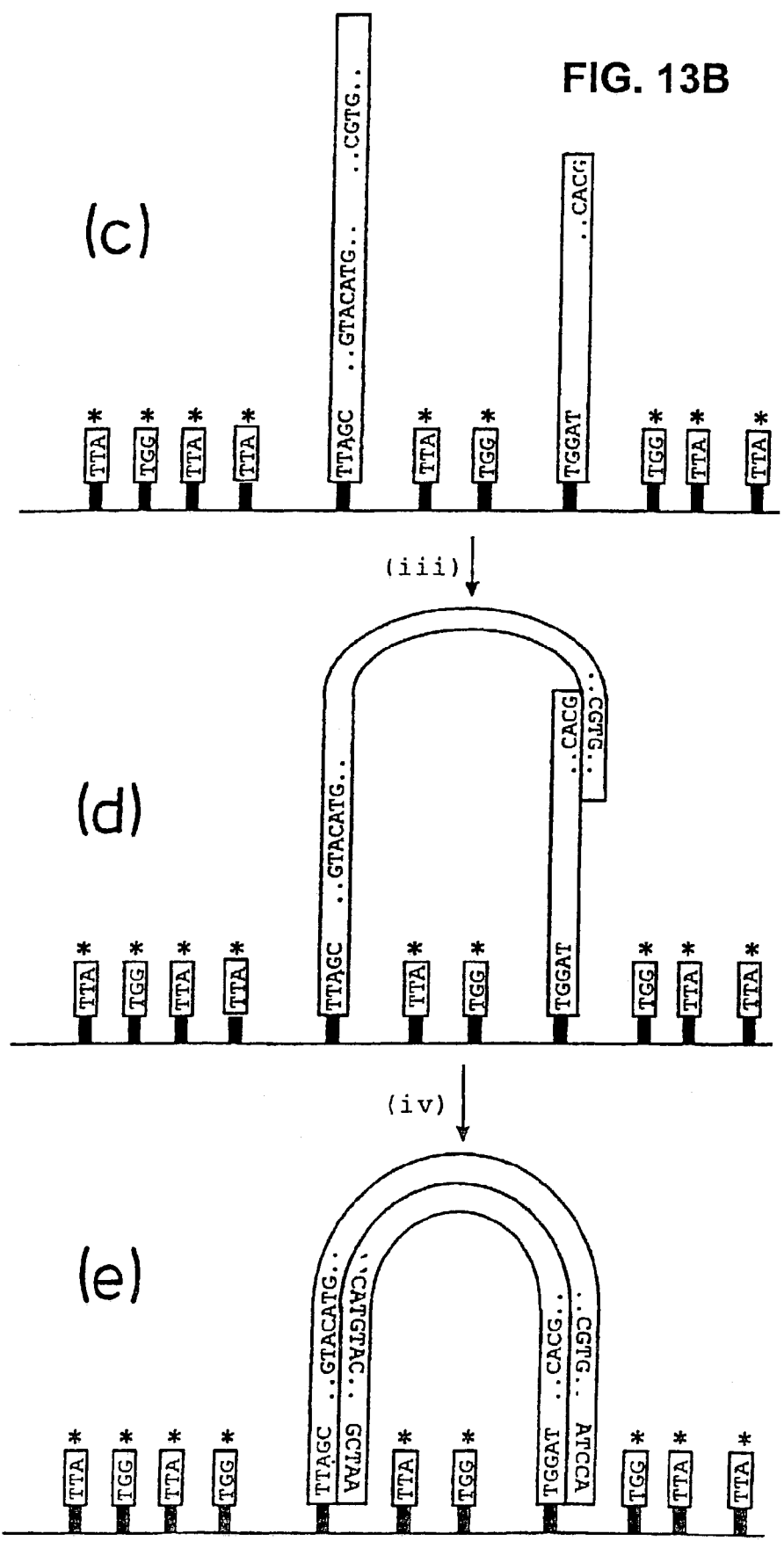

FIG. 13A and FIG. 13B illustrate how secondary DNA colonies can be generated from secondary primers.

Figure 14B:
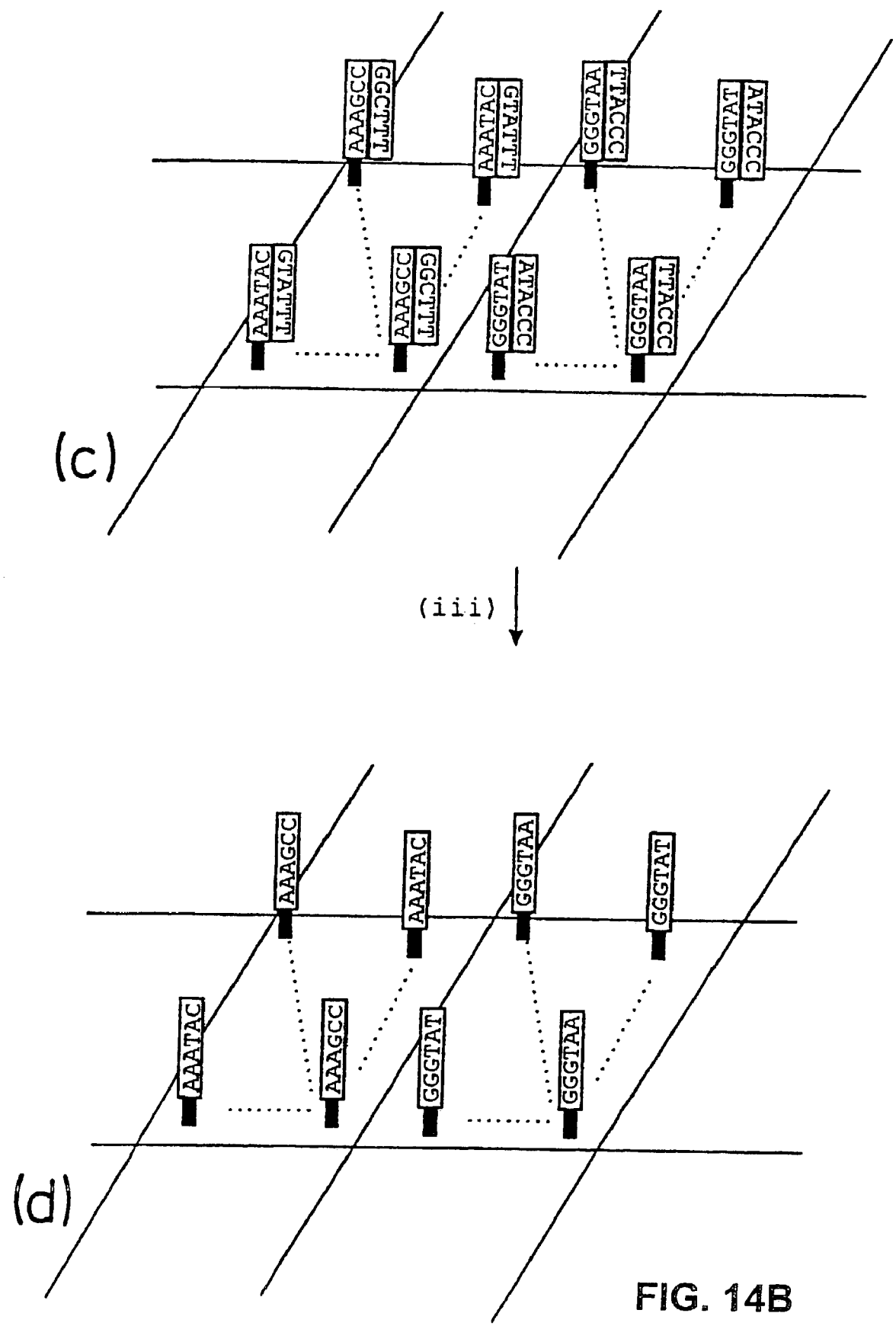

FIG. 14A and FIG. 14B illustrate how primers with different sequences can be generated from a surface functionalised with existing primers.

FIG. 15 depicts methods of preparing DNA fragments suitable for generating DNA colonies.

Figure 16:
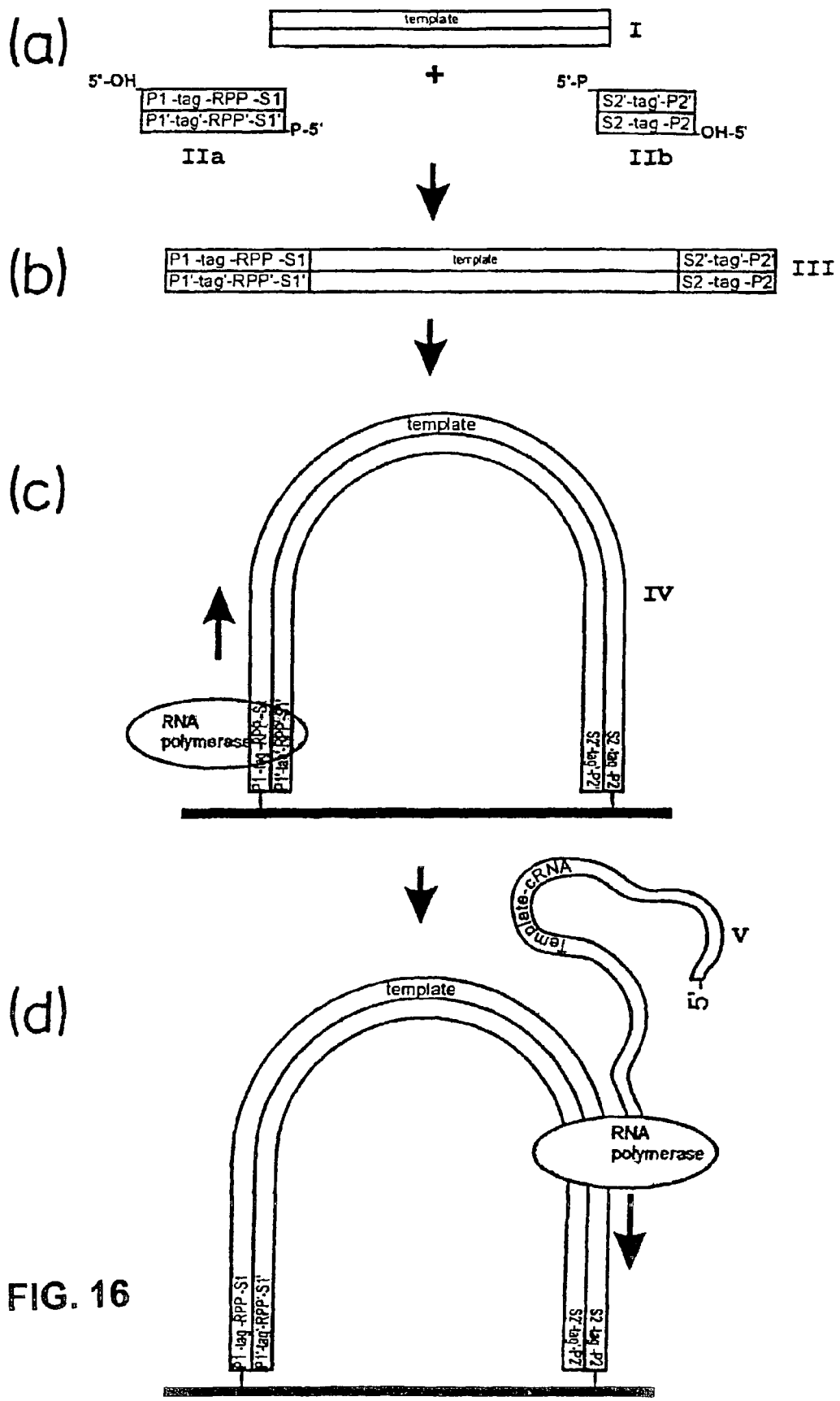

FIG. 16 illustrates a method for synthesising cRNA using the DNA colony as a substrate for RNA polymerase.

FIG. 17 illustrates a preferable method to determine the DNA sequence of DNA present in individual colonies.

Figure 18:
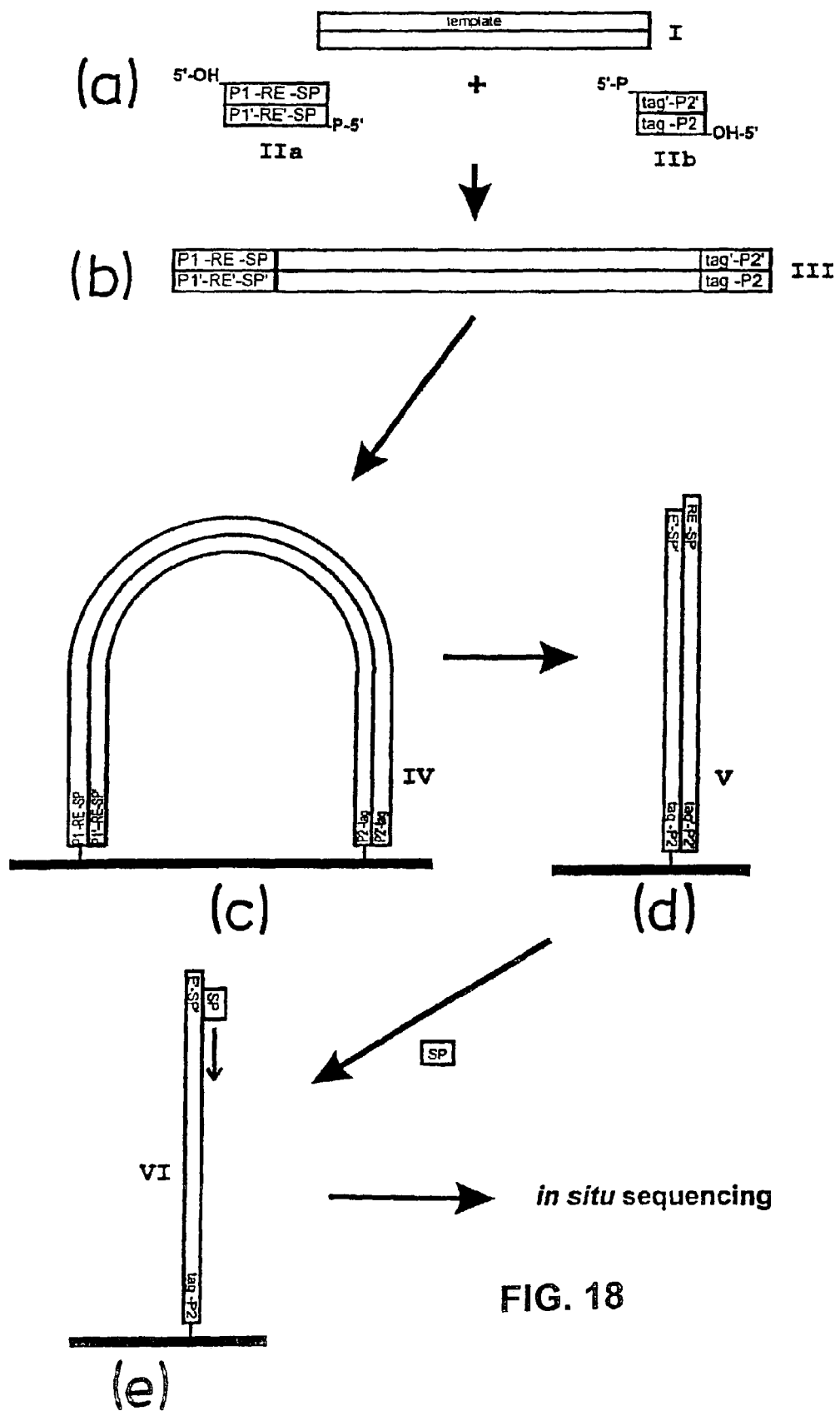

FIG. 18 illustrates a method of determining the sequence of a DNA colony, de novo.

Figure 19:
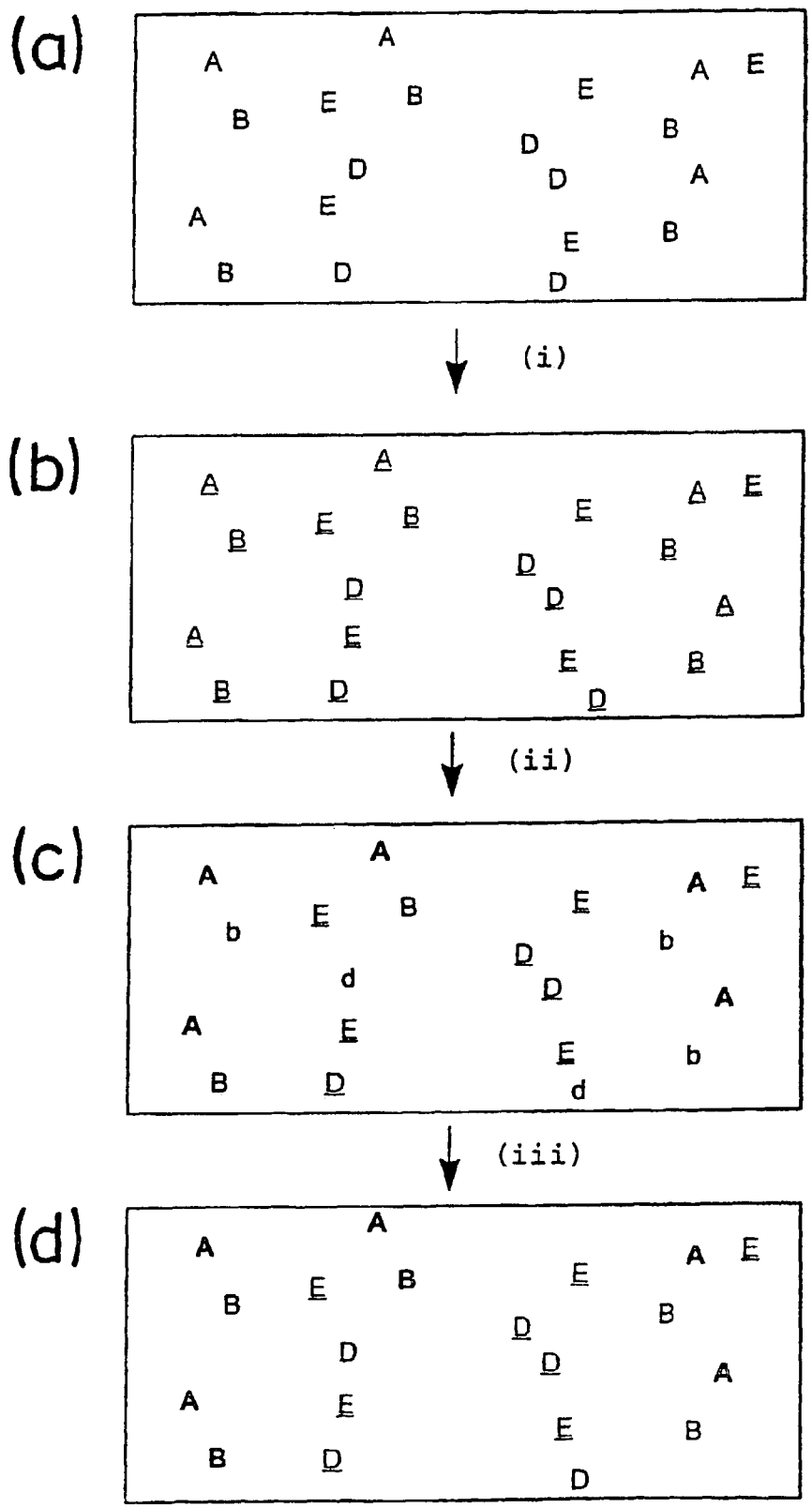

FIG. 19 illustrates the utility of secondary DNA colonies in the assay of mRNA expression levels.

Figure 20:
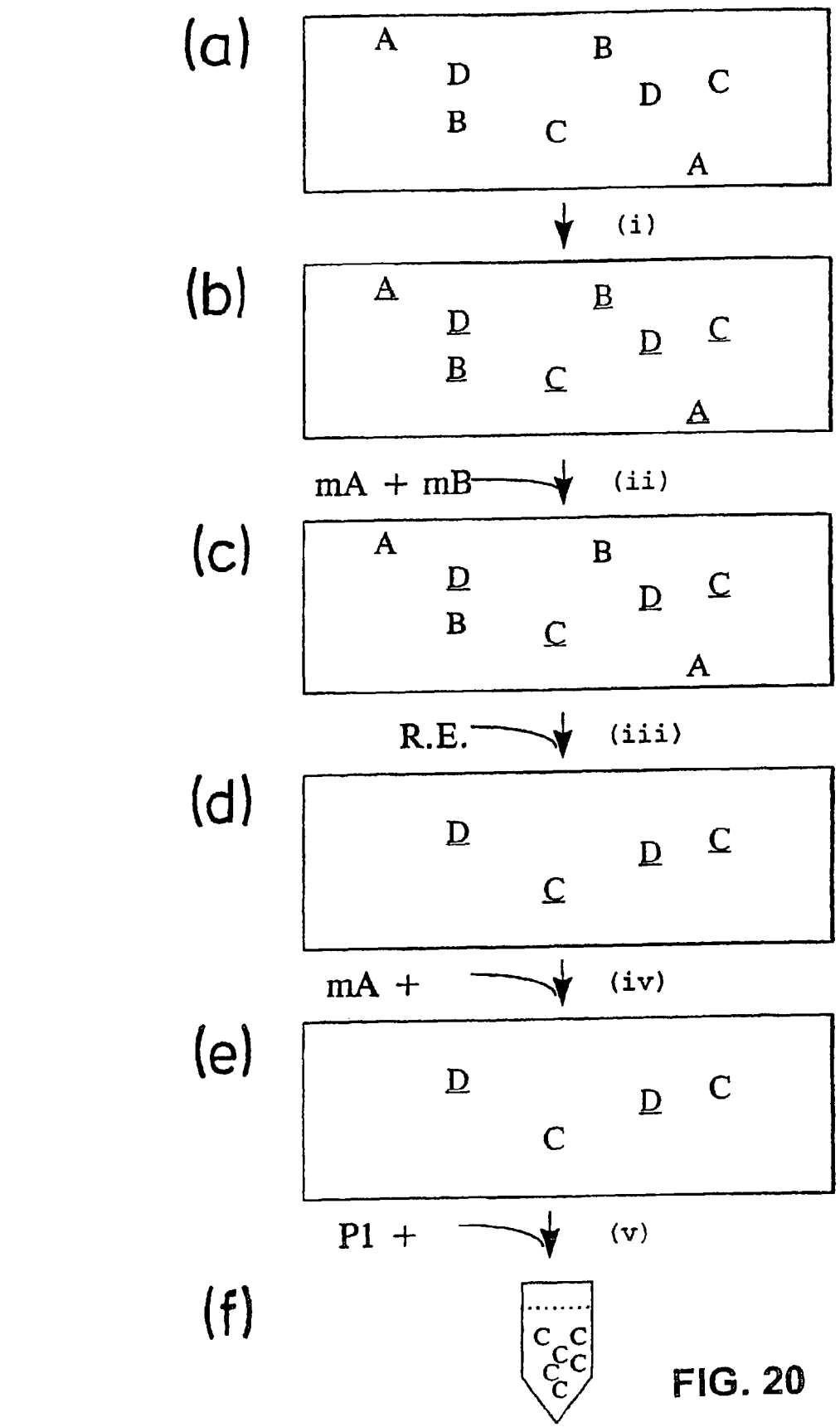
Figure 21:
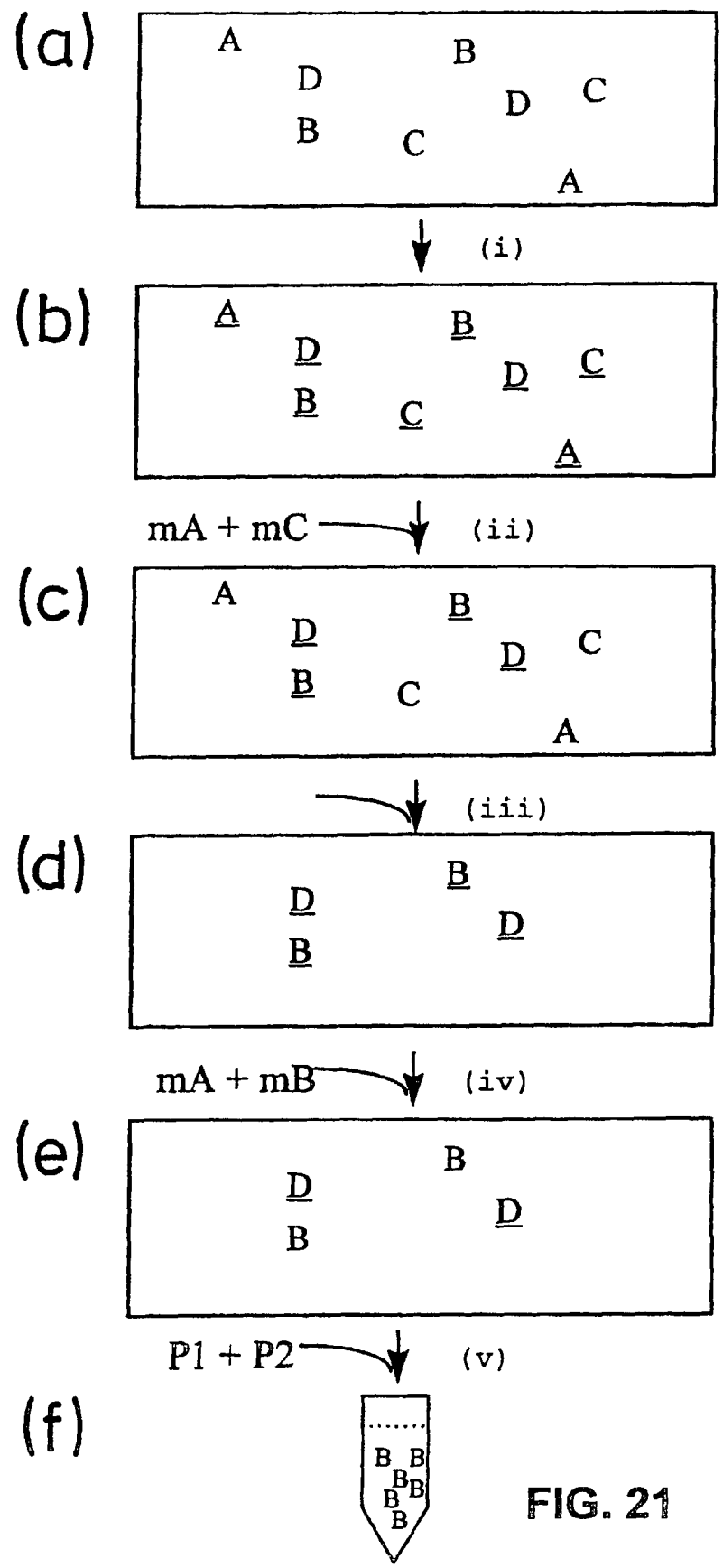

FIG. 20 and FIG. 21 illustrate the use of the secondary DNA colonies in the isolation and identification of novel and rare expressed genes.

Figure 1A:
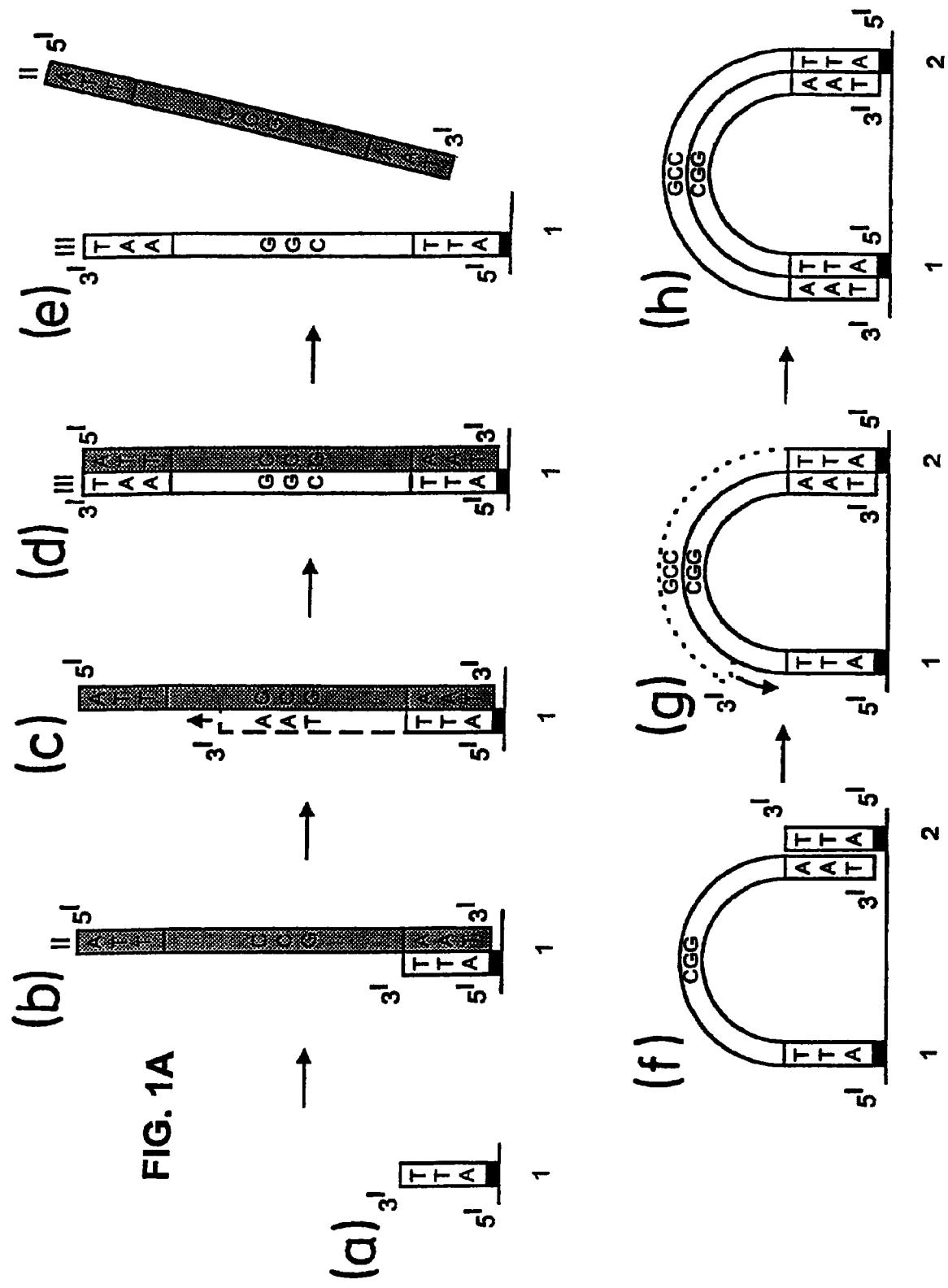
FIG. 1A and FIG. 1B illustrate a method for the simultaneous amplification and immobilisation of nucleic acid molecules using a single type of primer.

A) Scheme Showing the Simultaneous Amplification and Immobilisation of Nucleic Acid Molecules Using a Single Type of Primer Referring now to FIG. 1a), a surface is provided having attached thereto a plurality of primers (only one primer is shown for simplicity). Each primer (1) is attached to the surface by a linkage indicated by a dark block. This may be a covalent or a non-covalent linkage but should be sufficiently strong to keep a primer in place on the surface. The primers are shown having a short nucleotide sequence (5'-ATT). In practice however longer sequences would generally be provided.

Figure 1B:
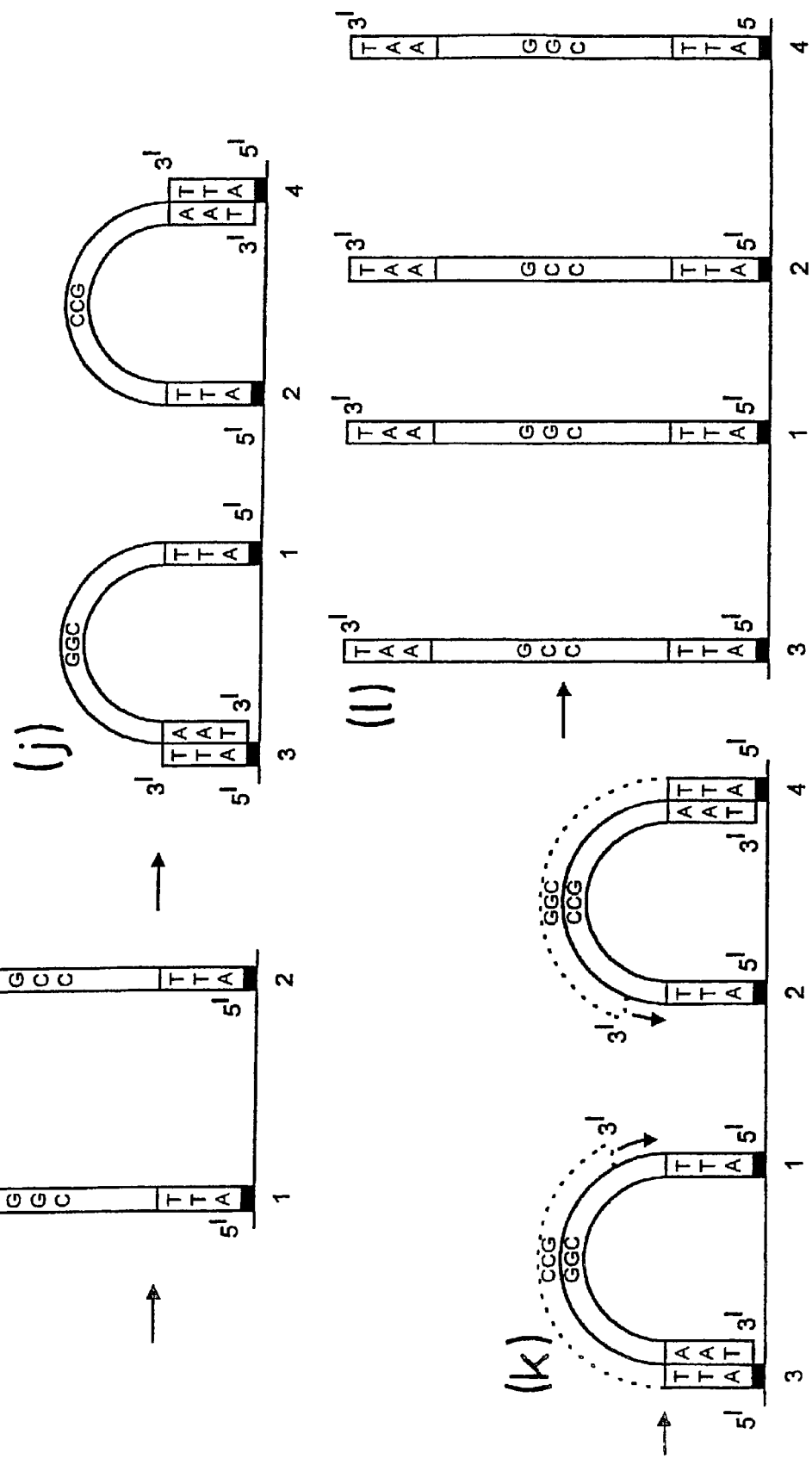

FIG. 1b) shows a target molecule (II) that has annealed to a primer. The target molecule comprises at its 3' end a sequence (5'-ATT) that is complementary to the primer sequence (5'-ATT). At its 5' end the target molecule comprises a sequence (5'-ATT) that is the same as the primer sequence (although exact identity is not required).

Between the two ends any sequence to be amplified (or the complement of any sequence to be amplified) can be provided. By way of example, part of the sequence to be amplified has been shown as 5'-CCG.

In FIG. 1c) primer extension is shown. Here a DNA polymerase is used together with dATP, dTTP, dGTP and dCTP to extend the primer (5'-ATT) from its 3' end, using the target molecule as a template.

When primer extension is complete, as shown in FIG. 1d), it can be seen that an extended immobilised strand (III) is provided that is complementary to the target molecule. The target molecule can then be separated from the extended immobilised strand (e.g. by heating, as shown in FIG. 1e)). This separation step frees the extended, immobilised strand so that it can then be used to initiate a subsequent round of primer extension, as shown in FIGS. 1f) and 1g)

Here the extended, immobilised strand bends over so that one end of that strand (having the terminal sequence 5'-AAT) anneals with another primer (2, 5'-ATT), as shown in FIG. 1f). That primer provides a 3' end from which primer extension can occur, this time using the extended, immobilised strand as a template. Primer extension is shown occurring in FIG. 1g) and is shown completed in FIG. 1h).

FIG. 1i) shows the two extended immobilised strands that were shown in FIG. 1h) after separation from one another (e.g. by heating). Each of these strands can then themselves be used as templates in further rounds of primer extension initiated from new primers (3 and 4), as shown in FIGS. 1j) and 1k). Four single stranded, immobilised strands can be provided after two rounds of amplification followed by a strand separation step (e.g. by heating as shown in FIG. 11). Two of these have sequences corresponding to the sequence of the target molecule originally used as a template. The other two have sequences complementary to the sequence of the target molecule originally used as a template. (In practice a given immobilised strand and its immobilised complement may anneal once.)

It will therefore be appreciated that a given sequence and its complement can be provided in equal numbers in immobilised form and can be substantially homogeneously distributed within a colony.

Further rounds of amplification beyond those shown in FIG. 1 can of course be performed so that colonies comprising large numbers of a given single stranded nucleic acid molecule and a complementary strand thereto can be provided. Only a single template need be used to initiate each colony, although, if desired, a template can be re-used to initiate several colonies.

It will be appreciated that the present invention allows very high densities of immobilised extended nucleic acid molecules to be provided. Within a colony each extended immobilised molecule will be located at a surface within one molecule length of another extended immobilised molecule. Thus position 3 shown in FIG. 11) is within one molecule length of position 1; position 1 is within one molecule length of position 2; and position 2 is within one molecule length of position 4.

FIG. 2 is provided to illustrate how colony growth can occur (using the method described with reference to FIG. 1 and to FIG. 6 or any other method of the present invention for providing immobilised nucleic acid molecules).

A flat plate is shown schematically in plan view having primers immobilised thereon in a square grid pattern (the primers are indicated by small dots). A regular grid is used solely for simplicity: in many real cases, the positions of the primers might indeed be less ordered or random.

At the position indicated by arrow X a template molecule has annealed to a primer and an initial bout of primer extension has occurred to provide an immobilised, extended nucleic acid strand. Following strand separation, an end of that strand becomes free to anneal to further primers so that additional immobilised, extended nucleic acid strands can be produced. This is shown having occurred sequentially at positions indicated by the letter Y. For simplicity, the primer chosen for annealing is positioned next to the primer carrying the nucleic acid strand: in real cases, the nucleic acid strand could anneal with a primer which is not its next nearest neighbour. However, this primer will obviously be within a distance equal to the length of the nucleic acid strand.

It will be appreciated that annealing at only one (rather than at all) of these positions is required for colony cell growth to occur.

After immobilised, extended, single-stranded nucleic acid molecules have been provided at the positions indicated by letter Y, the resultant molecules can themselves anneal to other primers and the process can be continued to provide a colony comprising a large number of immobilised nucleic acid molecules in a relatively small area.

FIG. 3 shows a simplified version of the annealing, elongation and denaturing cycle. It also depicts the typical observations that can be made, as can be seen on the examples shown in FIGS. 4 and 6. The simultaneous amplification and immobilisation of nucleic acids using solid phase primers has been successfully achieved using the procedure described in Examples 1, 2 and 3 below:

EXAMPLE 1

Oligonucleotides, phosphorylated at their 5'-termini (Microsynth GmbH, Switzerland), were grafted onto Nucleolink plastic microtitre wells (Nunc, Roskilde, Denmark). The sequence of the oligonucleotide p57 corresponds to the sequence 51-TTTTTTCACCAACCCAAACCAAC-CCAAACC (SEQ ID NO:1) and p58 corresponds to the sequence 51-TTTTTTAGAAGGAGAAGGAAAGG-GAAAGGG (SEQ ID NO:2). Microtitre wells with p57 or p58 were prepared as follows. In each Nucleolink well, 30 µl of a 160 nM solution of the oligonucleotide in 10 mM 1-methyl-imidazole (pH 7.0) (Sigma Chemicals, St. Louis, Mo.) was added. To each well, 10 µl of 40 mM 1-ethyl-3-(3dimethylaminopropyl)-carbodiimide (pH 7.0) (Sigma Chemicals) in 10 mM 1-methyl-imidazole, was added to the solution of oligonucleotides. The wells were then sealed and incubated at 50° C. overnight. After the incubation, wells were rinsed twice with 200 µl of RS (0.4N NaOH, 0.25% Tween 20 (Fluka Chemicals, Switzerland)), incubated 15 minutes with 200 pl RS, washed twice with 200 µl RS and twice with 200 µl TNT (100 mM TrisHCl pH7.5, 150 mM NaCl, 0.1% Tween 20). Tubes were dried at 50° C. and were stored in a sealed plastic bag at 4° C.

Colony generation was initiated in each well with 15 µl of priming mix; 1 nanogram template DNA (where the template DNA began with the sequence 51-AGAAGGAGAAG-GAAAGGGAAAGGG (SEQ ID NO:3) and terminated at the 31-end with the sequence CCCTTTCCCTTTCCTTCTCCT-TCT-3' (SEQ ID NO:4)), the four dNTPs (0.2 mM), 0.1% BSA (bovine serum albumin, Boehringer-Mannheim, Germany), 0.1% Tween 20, 8% DMSO (dimethylsulfoxide, Fluka Chemicals, Switzerland), 1× Amplitaq PCR buffer and 0.025 units/µl of AmpliTaq DNA polymerase (Perkin Elmer, Foster City, Calif.). The priming reaction was a single round of PCR under the following conditions; 94° C. for 4 minutes, 60° C. for 30 seconds and 72° C. for 45 seconds in a thermocycler (PTC 200, MJ Research, Watertown, Mass.). Then 100 µl TE buffer (10 mM trisHCl, pH 7.5, lmM EDTA) was used in three successive one minute long washes at 94° C. The DNA colonies were then formed by adding to each well, 20 µl of polymerisation mix, which was identical to the priming mix but lacking the template DNA. The wells were then placed in the PTC 200 thermocycler and colony growing was performed by incubating the sealed wells 4 minutes at 94° C. and cycling for 50 repetitions the following conditions: 94° C. for 45 seconds, 65° C. for 2 minutes, 72° C. for 45 seconds. After completion of this program, the wells were kept at 8° C. until further use.

A 640 base pair fragment corresponding to the central sequence of the template (but not including the 5'-AGAAG-GAGAAGGAAAGGGAAAGGG (SEQ ID NO:3) sequence) was amplified by PCR. The isolated fragment was labeled with biotin-$N^4$-dCTP (NEN Life Sciences, Boston, Mass.) and a trace of [$\alpha$-$^{32}$P]dCTP (Amersham, UK) using the Prime-it II labeling kit (Stratagene, San Diego, Calif.) to generate a biotinylated probe.

The biotinylated probe was diluted in to a concentration of 2.5 nM in EasyHyb (Boehringer-Mannheim, Germany) and 15 µl was hybridized to each sample with the following temperature scheme (PTC 200 thermocycler): 94° C. for 5 minutes, followed by 500 steps of 0.1° C. decrease in temperature every 12 seconds (in other words, the temperature is decreased down to 45° C. in 100 minutes). The samples are then washed as follows; 1 time with 2×SSC/0.1% SDS (2×SSC; 0.3M NaCl/0.03M sodium citrate pH 7.0/0.001 mg/ml sodium dodecyl sulfate) at room temperature, once with 2×SSC/0.1% SDS at 37° C. and once with 0.2×SSC/ 0.1% SDS at 50° C. The wells are then incubated for 30 minutes with 50 µl of red fluorescent, Neutravidin-coated, 40 nm FluoSpheres® (580 nm excitation and 605 nm emission, Molecular Probes Inc., Eugene, Oreg.) in TNT/0.1% BSA. (The solution of microspheres is made from a dilution of 2 µl of the stock solution of microspheres into 1 ml of TNT/0.1% BSA, which is then sonicated for 5 minutes in a 50 W ultrasound water-bath (Elgasonic, Switzerland), followed by filtration through a 0.22 µm filter (Millex GV4). The wells are then counted (Cherenkov) on a Microbeta plate scintillation counter (WALLAC, Turku, Finland).

Excess FluoSpheres® are removed by washing for 30 min in TNT/0.1% BSA at room temperature. Images of the stained samples are observed using a 20× objective on an inverted microscope (Axiovert S100TV, Carl Zeiss AG, Oberkochen, Germany) equipped with a Micromax 512×768 CCD camera (Princeton instruments, Trenton, N.J.) through a XF43 filter set (PB546/FT580/LP590, Omega Optical, Brattleboro, Vt.) with a 5 second exposure.

Figure 4:
FIG. 4 is an example of DNA colonies formed by amplification of a specific template with single primers grafted onto a surface.
Figure 5:
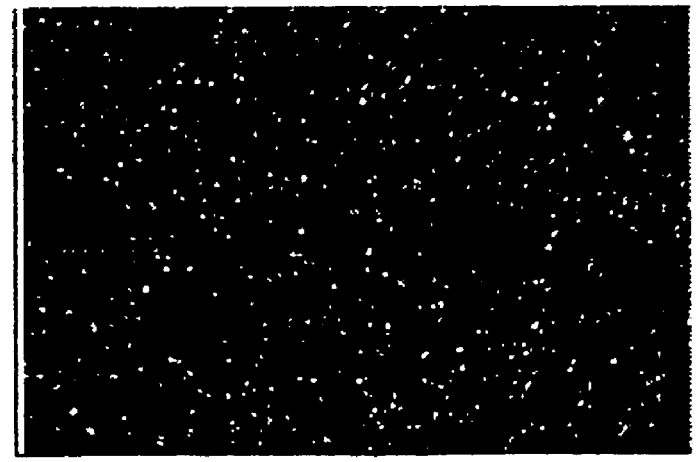
FIG. 5 is an example of DNA colonies formed by amplification of a specific template with single primers grafted onto a surface.

FIGS. 4 and 5 show the hybridisation results for colony generation on tubes functionalised with either, FIG. 4 oligonucleotide p57 or FIG. 5 oligonucleotide p58. The control reaction shows very few fluorescent spots, since the sequence of the flanking regions on the template do not correspond to the primer sequences grafted onto the well. In contrast, FIG. 5 shows the number of fluorescent spots detected when the primers grafted to the wells match the flanking sequences on the initiating DNA template. Calculating the number of fluorescent spots detected and taking into consideration the magnification, we can estimate that there are between 3 and 5×10$^7$ colonies/cm$^2$. The photos are generated by the program, Winview 1.6.2 (Princeton Instruments, Trenton, N.J.) with backgrounds and intensities normalised to the same values.

Figure 6A:
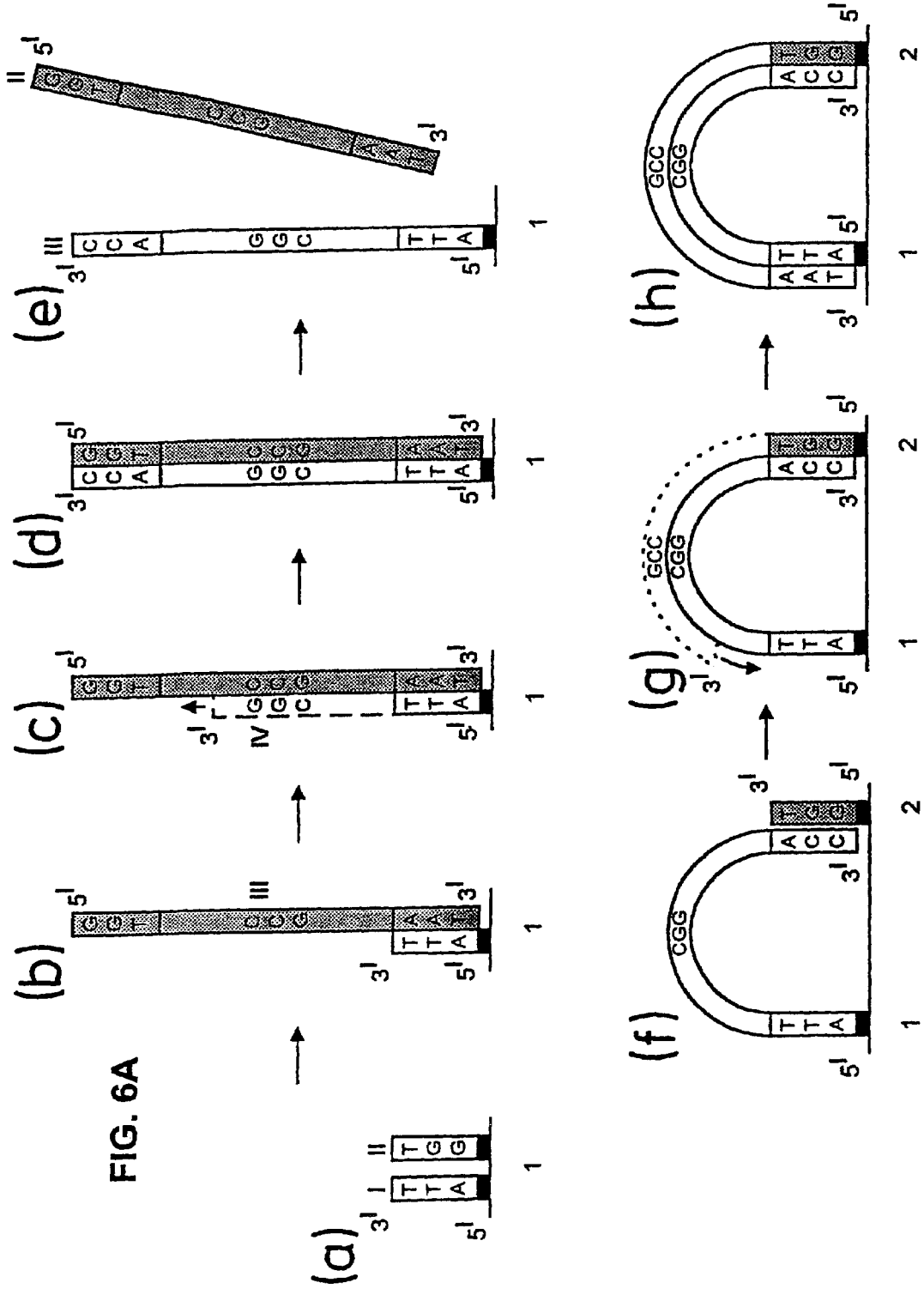
FIGS. 6A and FIG. 6B illustrate a method for the simultaneous amplification and immobilisation of nucleic acid molecules using two types of primer.
Figure 6B:
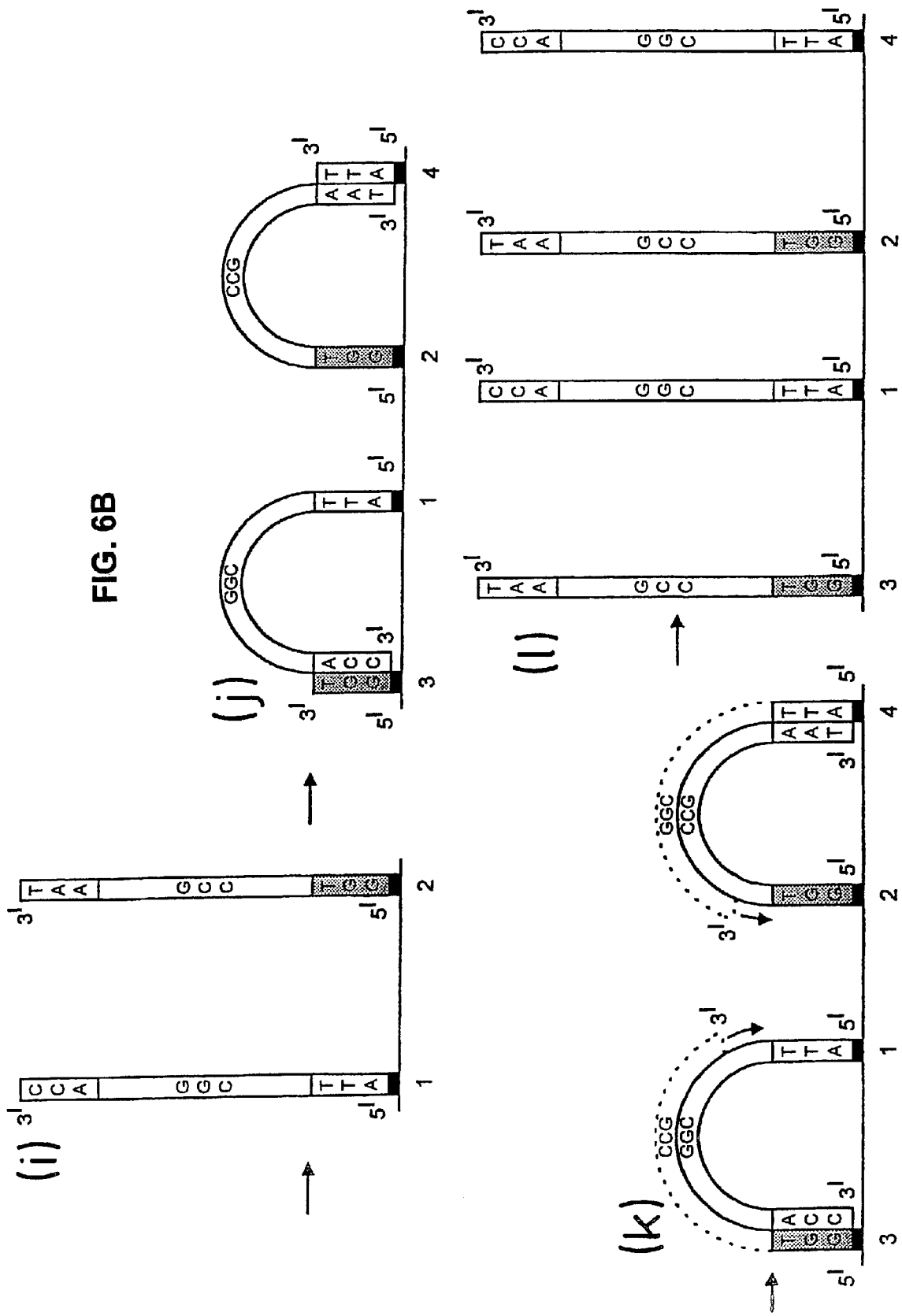

B) Scheme Showing the Simultaneous Amplification and Immobilisation of Nucleic Acid Molecules Using Two Different Types of Primer Referring now to FIGS. 6A and 6B, another embodiment of the present invention is illustrated. Here two different immobilised primers are used to provide primer extension.

In this embodiment the target molecule shown is provided with a nucleotide sequence at its 3' end (AAT-3') that is complementary to the sequence of a first primer, (5'-ATT, I), which is grafted on the surface, so-that annealing with that primer can occur. The sequence (5'-GGT) at the 5' end of the target molecule, III, corresponds to the sequence (5'-GGT) of a second primer, II, which is also grafted to the surface, so that the sequence which is complementary to the sequence at the 5' end can anneal with that said second primer. Generally said complementary sequence (5'-ACC) is chosen so that it will not anneal with the first primer (5'-ATT). Unlike the situation described in section A, once the 3' end of a newly synthesised strand anneals to a primer on the surface, it will have to find a primer whose sequence is different from the sequence it carries at its 5' end (see the difference between FIG. 1A, (f) and FIG. 6A, (f)).

The embodiment shown in FIGS. 6A and 6B have an advantage over the embodiment illustrated in FIG. 1 since the possibility of one end of a single stranded target molecule annealing with another end of the same molecule in solution can be avoided and therefore amplification can proceed further. The possibility of annealing occurring between both ends of an immobilised complement to a target molecule can also be avoided.

EXAMPLE 2

A mix of two oligonucleotides which are phosphorylated at the 5'-end (Microsynth GmbH, Balgach, Switzerland) have been grafted on 96 well Nucleolink plates (Nunc, Denmark) as recommended by the manufacturer. The resulting plates has been stored dry at 4° C. The sequence of the primer, P1, was 5'-GCGCGTAATACGACTCACTA (SEQ ID NO:5), the sequence of the other primer, P2, was 5'-CGCAATTAAC-CCTCACTAAA (SEQ ID NO:6). These plates are specially formulated by Nunc, allowing the covalent grafting of 51 phosphorylated DNA fragments through a standard procedure.

A template has been cloned in a vector (pBlueScript Skminus, Stratagene Inc, San Diego, Calif.) with the appropriate DNA sequence at the cloning site (i.e., corresponding to P1 and P2 at position 621 and 794 respectively), and 174 bp long linear double stranded DNA template has been obtained by PCR amplification, using P1 and P2. The template PCR product has been purified on Qiagen Qia-quick columns (Qiagen GmbH, Hilden, Germany) in order to remove the nucleotides and the primers used during the PCR amplification.

The purified template (in 50 µl solution containing 1×PCR buffer (Perkin Elmer, Foster City, Calif.) with the four deoxyribonucleoside triphosphates (dNTPs) at 0.2 mM, (Pharmacia, Uppsala, Sweden) and 2.5 units of AmpliTaq Gold DNA polymerase (Perkin Elmer, Foster City, Calif.)) has been spread on the support, i.e. on the Nucleolink plates grafted with P1 and P2 (the plates have been rinsed with a solution containing 100 mM TRIS-HCl (pH 7.5), 150 mM NaCl and 0.1% Tween 20 (Fluka, Switzerland) at room temperature for 15 min). This solution has been incubated at 93° C. for 9 minutes to activate the DNA polymerase and then 60 cycles (94° C./30 sec., 48° C./30 sec., 72° C./30 sec.) have been performed on a PTC 200 thermocycler. Several different concentrations of PCR template have been tested (approximately 1, 0.5, 0.25, 0.125, 0.0625 ng/µl) and for each sample a control reaction carried out without Taq polymerase has been performed (same conditions as above but without DNA polymerase).

Each sample has been stained with YO—PRO (Molecular Probes, Portland Oreg.), a highly sensitive stain for double stranded DNA. The resulting products have been observed on a confocal microscope using a 40× objective (LSM 410, Carl Zeiss AG, Oberkochen, Germany) with appropriate excitation (an 488 argon laser) and detection filters (510 low pass filter) (note: the bottom of each well is flat and allows observation with an inverted fluorescence microscope).

In FIG. 7, the control well (without added DNA template, panel a) shows only rare objects which can be observed on a blank surface (these objects were useful at this stage for reporting that the focus was correct). These objects have an irregular shape, are 20 to 100 micro-meters in size and have a thickness much larger than the field depth of the observation. In a well where DNA polymerase was present (FIG. 7, panel ii), in addition to the objects of irregular shape observed in the control well, a great number of fluorescent spots can be observed. They present a circular shape, they are 1 to 5 micro meters in size and do not span the field of view. The number of spots depends on the concentration of the template used for initiating colony formation. From the observed size of the colonies, one can estimate that more than 10,000 distinct colonies can be arrayed within 1 mm² of support.

EXAMPLE 3

Oligonucleotides (Microsynth GmbH, Switzerland) were grafted onto Nucleolink wells (Nunc, Denmark).

Oligonucleotide P1 corresponds to the sequence 5'-TTTTTTCTCACTATAGGGCGAATTGG (SEQ ID NO:7) and oligonucleotide P2 corresponds to 5'-TTTTTTCT-CACTAAAGGGAACAAAAGCTGG (SEQ ID NO:8). In each Nucleolink well, a 45 µl of 10 mM 1-methyl-imidazole (pH 7.0) (Sigma Chemicals, St. Louis, M.) solution containing 360 fmol of P1 and 360 fmol of P2 was added. To each well, 15 gl of 40 mM 1-ethyl-3-(3-dinethylaminopropyl)-carbodiimide (pH 7.0) (Sigma Chemicals) in 10 mm 1-methyl-imidazole, was added to the solution of oligonucleotides. The wells were then sealed and incubated at 50° C. for 16 hours. After the incubation, wells have been rinsed twice with 200 µl of RS (0.4N NaOH, 0.25% Tween 20), incubated 15 minutes with 200 µl RS, washed twice with 200 pl RS, and twice with 200 µl TNT (100 mM Tris/HCl pH7.5, 150 mM NaCl, 0.1% Tween 20), before they are put to dry at 50° C. in an oven. The dried tubes were stored in a sealed plastic bag at 4° C.

Colony growing was initiated in each well with 15 µl of initiation mix (1×PCR buffer, 0.2 mM dNTPs and 0.75 units of AmpliTaq Gold DNA polymerase, 20 nanograms of template DNA, where the template DNA was either S1 DNA or S2 DNA or a mixture of different ratios of S1 DNA and S2 DNA, as indicated in discussion to FIG. 6B. S1 and S2 are 704 base pair and 658 bp fragments, respectively, which have been cloned into pBlueScript Skminus plasmids and subsequently amplified through a PCR using P1 and P2 as primers. The fragments were purified on Qiagen Qia-quick columns (QIAGEN GmbH, Germany) in order to remove the nucleotides and the primers.

Each well was sealed with Cycleseal™ (Robbins Scientific Corp., Sunnyvale, Calif.), and incubated at 93° C. for 9 minutes, 65° C. for 5 minutes and 72° C. for 2 minutes and back to 93° C. Then 200 µl TNT solution was used in three successive one minute long washes at 93° C. The initiation mix was then replaced by 15 µl growing mix (same as initiation mix, but without template. DNA), and growing was performed by incubating the sealed wells 9 minutes at 93° C. and repeating 40 times the following conditions: 93° C. for 45 seconds, 65° C. for 3 minutes, 72° C. for 2 minutes. After completion of this program, the wells were kept at 6° C. until further use. The temperature control was performed in a PTC 200 thermo-cycler, using the silicon pad provided in the Nucleolink kit and the heated (104° C.) lid of the PTC 200.

A 640 base pair fragment corresponding to the central sequence of the S1 fragment, but not including the P1 or P2 sequence was amplified by PCR as previously described. The probe was labelled with biotin-16-dUTP (Boehringer-Mannheim, Germany) using the Prime-it II random primer labelling kit (Stratagene, San Diego, Calif.) according to the manufacturers instructions.

The biotinylated probes were hybridized to the samples in EasyHyb buffer (Boehringer-Mannheim, Germany), using the following temperature scheme (in the PTC 200 thermocycler): 94° C. for 5 minutes, followed by 68 steps of 0.5° C. decrease in temperature every 30 seconds (in other words, the temperature is decreased down to 60° C. in 34 minutes), using sealed wells. The samples are then washed 3 times with 200 µl of TNT at room temperature. The wells are then incubated for 30 minutes with 50 µl TNT containing 0.1 mg/ml BSA. Then the wells are incubated 5 minutes with 15 µl of solution of red fluorescent, Neutravidin-coated, 40 nm FluoSpheres® (580 nm excitation and 605 nm emission, Molecular Probes, Portland, Oreg.). The solution of microspheres is made of 2 µl of the stock solution of microspheres, which have been sonicated for 5 minutes in a 50 W ultra-sound water-bath (Elgasonic, Bienne, Switzerland), diluted in 1 ml of TNT solution containing 0.1 mg/ml BSA and filtered with Millex GV4 0.22 µm pore size filter (Millipore, Bedford, Mass.).

The stained samples are observed using an inverted Axiovert 10 microscope using a 20× objective (Carl Zeiss AG, Oberkochen, Germany) equipped with a Micromax 512×768

CCD camera (Princeton Instruments, Trenton, N.J.), using a XF43 filter set (PB546/FT580/LP590, Omega Optical, Brattleboro, Vt.), and 10 seconds of light collection. The files are converted to TIFF format and processed in the suitable software (PhotoPaint, Corel Corp., Ottawa, Canada). The processing consisted in inversion and linear contrast enhancement, in order to provide a picture suitable for black and white print-out on a laser printer.

The FIG. 8 shows the results for 3 different ratios of the S1/S2 templates used in the initiating reaction: i) the S1/S2 is 1/0, many spots can be observed, ii) the S1/S2 is 1/10, and the number of spots is approximately 1/10 of the number of spots which can be observed in the i) image, as expected, and iii) the S1/S2 is 0/1, and only a few rare spots can be seen.

Figure 9A:
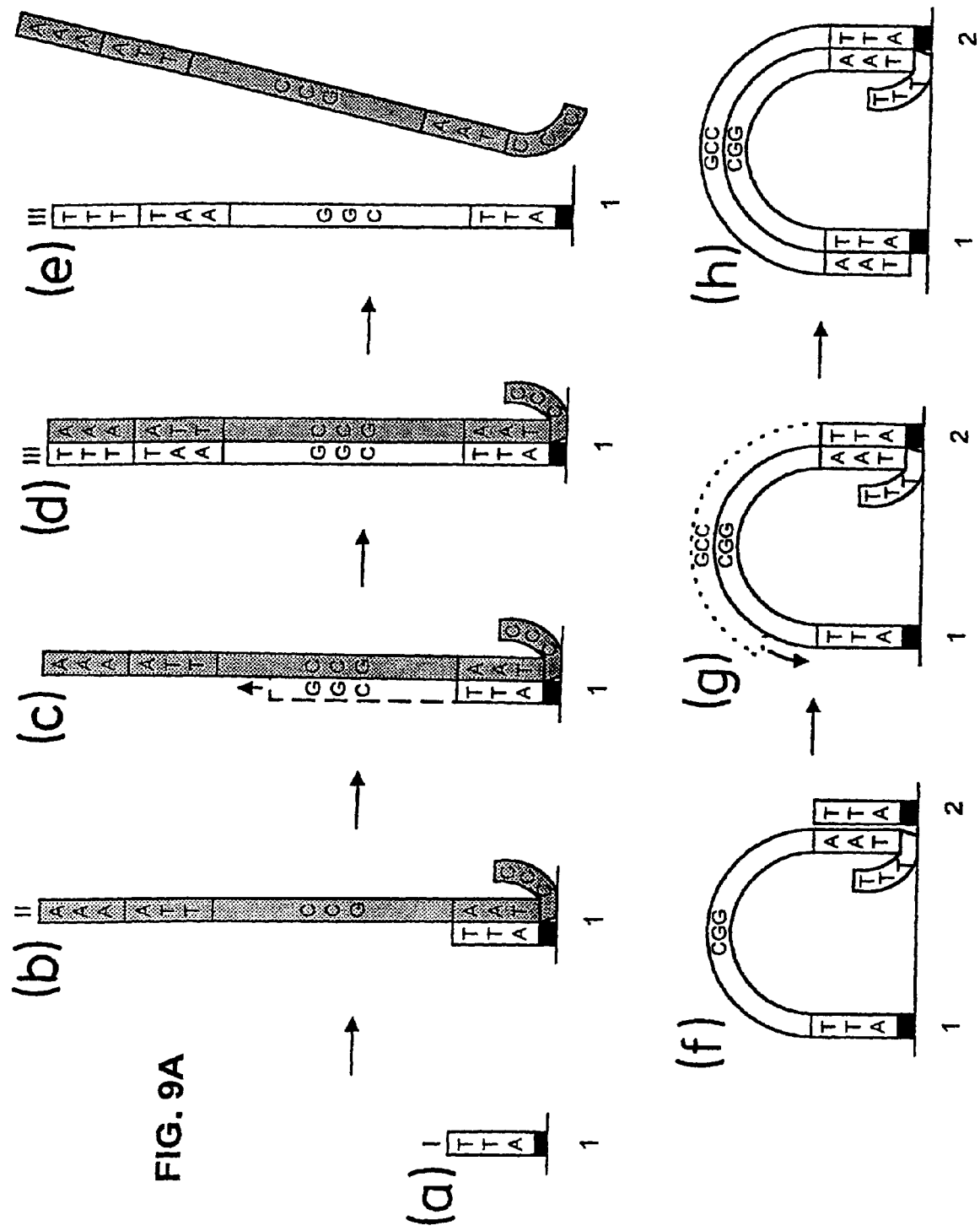
FIG. 9A and FIG. 9B illustrate a method of the simultaneous amplification and immobilisation of nucleic acid molecules when a target molecule is used as a template having internal sequences that anneal with primers.
Figure 9B:
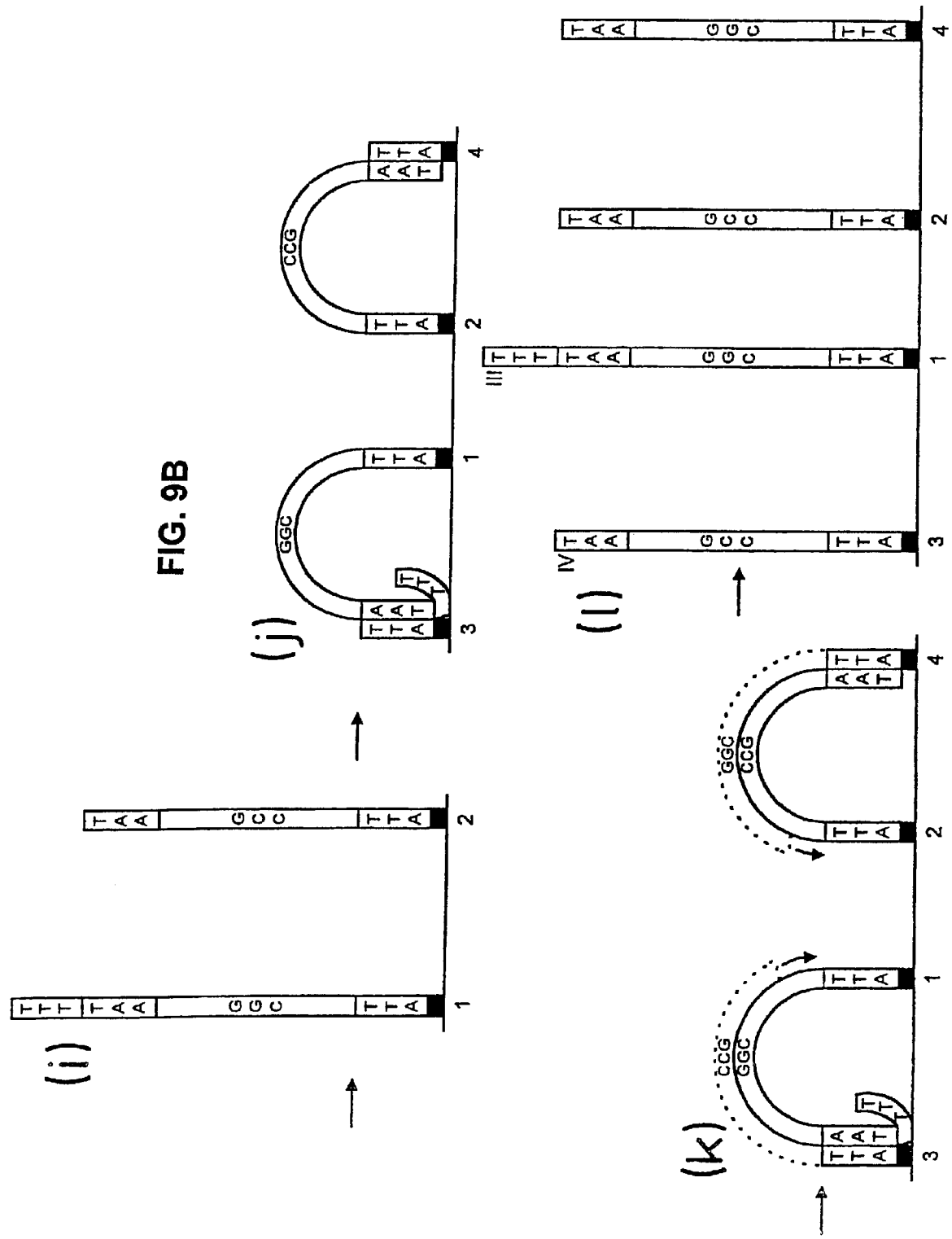

C Scheme Showing Simultaneous Amplification and Immobilisation of Nucleic Acid Molecules when the Target Molecule Contains Internal Sequences Complementary to the Immobilised Primers FIGS. 9A and 9B are provided to show that the sequences shown at the 5' and 3' ends of the target molecule illustrated in FIGS. 1A and 1B and FIGS. 6A and 6B need not be located at the ends of a target molecule.

A target nucleic acid molecule (II) may have a sequence at each (or either) end that is neither involved in annealing with a primer nor in acting as a template to provide a complementary sequence that anneals with a primer (sequence 5'-AAA and sequence 5'-CCC). One of the internal sequences (5'-AAT) is used as a template to synthesise a complementary sequence, III, thereto (5'-TTT), as is clear from FIGS. 9A, (a) to (e).

The sequence 5'-TTT is not however itself used to provide a sequence complementary thereto, as is clear from FIGS. 9A, (f) to (h) and FIG. 9B, (i) to (k). It can be seen from FIG. 9B, (l) that only one of the four immobilised strands shown after two rounds of primer extension and a strand separation step comprises the additional sequence 5'-TTT and that no strand comprising a complementary sequence (5'-AAA) to this sequence is present (i.e. only one strand significantly larger than the others is present). After several rounds of amplification the strand comprising the sequence 5'-TTT will represent an insignificant proportion of the total number of extended, immobilised nucleic acid molecules present.

D) Using Nucleic Acid Strands Present in Colonies to Synthesise Additional Copies of Nucleic Acid Strands Amplified, single stranded nucleic acid molecules present in colonies provided by the present invention can themselves be used as templates to synthesise additional nucleic acid strands.

FIGS. 10A and 10B illustrate one method of synthesising additional nucleic acids using immobilised nucleic acids as a starting point.

Colonies will usually comprise both a given nucleic acid strand and its complement in immobilised form (FIG. 10A, (a)). Thus they can be used to provide additional copies not only of a given nucleic acid strand but also of its complement.

One way of doing this is to provide one or more primers (primers TTA and TGG) in solution that anneal to amplified, immobilised nucleic acid strands present in colonies (FIG. 10A, (c)) provided by the present invention. (These primers may be the same as primers initially used to provide the immobilised colonies, apart from being provided in free rather than immobilised form.) The original DNA colony is denatured by heat to it single-stranded form (FIG. 10A, (b)), allowing primers TTA and TGG to anneal to the available 3' end of each DNA strand. Primer extension, using AmpliTaq DNA polymerase and the four deoxyribonucleoside triphosphates (labeled or unlabeled) can then be used to synthesise complementary strands to immobilised nucleic acid strands or at least to parts thereof (step (iii)).

Once newly formed strands (FIG. 10B, (d)) have been synthesised by the process described above, they can be separated from the immobilised strands to which they are hybridised (e.g. by heating). The process can then be repeated if desired using the PCR reaction, to provide large number of such strands in solution (FIG. 10B, (e)).

Strands synthesised in this manner, after separation from the immobilised strands, can, if desired, be annealed to one another (i.e. a given strand and its complement can anneal) to provide double-stranded nucleic acid molecules in solution. Alternatively they can be separated from one another to provide homogenous populations of single-stranded nucleic acid molecules in solution.

It should also be noted that once single-stranded molecules are provided in solution they can be used as templates for PCR (or reverse PCR). Therefore it is not essential to continue to use the immobilised nucleic acid strands to obtain further amplification of given strands or complementary strands thereto.

It should be noted that where a plurality of colonies are provided and nucleic acid strands in different colonies have different sequences, it is possible to select only certain colonies for use as templates in the synthesis of additional nucleic acid molecules. This can be done by using primers for primer extension that are specific for molecules present in selected colonies.

Alternatively primers can be provided to allow several or all of the colonies to be used as templates. Such primers may be a mixture of many different primers (e.g. a mixture of all of the primers originally used to provide all of the colonies, but with the primers being provided in solution rather than in immobilised form).

EXAMPLE 4

Oligonucleotides (Microsynth GmbH Balgach, Switzerland) were grafted onto Nucleolink wells (Nunc, Denmark). Oligonucleotide P1 corresponds to the sequence 5'-TTTTTTTTTCACCAACCCAAACCAACCCAAACC (SEQ ID NO:9) and oligonucleotide P2 corresponds to 5'TTTTTTTTTAGAAGGAGAAGGAAAGGGAAAGGG (SEQ ID NO:10). In each Nucleolink well, a 45 µl of 10 mM 1-methyl-imidazole (pH 7.0) (Sigma Chemicals) solution containing 360 fmol of P1 and 360 fmol of P2 was added. To each well, 15 µl of 40 mM 1-ethyl-3-(3-dimethylaminopropyl)-carbodiimide (pH 7.0) (Sigma Chemicals) in 10 mM 1-methyl-imidazole, was added to the solution of oligonucleotides. The wells were then sealed and incubated at 50° C. for 16 hours. After the incubation, wells have been rinsed twice with 200 µl of RS (0.4N NaOH, 0.25% Tween 20), incubated 15 minutes with 200 µl RS, washed twice with 200 µl RS, and twice with 200 µl TNT (100 mM Tris/HCl pH7.5, 150 mM NaCl, 0.1% Tween 20), before they are put to dry at 50° C. in an oven. The dried tubes were stored in a sealed plastic bag at 4° C.

Colony growing was initiated in each well with 15 µl of initiation mix (1×PCR buffer, 0.2 mM dNTPs and 0.75 units of AmpliTaq DNA polymerase, 20 nanograms of template DNA, where the template DNA was either S1 DNA or S2 DNA or a 1/1 mixture of S1 DNA and S2 DNA, as indicated in discussion to Example 3. S1 and S2 are 658 base pair and 704 b.p. fragments, respectively, which have been prepared as described in EXAMPLE 3.

Each well was sealed with Cycleseal™ (Robbins Scientific Corp., Sunnyvale, Calif.) and incubated at 93° C. for 9 minutes, 65° C. for 5 minutes and 72° C. for 2 minutes and back to 93° C. Then 200 μl TNT solution was used in three successive one minute long washes at 93° C. The initiation mix was then replaced by 15 μl growing mix (same as initiation mix, but without template DNA) and growing was performed by incubating the sealed wells 9 minutes at 93° C. and repeating 40 times the following conditions: 93° C. for 45 seconds, 65° C. for 3 minutes, 72° C. for 2 minutes. After completion of this program, the wells were kept at 6° C. until further use. The temperature control was performed in a PTC 200 thermocycler.

Different treatments where applied to 6 sets (A, B, C, D, E and F) of 3 wells (1, 2, 3), one prepared with template S1, one with template S1 and template S2 and one prepared with template S2 alone (yielding A1, A2, A3, . . . , F1, F2, F3). The set A was left untreated, set B has been incubated for 10 minutes with BAL-31 exonuclease (New England Biolabs, Beverly, Mass.) at 37° C. in BAL-31 buffer (BAL-31 essentially digests double stranded DNA which has both ends free), set C has been incubated for 10 minutes with S1 nuclease (Pharmacia, Uppsala, Sweden) at 37° C. in S1 buffer (S1 nuclease essentially digests single stranded DNA), set D, E and F have been incubated with both BAL-31 and S1 nucleases. Reactions were stopped by rinsing the wells with TNT buffer.

PCR (25 cycles, 30 sec. at 94° C., 45 sec. at 60° C., 45 sec. at 72° C.) has been performed in the Nucleolink wells with 0.25 μM primers P70 (5'-CACCAACCCAAACCAAC-CCAAACCACGACTCACTATAGGGCGAA (SEQ ID NO:11)) and P71 (5'-AGAAGGAGAAGGAAAGG-GAAAGGGTAAAGGGAACAAAAGCTGGA (SEQ ID NO:12)) in solution in sets A. B, C and D. P70 and P71 are suited for the amplification of both S1 and S2, since primer P70 contains the sequence of primer P1 and p71 contains P2. In the set E wells, PCR has been performed with a set of forward (P150, 5'-GGTGCTGGTCCTCAGTCTGT (SEQ ID NO:13)) and reverse (P151, 5'-CCCGCTTACCAGTTTC-CATT (SEQ ID NO:14)) primers which are within S1 and not within S2 so as to produce a 321 by PCR product, and in the set F wells, PCR has been performed with a set of forward (P152, 5'-CTGGCCTTATCCCTAACAGC (SEQ ID NO:15)) and reverse (P153, 5'-CGATCTTGGCTCATCACAAT (SEQ ID NO:16)) primers which are within S2 and not within S1 so as to produce a 390by PCR product. For each of the 18 PCR reactions, 3 μl of solution have been used for gel electrophoresis on 1% agarose in presence of 0.1 μg/ml ethidium-bromide. The pictures of the gels are presented in FIGS. 11A and 11B. These pictures show that DNA in the colonies is protected from exonuclease digestion (sets B, C and D as compared to set A), and that both S1 and S2 can be recovered either simultaneously using P1 and P2 (sets A, B, C and D) or specifically (set E and F). In set E and F, where the shorter PCR products are more efficiently amplified than the longer PCR products in sets A, B, C, D, a cross-contamination between the S1 and S2 templates is detectable (see lane E2 and F1).

E) Provision of Secondary Colonies

It is also possible to modify initially formed colonies to provide different colonies (i.e. to provide colonies comprising immobilised nucleic acid molecules with different sequences from those molecules present in the initially formed colonies). Here, the initially formed colonies are referred to as "primary colonies" and the later formed colonies as "secondary colonies". A preliminary procedure is necessary to turn the primary colonies into "secondary primers" which will be suitable for secondary colony generation.

FIGS. 12A, 12B and 12C shows how 'secondary primers' are generated using existing primary colonies. As a starting point, the primary colony (FIG. 12A, (a)) is left in the fully hybridised, double-stranded form. A single-strand specific DNA exonuclease might be used to remove all primers which have not been elongated. One could also choose to cap all free 3'-OH ends of primers with dideoxyribonucleotide triphosphates using a DNA terminal transferase (step (i), FIG. 12A, (b)).

Secondly and independently, the DNA molecules forming the colonies can be cleaved by using endonucleases. For example, a restriction enzyme that recognises a specific site within the colony (depicted by the IRE' arrow in FIG. 12B (c)) and cleaves the DNA colony (step (ii), FIG. 12B). If desired, the enzymatically cleaved colony (FIG. 12B, (d)) can then be partially digested with a 3' to 51 double-strand specific exonuclease (e.g. E. coli exonuclease III, depicted by 'N', step (iii), FIG. 12B, (d)). In any case, the secondary primers are available after denaturation (e.g., by heat) and washing (FIG. 12B, (e)).

Alternatively, the double stranded DNA forming the colonies (FIG. 12C, (f)) can be digested with the double-strand specific 3'-5' exonuclease, which digest only one strand of double stranded DNA. An important case is when the exonuclease digests only a few bases of the DNA molecule before being released in solution, and when digestion can proceed when another enzyme binds to the DNA molecule (FIG. 12C, (g)). In this case the exonuclease digestion will proceed until there remain only single stranded molecules which, on average, are half the length of the starting material, and are without any complementary parts (which could form partial duplexes) remaining in the single stranded molecules in a colony (FIG. 12C(h)).

In all cases, these treatments result in single-stranded fragments grafted onto a support which correspond to the sequence of the original template and that can be used for new DNA colony growing if an appropriate new template is provided for colony initiation (FIGS. 12B, (e) and FIG. 12C, (h)).

The result of such a treatment, thus a support holding secondary primers, will be referred to as a "support for secondary colony growing". Templates useful for secondary colony growing may include molecules having known sequences (or complements of such sequences). Alternatively templates may be derived from unsequenced molecules (e.g. random fragments). In either event the templates should be provided with one or more regions for annealing with nucleic acid strands present in the primary colonies.

FIGS. 13A and 13B show how a secondary colony can be generated when an appropriate template (TP, FIG. 13A, (a)) is provided for a second round of DNA colony generation on a support for secondary colony growing, holding secondary primers. In this example, treatment of the primary colony as described above has generated the secondary primers, SP1 and SP2 (FIG. 13A, (a)). The template TP, will hybridise to its complementary secondary primer, SP1, and following an extension reaction using a DNA polymerase as described, will be extended as depicted (FIG. 13A, (b)). Following a denaturing (step ii), reannealing (step iii) and DNA polymerase (step iv) cycle, a replica of the original primary colony will be formed (FIG. 13B, (e)).

The maximum size of a secondary colony provided by this embodiment of the present invention is restricted by the size of the primary colony onto which it grows. Several secondary growing processes can be used sequentially to create colonies for specific applications (i.e. a first colony can be replaced with a second colony, the second colony can be replaced with a third colony, etc.)

F) Provision of Extended Primers

FIGS. 14A and 14B show how extended primers can be generated on an array of oligonucleotides. The same procedure could be applied to a support covered with colonies or secondary primers as described in section E.

In FIG. 14A, (a) a support is provided having a plurality of immobilised primers shown thereon. Different immobilised primers are shown present in different regions of the support (represented by squares). Primers having the sequence 5'-AAA are present in one square and primers having the sequence 5'-GGG are present in another square.

FIGS. 14A, (b) and FIG. 14B, (c) and (d) show how the initial primers present (initial primers) are modified to give different primers (extended primers). In this example, those initial primers having the sequence 5'-AAA are modified to produce two different types of extended primers, having the sequences 5'-AAAGCC and 5'-AAATAC respectively. This is achieved by the hybridisation of oligonucleotide templates, 5'-GTATTT and 5'-GGCTTT to the primary primers immobilised on the surface (FIG. 14A, (b)), followed by DNA polymerase reaction. Those initial primers having the sequence 5'-GGG are modified to produce two different types of extended primers, having the sequences 5'-GGGTAT and 5'-GGGTAA (FIG. 14B, (d)) in a similar manner.

The technique of producing extended primers is useful for transforming immobilised oligonucleotides provided on a DNA chip or other surface into immobilised primers useful in amplifying a particular target nucleic acid sequence and/or in amplifying a complementary strand thereto.

G) Preparation of Nucleic Acid Fragments

Apparatuses of the present invention can be used for various procedures some of which will be described later on. Nucleic acid fragments for use in colony generation may be prepared differently for the different procedures (referred to herein as "prepared nucleic acids"). Various preparation procedures are described below:

(i) Preparation of Random DNA Fragments

Here is described a method to prepare DNA originating from one biological sample (or from a plurality of samples) for amplification in the case where it is not necessary to keep track of the origin of the DNA when it is incorporated within a colony.

The DNA of interest is first extracted from the biological sample and cut randomly into "small" pieces (e.g., 50 to 10,000 bases long, but preferentially 500 to 1000 base pairs in length, represented by bar 'I', FIG. 15, (a)). (This can be done e.g., by a phenol-chloroform extraction followed by ultrasound treatment, mechanical shearing, by partial digestion with frequent cutter restriction endonucleases or other methods known by those skilled in the art). In order to standardise experimental conditions, the extracted and cut DNA fragments can be size-fractionated, e.g., by agarose gel electrophoresis, sucrose gradient centrifugation or gel chromatography. Fragments obtained within a single fraction can be used in providing templates in order to reduce the variability in size of the templates.

Secondly, the extracted, cut and (optionally) sorted template DNA fragments can be ligated with oligonucleotide linkers (IIa and IIb, FIG. 15, (a)) containing the sequence of the primer(s) which have previously been grafted onto a support. This can be achieved, for instance, using "blunt-end" ligation. Alternatively, the template DNA fragments can be inserted into a biological vector at a site that is flanked by the sequence of the primers that are grafted on the support. This cloned DNA can be amplified within a biological host and extracted. Obviously, if one is working with a single primer grafted to the solid support for DNA colony formation, purifying fragments containing both P1 and P2 primers does not pose a problem.

Hereafter, the DNA fragments obtained after such a suitable process are designated by the expression: "prepared genomic DNA" (III, FIG. 15, (a)).

(ii) Preparation of Random DNA Fragments Originating from a Plurality of Samples Here it is described how to prepare DNA originating from a plurality of biological samples in the case where it is necessary to keep track of the origin of the DNA when it is incorporated within a colony.

The procedure is the same as that described in the previous section except that in this case, the oligonucleotide linkers used to tail the randomly cut genomic DNA fragments are now made of two parts; the sequence of the primers grafted onto the surface (P1 and P2, FIG. 15, (b)) and a "tag" sequence which is different for each sample and which will be used for identifying the origin of the DNA colony. Note that for each sample, the tag may not be unique, but a plurality of tags could be used. Hereafter, we will designate the DNA fragments obtained after such a suitable process by the expression "tagged genomic DNA" (III, FIG. 15, (b)).

This tagging procedure can be used for providing colonies carrying a means of identification which is independent from the sequence carried by the template itself. This could also be useful when some colonies are to be recovered specifically (using the procedure given in section D). This could also be useful in the case the recovered colonies are further processed, e.g., by creating new primary colonies and a cross reference between the original colonies and the new colonies is desired.

(iii) Preparation of DNA Fragments Corresponding to a Plurality of DNA Sequences Originating from One Sample The DNA of interest can first be extracted from a biological sample by any means known by those skilled in the art (as mentioned supra). Then the specific sequences of interest can be amplified with PCR (step (i), FIG. 15 (c)) using PCR primers (IIa and IIb) made of two parts; 1) at the 5'-end, the sequences corresponding to the sequences of primer oligonucleotide(s) that have been grafted onto a surface (P1 and P2) and 2) at the 3'-end, primer sequences specific to the sequence of interest (S1 and S2). Hereafter, we will designate the DNA fragments obtained after such a suitable process by the expression: "prepared DNA" (111, FIG. 15 (c)).

(iv) Preparation of a Plurality of DNA Fragments Originating from a Plurality of Samples The procedure is the same as in the previous section except that in this case the DNA primers (IIa and IM) used to perform the PCR amplification (step (i), FIG. 13, (D)) are now made of three parts; 1) the sequence of the primers grafted onto the surface (P1 and P2), 2) a "tag" sequence which is different for each sample and which will be used for the identifying the origin of the DNA colony and 3) primer sequences surrounding the specific sequence of interest (S1 and S2). Note that for each sample, a plurality of tags might be used, as in (ii) supra.

Hereafter, we will designate the DNA fragments obtained after such a suitable process by the expression: "tagged DNA" (III, FIG. 13, (d)). Potential uses of tags are the same as in (ii), supra.

(v) Preparation of mRNA

The procedure is similar to the procedures described for preparing DNA fragments in the previous sections except that the starting point is to extract mRNA by any means known to those skilled in the art (e.g., by use of commercially available mRNA preparation kits). The mRNA can be copied into double-stranded cDNA by any means known to those skilled in the art (e.g. by using a reverse transcriptase and a DNA polymerase). Certainly, the tags and primers described supra can be used in conjunction with the process of double-stranded cDNA synthesis to allow their incorporation into the templates. Hereafter, we will designate the mRNA fragments obtained after such suitable processes by the expressions: "prepared total mRNA" (cf. "prepared genomic DNA", as described in section (I) supra), "tagged total mRNA", (cf. "tagged genomic DNA", as described in section (ii) supra), "prepared mRNA" (cf. "prepared DNA", as described in section (iii) supra) and "tagged mRNA" (cf. "tagged DNA", as described in section (iv) supra).

H) Preferred Detection Assays

In assay procedures of the present invention labels may be used to provide detectable signals. Examples include:
a) a fluorescent group or a energy-transfer based fluorescence system.
b) a biotin based system. In this case colonies can be incubated with streptavidin labelled with a fluorescent group or an enzyme (e.g. fluorescent latex beads coated with streptavidin; streptavidin labelled with fluorescent groups; enzymes for use with the corresponding fluorescence assay).
c) a system based on detecting an antigen or a fragment thereof—e.g. a hapten (including biotin and fluorescent groups). In this case colonies can be incubated with antibodies (e.g. specific for a hapten). The antibodies can be labelled with a fluorescent group or with an enzyme (e.g. fluorescent latex beads coated with the antibody; antibodies labelled with fluorescent groups; antibodies linked to an enzyme for use with a corresponding fluorescence or luminescence assay, etc.).
d) a radio-label (e.g. incorporated by using a 5'-polynucleotide kinase and [$\gamma$-$^{32}$P]adenosine triphosphate or a DNA polymerase and [$\alpha$-$^{32}$P or $\alpha$-$^{33}$P]deoxyribonucleoside triphosphates to add a radioactive phosphate group(s) to a nucleic acid). Here colonies can be incubated with a scintillation liquid.
e) a dye or other staining agent.

Labels for use in the present invention are preferably attached
a) to nucleic acids
b) to proteins which bind specifically to double stranded DNA (e.g., histones, repressors, enhancers)
and/or
c) to proteins which bind specifically to single stranded DNA (e.g. single-stranded nucleic acid binding protein).

Labelled colonies are preferably detected by:
a) measuring fluorescence.
b) measuring luminescence.
c) measuring radioactivity
d) measuring flow or electric field induced fluorescence anisotropy.
and/or
e) measuring the polymer layer thickness.

Staining agents can be used in the present invention. Thus DNA colonies can be incubated with a suitable DNA-specific staining agent, such as the intercalating dyes, ethidium bromide, YO—YO, YO—PRO (Molecular Probes, Eugene, Oreg.).

With certain staining agents the result can be observed with a suitable fluorescence imaging apparatus.

Examples of particular assays/procedures will now be described in greater detail:
I) Preferred Embodiments of Assays of the Present Invention
(i) Nucleic Acid Probe Hybridization Assay DNA colonies are first prepared for hybridisation. Then they are hybridised with a probe (labelled or unlabelled). If required, the hybridised probed is assayed, and the result is observed. This can be done with an apparatus of the present invention (e.g. as described supra).

Preparation for Hybridisation

In a preferred embodiment of the present invention colonies are treated with a DNA restriction endonuclease which is specific either for a sequence provided by a double stranded form of one of the primers originally grafted onto the surface where colonies are formed or for another sequence present in a template DNA molecule (see e.g. FIG. 12B, (c)).

After restriction enzyme digestion, the colonies can be heated to a temperature high enough for double stranded DNA molecules to be separated. After this thermal denaturing step, the colonies can be washed to remove the non-hybridised, detached single-stranded DNA strands, leaving a remaining attached single-strand DNA.

In another embodiment the colonies can be partially digested with a double-strand_specific 3' to 5' DNA exonuclease (see section E, FIG. 12C, (f)) which removes one strand of DNA duplexes starting from the 3' end, thus leaving a part of a DNA molecule in single stranded form.

Alternatively, DNA in colonies can first be heat denatured and then partially digested with an single-strand specific 3' to 5' DNA exonuclease which digests single stranded DNA starting from the 3' end.

A further alternative is simply to heat denature DNA in the colonies.

Hybridisation of the Probe

Single-stranded nucleic acid probes (labelled or unlabelled) can be hybridised to single-stranded DNA in colonies at the appropriate temperature and buffer conditions (which depends on the sequence of each probe, and can be determined using protocols known to those skilled in the art).

Assaying of Unlabelled Hybridised Probes

A hybridised probe provided initially in unlabelled form can be used as a primer for the incorporation of the different (or a subset of the different) labelled (or a mix of labelled and unlabelled) deoxyribonucleoside triphosphates with a DNA polymerase. The incorporated labelled nucleotides can then be detected as described supra.

Cyclic Assaying of Labelled or Unlabelled Probes

Firstly, the DNA colonies can be prepared for hybridisation by the methods described supra. Then they can be hybridised with a probe (labelled or initially unlabelled). If required, hybridised labelled probes are assayed and the result is observed with an apparatus as described previously. The probe may then be removed by heat denaturing and a probe specific for a second DNA sequence may be hybridised and detected. These steps maybe repeated with new probes as many times as desired.

Secondly, the probes can be assayed as described supra for unlabelled probes, except that only a subset (preferably 1 only) of the different (labelled or unlabelled) nucleotides are used at each cycle. The colonies can then be assayed for monitoring the incorporation of the nucleotides. This second process can be repeated until a sequence of a desired length has been determined.

(ii) In situ RNA Synthesis Assay

In this embodiment, DNA colonies can be used as templates for in situ RNA synthesis as depicted in FIG. 16, (a). DNA colonies can be generated from templates and primers, such that a RNA polymerase promoter sequence is positioned at one end of the double-stranded DNA in the colony. DNA colonies can then be incubated with RNA polymerase and the newly synthesised RNA (cRNA) can be assayed as desired.

The detection can be done non-specifically (e.g., staining) or in a sequence dependent way (e.g., hybridisation).

The DNA template (I, FIG. 16, (a)) to be amplified into A colony is generated by PCR reaction using primers Ma and IIb) which have the following four parts; 1) sequence identical to the sequences of the primers grafted onto the surface ('P1' and 'P2'), 2) a "tag" sequence which is different for each sample, a sequence corresponding to a RNA polymerase promoter, i.e., the T3, T7 and SP6 RNA promoters, ('RPP', FIG. 16, (a)) and 4) primer sequences surrounding the-specific sequence of interest 'S1' and 'S2'). Hereafter, we will designate the DNA fragments obtained after such a suitable process by the expression: "tagged RNA synthesis DNA" (III, FIG. 16, (b)).

After amplification of the DNA template from the original DNA sample, these templates are used to generate DNA colonies. The DNA colonies (IV, FIG. 16, (c)) are then incubated with the RNA polymerase specific for the RNA polymerase promoter ('RPP', FIG. 16, (c)). This will generate a copy of RNA specific for the DNA colony template (Template-cRNA, V, FIG. 16, (d)).

cRNA thus synthesised can be isolated and used as hybridisation probes, as messenger RNA (mRNA) templates for in vitro protein synthesis or as templates for in situ RNA sequence analysis.

(iii) Methods for Sequencing

In another embodiment of the present invention, colonies can be analysed in order to determine sequences of nucleic acid molecules which form the colonies. Since very large numbers of the same nucleic acid molecules can be provided within each colony the reliability of the sequencing data obtained is likely to be very high.

The sequences determined may be full or partial. Sequences can be determined for nucleic acids present in one or more colonies. A plurality of sequences may be determined at the same time.

In some embodiments the sequence of a complementary strand to a nucleic acid strand to be sequenced (or of a part thereof) may be obtained initially. However this sequence can be converted using base-pairing rules to provide the desired sequence (or a part thereof). This conversion can be done via a computer or via a person. It can be done after each step of primer extension or can be done at a later stage.

Sequencing can be done by various methods. For example methods relying on sequential restriction endonuclease digestion and linker ligation can be used. One such method is disclosed in WO95/27080 for example. This method comprises the steps of: ligating a probe to an end of a polynucleotide, the probe having a nuclease recognition site; identifying one or more nucleotides at the end of the polynucleotide; and cleaving the polynucleotide with a nuclease recognising the nuclease recognition site of the probe such that the polynucleotide is shortened by one or more nucleotides.

However in a preferred method of the present invention, amplified nucleic acid molecules (preferably in the form of colonies, as disclosed herein) are sequenced by allowing primers to hybridise with the nucleic acid molecules, extending the primers and detecting the nucleotides used in primer extension. Preferably, after extending a primer by a single nucleotide, the nucleotide is detected before a further nucleotide is used in primer extension (step-by-step sequencing).

One or more of the nucleotides used in primer extension may be labelled. The use of labelled nucleotides during primer extension facilitates detection. (The term "label" is used in its broad sense to indicate any moiety that can be identified using an appropriate detection system. Preferably the label is not present in naturally-occurring nucleotides.) Ideally, labels are non-radioactive, such as fluorophores. However radioactive labels can be used.

Where nucleotides are provided in labelled form the labels may be the same for different nucleotides. If the same label is used each nucleotide incorporation can be used to provide a cumulative increase of the same signal (e.g. of a signal detected at a particular wavelength). Alternatively different labels may be used for each type of nucleotide (which may be detected at different wavelengths).

Thus four different labels may be provided for dATP, dTTP, dCTP and dGTP, or the same label may be provided for them all. Similarly, four different labels may be provided for ATP, UTP, CTP and GTP, or the same label may be provided for them all). In some embodiments of the present invention a mixture of labelled and unlabelled nucleotides may be provided, as will be described in greater detail later on.

In a preferred embodiment of the present invention the sequencing of nucleic acid molecules present in at least 2 different colonies is performed simultaneously. More preferably, sequencing of nucleic acid molecules present in over 10, over 100, over 1000 or even over 1,000,000 different colonies is performed simultaneously. Thus if colonies having different nucleic acids molecules are provided, many different sequences (full or partial) can be determined simultaneously—i.e. over 10, over 100, over 1000 or even over 1,000,000 different sequences may be determined simultaneously.

If desired, controls may be provided, whereby a plurality of colonies comprising the same nucleic acid molecules are provided. By determining whether or not the same sequences are obtained for nucleic acid molecules in these colonies it can be ascertained whether or not the sequencing procedure is reliable.

One sequencing method of the present invention is illustrated in FIG. 17, which is entitled "in situ sequencing". On prepared DNA colonies hybridised with an appropriate sequencing primer, cyclic addition of the individual deoxyribonucleoside triphosphates and DNA polymerase will allow the determination of the DNA sequence immediately 3' to the sequencing primer. In the example outlined in FIG. 17, the addition of dGTP allows the determination of colony 1 to contain a 'G'. In the second cycle addition of DATP is detected in both colonies, determining that both colonies have an 'A' in the next position. After several repetitions of the addition of single deoxyribonucleoside triphosphates, it will be possible to determine any sequence. For example sequences of at least 10, at least 20, at least 50 or at least 100 bases may be determined.

If colonies are provided initially in a form comprising double-stranded molecules the colonies can be processed to provide single-stranded molecules for use in sequencing as described above. (It should however be noted that double stranded molecules can be used for sequencing without such processing. For example a double stranded DNA molecule can be provided with a promoter sequence and step-by-step sequencing can then be performed using an RNA polymerase and labeled ribonucleotides (cf FIG. 16, (d))). Another alternative is for a nick to be introduced in a double stranded DNA molecule so that nick translation can be performed using labeled deoxyribonucleotides. and a DNA polymerase with 5' to 3' exonuclease activity.)

One way of processing double-stranded molecules present in colonies to provide single-stranded colonies as described later with reference to FIG. 18. Here double-stranded immobilised molecules present in a colony (which may be in the form of bridge-like structures) are cleaved and this is followed by a denaturing step. (Alternatively a denaturing step could be used initially and could be followed by a cleavage step). Preferably cleavage is carried out enzymatically. However other means of cleavage are possible, such as chemical cleavage. (An appropriate cleavage site can be provided in said molecule.) Denaturing can be performed by any suitable means. For example it may be performed by heating and/or by changing the ionic strength of a medium in the vicinity of the nucleic acid molecules.

Once single-stranded molecules to be sequenced are provided, suitable primers for primer extension can be hybridised thereto. Oligonucleotides are preferred as primers. These are nucleic acid molecules that are typically 6 to 60, e.g. 15 to 25 nucleotides long. They may comprise naturally and/or non-naturally occurring nucleotides. (However other molecules, e.g. longer nucleic acid strands may alternatively be used as primers, if desired.) The primers for use in sequencing preferably hybridise to the same sequences present in amplified nucleic acid molecules as do primers that were used to provide said amplified nucleic acids. (Primers having the same/similar sequences can be used for both amplification and sequencing purposes).

When primers are provided in solution and are annealed (hybridised) to nucleic acid molecules present in colonies to be sequenced, those primers which remain in solution or which do not anneal specifically can be removed after annealing. Preferred annealing conditions (temperature and buffer composition) prevent non-specific hybridisation. These may be stringent conditions. Such conditions would typically be annealing temperatures close to a primer's Tm (melting temperature) at a given salt concentration (e.g. 50 nM primer in 200 mM NaCl buffer at 55° C. for a 20-mer oligonucleotide with 50% GC content). (Stringent conditions for a given system can be determined by a skilled person. They will depend on the base composition, GC content, the length of the primer used and the salt concentration. For a 20 base oligonucleotide of 50% GC, calculated average annealing temperature is 55-60° C., but in practice may vary between 35 to 70° C.).

Primers used for primer extension need not be provided in solution, since they can be provided in immobilised form. In this embodiment the primers should be provided in the vicinity of the immobilised molecules to which they are to be annealed. (Such primers may indeed already be present as excess immobilised primers that were not used in amplifying nucleic acid molecules during the formation of colonies.)

The nucleic acid molecules present in colonies to be sequenced will include a sequence that hybridises to the primers to be used in sequencing (preferably under "stringent" conditions). This portion can be added to a given molecule prior to amplification (which molecule may have a totally/partially unknown sequence) using techniques known to those skilled in the art. For example it can be synthesised artificially and can be added to a given molecule using a ligase.

Once a nucleic acid molecule annealed to a primer is provided, primer extension can be performed. RNA or DNA polymerases can be used. DNA polymerases are however the enzymes of choice for preferred embodiments. Several of these are commercially available. Polymerases which lack 3' to 5' exonuclease activity can be used, such as T7 DNA polymerase or the small (Klenow) fragment of DNA polymerase I may be used [e.g. the modified T7 DNA polymerase Sequenase™ 2.0 (Amersham) or Klenow fragment (3' to 5' exo-, New England Biolabs)]. However it is not essential to use such polymerases. Indeed, where it is desired that the polymerases have proof-reading activity polymerases lacking 3' to 5' exonuclease activity would not be used. Certain applications may require the use of thermostable polymerases such as ThermoSequenase™ (Amersham) or Taquenase™ (ScienTech, St Louis, Mo.). Any nucleotides may be used for primer extension reactions (whether naturally occurring or non-naturally occurring). Preferred nucleotides are deoxyribonucleotides; dATP, dTTP, dGTP and dCTP (although for some applications the dTTP analogue dUTP is preferred) or ribonucleotides ATP, UTP, GTP and CTP; at least some of which are provided in labelled form.

A washing step is preferably incorporated after each primer extension step in order to remove unincorporated nucleotides that may interfere with subsequent steps. The preferred washing solution should be compatible with polymerase activity and have a salt concentration that does not interfere with the annealing of primer molecules to the nucleic acid molecules to be sequenced. (In less preferred embodiments, the washing solution may interfere with polymerase activity. Here the washing solution would need to be removed before further primer extension.)

Considering that many copies of molecules to be sequenced can be provided in a given colony, a combination of labelled and non-labelled nucleotides can be used. In this case, even if a small proportion of the nucleotides are labelled (e.g. fluorescence-labelled), the number of labels incorporated in each colony during primer extension can be sufficient to be detected by a detection device. For example the ratio of labelled to non-labelled nucleotides may be chosen so that, on average, labelled nucleotides are used in primer extension less than 50%, less than 20%, less than 10% or even less than 1% of the time (i.e. on average in a given primer extension step a nucleotide is incorporated in labelled form in less than 50%, less than 20%, less than 10%, or less than 1% of the extended primers.)

Thus in a further embodiment of the present invention there is provided a method for sequencing nucleic acid molecules present in a colony of the present invention, the method comprising the steps of:

a) providing at least one colony comprising a plurality of single stranded nucleic acid molecules that have the same sequences as one another and that are hybridised to primers in a manner to allow primer extension in the presence of nucleotides and a nucleic acid polymerase;

b) providing said at least one colony with a nucleic acid polymerase and a given nucleotide in labelled and unlabelled form under conditions that allow extension of the primers if a complementary base or if a plurality of such bases is present at the appropriate position in the single stranded nucleic acid molecules present in said at least one colony;

c) detecting whether or not said labelled nucleotide has been used for primer extension by determining whether or not the label present on said nucleotide has been incorporated into extended primers;

Steps b) and c) may be repeated one or more times. Preferably a plurality of different colonies are provided and several different sequences are determined simultaneously.

This further embodiment of the present invention can be used to reduce costs, since relatively few labelled nucleotides are needed. It can also be used to reduce quenching effects.

It is however also possible to use only labelled nucleotides for primer extension or to use a major portion thereof (eg. over 50%, over 70% or over 90% of the nucleotides used may be labelled). This can be done for example if labels are selected so as to prevent or reduce quenching effects. Alternatively labels may be removed or neutralised at various stages should quenching effects become problematic (e.g. laser bleaching of fluorophores may be performed). However this can increase the number of steps required and it is therefore preferred that labels are not removed (or at least that they are not removed after each nucleotide has been incorporated but are only removed periodically). In other less preferred embodiments, the primer itself and its extension product may be removed and replaced with another primer. If required, several steps of sequential label-free nucleotide additions may be performed before actual sequencing in the presence of labelled nucleotides is resumed. A further alternative is to use a different type of label from that used initially (e.g. by switching from fluorescein to rhodamine) should quenching effects become problematic.

In preferred embodiments of the present invention a plurality of labelled bases are incorporated into an extended primer during sequencing. This is advantageous in that it can speed up the sequencing procedure relative to methods in which, once a labelled base has been incorporated into an extended primer, the label must be removed before a further labelled base can be incorporated. (The plurality of labelled bases may be in the form of one or more contiguous stretches, although this is not essential.)

The present invention therefore also includes within its scope a method for sequencing nucleic acid molecules, comprising the steps of:
a) using a first colony to provide a plurality of single stranded nucleic acid molecules that have the same sequences as one another and that are hybridised to primers in a manner to allow primer extension in the presence of nucleotides and a nucleic acid polymerase;
b) using a second colony to provide a plurality of single stranded nucleic acid molecules that have the same sequences as one another, and that are also hybridised to primers in a manner to allow primer extension in the presence of nucleotides and a nucleic acid polymerase;
c) providing each colony with a nucleic acid polymerase and a given labelled nucleotide under conditions that allow extension of the primers if a complementary base or if a plurality of such bases is present at the appropriate position in the single stranded nucleic acid molecules;
d) detecting whether or not said labelled nucleotide has been used for primer extension at each colony by determining whether or not the label present on said nucleotide has been incorporated into extended primers;
e) repeating steps c) and d) one or more times so that extended primers comprising a plurality of labels are provided.

Preferably the sequences of the nucleic acid molecules present at said first and said locations are different from one another—i.e. a plurality of colonies comprising different nucleic acid molecules are sequenced In view of the foregoing description it will be appreciated that a large number of different sequencing methods using colonies of the present invention can be used. Various detection systems can be used to detect labels used in sequencing in these methods (although in certain embodiments detection may be possible simply by eye, so that no detection system is needed). A preferred detection system for fluorescent labels is a Charge-Coupled-Device (CCD) camera, which can optionally be coupled to a magnifying device. Any other device allowing detection and, preferably, also quantification of fluorescence on a surface may be used. Devices such as fluorescent imagers or confocal microscopes may be chosen.

In less preferred embodiments, the labels may be radioactive and a radioactivity detection device would then be required. Ideally such devices would be real-time radioactivity imaging systems. Also less preferred are other devices relying on phosphor screens (Molecular Dynamics) or autoradiography films for detection.

Depending on the number of colonies to be monitored, a scanning system may be preferred for data collection. (Although an alternative is to provide a plurality of detectors to enable all colonies to be covered.) Such a system allows a detector to move relative to a plurality of colonies to be analysed. This is useful when all the colonies providing signals are not within the field of view of a detector. The detector may be maintained in a fixed position and colonies to be analysed may be moved into the field of view of the detector (e.g. by means of a movable platform). Alternatively the colonies may be maintained in fixed position and the detection device may be moved to bring them into its field of view.

The detection system is preferably used in combination with an analysis system in order to determine the number (and preferably also the nature) of bases incorporated by primer extension at each colony after each step. This analysis may be performed immediately after each step or later on, using recorded data. The sequence of nucleic acid molecules present within a given colony can then be deduced from the number and type of nucleotides added after each step.

Preferably the detection system is part of an apparatus comprising other components. The present invention includes an apparatus comprising a plurality of labelled nucleotides, a nucleic acid polymerase and detection means for detecting labelled nucleotides when incorporated into a nucleic acid molecule by primer extension, the detection means being adapted to distinguish between signals provided by labelled nucleotides incorporated at different colonies.

The apparatus may also include temperature control, solvent delivery and washing means. It may be automated.

Methods and apparatuses within the scope of the present invention can be used in the sequencing of:
unidentified nucleic acid molecules (i.e. de novo sequencing);
and nucleic acid molecules which are to be sequenced to check if one or more differences relative to a known sequence are present (e.g. identification of polymorphisms). This is sometimes referred to as "re-sequencing".

Both de novo sequencing and re-sequencing are discussed in greater detail later on (see the following sections (v) and (vi)).

For de novo sequencing applications, the order of nucleotides applied to a given location can be chosen as desired. For example one may choose the sequential addition of nucleotides dATP, dTTP, dGTP, dCTP; dATP, dTTP, dGTP, dCTP; and so on. (Generally a single order of four nucleotides would be repeated, although this is not essential.) For re-sequencing applications, the order of nucleotides to be added at each step is preferably chosen according to a known sequence.

Re-sequencing may be of particular interest for the analysis of a large number of similar template molecules in order to detect and identify sequence differences (e.g. for the analysis of recombinant plasmids in candidate clones after site directed mutagenesis or more importantly, for polymorphism screening in a population). Differences from a given sequence can be detected by the lack of incorporation of one or more nucleotides present in the given sequence at particular stages of primer extension. In contrast to most commonly used techniques, the present method allows for detection of any type of mutation such as point mutations, insertions or deletions. Furthermore, not only known existing mutations, but also previously unidentified mutations can be characterised by the provision of sequence information.

In some embodiments of the present invention long nucleic acid molecules may have to be sequenced by several sequencing reactions, each one allowing for determination of part of the complete sequence. These reactions may be carried out at different colonies (where the different colonies are each provided with the same nucleic acid molecules to be sequenced but different primers), or in successive cycles applied at the same colony (where between each cycles the primers and extension products are washed off and replaced by different primers).

(iv) DNA Fingerprinting

This embodiment of the present invention aims to solve the problem of screening a large population for the identification of given features of given genes, such as the detection of single nucleotide polymorphisms.

In one preferred embodiment, it consists in generating tagged genomic DNA (see section G(ii) supra). (Thus each sample originating from a given individual sample has been labelled with a unique tag). This tagged DNA can be used for generating primary colonies on an appropriate surface comprising immobilised primers. Several successive probe hybridisation assays to the colonies can then be performed. Between each assay the preceding probe can be removed, e.g. by thermal denaturation and washing.

Advantages of this embodiment of the present invention over other approaches for solving this problem are illustrated in the following example of a potential practical application.

It is intended to detect which part of a gene (of, e.g., 2000 bases in size), if any, is related to a disease phenotype in a population of typically 1,000 to 10,000 individuals. For each individual, a PCR amplification can be performed to specifically amplify the gene of interest and to link a tag and a colony generating primer (refer to section G(iv), preparation of "tagged DNA").

In order to obtain a representative array of sample, one might want to array randomly 500,000 colonies (i.e. 10 times redundancy, so to have only a small probability of missing the detection of a sample) With a colony density of 10,000 colonies per mm$^2$, a surface of ~7 mm×7 mm can be used. This is a much smaller surface than any other technology available at present time (e.g. The HySeq approach uses 220 mm×220 mm for the same number of samples (50,000) without redundancy). The amount of reactants (a great part of the cost) will be proportional to the surface occupied by of the array of samples. Thus the present invention can provide an 800 fold improvement over the presently available technology.

Using an apparatus to monitor the result of the 'in situ' sequencing or probe hybridisation assays, it should take on the order of 1 to 10 seconds to image a fluorescent signal from colonies assayed using fluorescence present on a surface of ~1 mm$^2$. Thus, assuming that the bottleneck of the method is the time required to image the result of the assay, it takes of the order of 10 minutes to image the result of an assay on 50,000 samples (500,000 colonies). To provide 200 assays including imaging (on one or several 7 mm×7 mm surfaces), using the present invention can take less than 36 hours. This represents a 20 times improvement compared to the best method known at present time (HySeq claims 30 days to achieve a comparable task).

Improvements (colony densities 10 times higher and imaging time of 1 second) could allow for much higher throughput and finally the ultimately expected throughput could be about 2000 times faster than the best, not yet fully demonstrated, technology available at present time.

Another advantage of using the present invention lies in the fact that it overcomes the problem arising with individuals who have heterozygous mutations for a given gene. While this problem may be addressed by existing sequencing methods to determine allelic polymorphisms, current high throughput mutation detection methods based on oligonucleotide probe hybridisation may lead to difficulties in the interpretation of results due to an unequal hybridisation of probes in cases of allelic polymorphisms and therefore errors can occur. In this embodiment of the present invention, each colony arises from a single copy of an amplified gene of interest. If an average of 10 colonies are generated for each individual locus, there will be an average of 5 colonies corresponding to one version of a gene and 5 colonies corresponding to the other version of the gene. Thus heterozygotic mutations can be scored by the number of times a single allele is detected per individual genome sample.

(v) DNA Resequencing

This embodiment of the present invention provides a solution to the problem of identifying and characterising novel allelic polymorphisms within known genes in a large population of biological samples.

In its preferred embodiment it consists in obtaining tagged DNA (each sample originating from a given individual has been tagged with a unique tag—see section G(iv)). This encoded DNA can then be used for generating primary colonies on an appropriate surface comprising immobilised primers. Several successive assays of probe hybridisation to the colonies can then be performed wherein between each cyclic assay the preceding probe can be removed by thermal denaturation and washing. Preferably, the DNA sequence 3' to a specific probe may be determined directly by 'in situ sequencing' (section I(iii), Methods of sequencing).

The advantages of the present invention over other approaches for solving this problem are illustrated in the following example of potential practical application:

It is desired to identify the variability of the sequence of a gene (of, e.g., 2 000 bases in size), if any, in a population of typically 4 000 individuals. It is assumed that a reference sequence of the gene is known. For each individual, a PCR amplification can be performed to specifically amplify the gene of interest and link a tag and a colony generating primer. In order to obtain a representative array of sample, one might want to array randomly 40 000 colonies (i.e. 10 times redundancy, so to have a small probability of missing the detection of a sample). With a colony density of 10 000 colonies per mm$^2$, a surface of ~2 mm×2 mm can be used.

Using an apparatus with a CCD camera (having a 2000× 2000 pixel chip) to monitor the result of the assay, it should take of the order of 10 seconds to image a fluorescent signal from colonies on a surface of 4 mm$^2$. If it is assumed possible to read at least 20 bases during one round of the assay, this requires 61 imaging steps (3n+1 imaging steps are necessary for reading n numbers of bases). If it is assumed that the bottleneck of the method is the time to image the result of the assay, it takes of the order of 15 minutes to image the result of an assay on 4 000 samples (40 000 colonies). To realise 100 assays (on one or several 2×2 mm$^2$ surfaces) in order to cover the entire gene of interest, the present invention can allow the whole screening experiment to be performed in approximately one day, with one apparatus. This can be compared to the most powerful systems operational at the present time.

In this embodiment of the present invention with conservative assumptions (colony density, imaging time, size of the CCD chip), a throughput of $3.2 \times 10^6$ bases per hour could be reached, i.e. a 400 fold improvement when compared to the most commonly used system at present time (current DNA sequencers have a typical throughput of the order of 8,000 bases read/hour).

(vi) de novo DNA Sequencing

This embodiment of the present invention aims to solve the problem of sequencing novel genomes (or parts thereof) with low cost and in short time, where the sequence of the DNA is not known. Genomic DNA can be prepared, either directly from the total DNA of an organism of interest or from a vector into which DNA has been inserted. The prepared genomic DNA (from whatever source) can be used to generate DNA colonies. The DNA colonies can then be digested with a rare-cutting restriction enzyme, whose site is included in the linker, denatured and sequenced.

FIG. 18 depicts an example of de novo DNA sequencing. In this example, genomic DNA is fragmented into pieces of 100 to 2000 base pairs (see preparation of random DNA fragments, section G(i)). These fragments will be ligated to oligonucleotide linkers (IIa and IIb, FIG. 18, (a)) which include sequences specific for the grafted primers on the surface ('P1' and 'P2'), a sequence which is recognised by a rare-cutting restriction nuclease ('RE') and a sequence corresponding to a sequencing primer ('SP'), resulting in templates (III, FIG. 18, (b)). Using this prepared DNA as template for DNA colony formation, one obtains primary colonies (IV, FIG. 18, (c)). These colonies are then digested with the corresponding restriction endonuclease and denatured to remove the non-attached DNA strand (V, FIG. 18, (d)). The sequencing primer (SP) is then annealed to the attached single-stranded template (FIG. 18, (e)). Incorporation and detection of labeled nucleotides can then be carried out as previously described (see section I(iii), Methods of Sequencing).

In this embodiment, the throughput obtainable can be at least 400 times higher than presently available methods.

(vii) mRNA Gene Expression Monitoring

This embodiment of our invention means to solve the problem of monitoring the expression of a large number of genes simultaneously.

Its preferred embodiment is depicted in FIG. 19.

Firstly, primary colonies are prepared, as depicted in FIG. 3. in its preferred form, the DNA used for this preparation is 'prepared genomic DNA' or 'tagged genomic DNA', as described in section G(i) and G(iii), respectively, and where the DNA is either from the whole genome of one (or several) organism(s) or from a subset thereof (e.g., from a library of previously isolated genes). In FIG. 19, the uppercase letters, "A", "B" and "D" represent colonies which have arisen from genes which exhibit high, medium and low expression levels, respectively, and "E" represents colonies arising from non-expressed genes (in real cases, all these situations may not necessarily be present simultaneously).

Secondly, the colonies are treated to turn then into supports (i.e. secondary primers) for secondary colony growing (step i in FIG. 19, (a)), as described in section E. At this stage (FIG. 19, (a)), the treated colonies are represented by underlined characters (A, B, D, or E) .

Thirdly, (step ii in FIG. 19, (b)) this support for secondary colony growing is used to regenerate colonies from mRNA (or cDNA) templates extracted from a biological sample, as described in section C. If the template is mRNA, the priming step of colony regeneration will be performed with a reverse transcriptase. After a given number of colony amplification cycles, preferably 1 to 50, the situation will be as depicted in (FIG. 19, (c)): the colonies corresponding to highly expressed genes (represented by the letter "A") are totally regenerated, as their regeneration has been initiated by many copies of the mRNA; the colonies corresponding to genes of medium expression levels (represented by the letters "b" and "B"), have been only partially regenerated; only a few of the colonies corresponding to rare genes (represented by the letter "d"), have been partially regenerated; the colonies corresponding to non-expressed sequences (represented by the letter "E"), have not been regenerated at all.

Lastly, (step iii in FIG. 19, (c)), additional cycles of colony growing are performed (preferably 2 to 50), and the colonies which have not been totally regenerated during the previous steps finally become totally regenerated, "b" becomes "B", "d" becomes "D" (FIG. 19, (d)) the colonies corresponding to genes with high and medium expression levels are all regenerated "A" and "B" or "B"; the colonies corresponding to genes with low levels of expression are not all regenerated "D" and "D"; the colonies corresponding to non-expressed sequences are not regenerated at all "E".

The relative levels of expression-of the genes can be obtained by the following preferred methods:

Firstly levels of expression can be monitored by following the rate of regeneration of the colonies (i.e., by measuring the amount of DNA inside a colony after different number of colony growing cycles during step (iii)) as the rate at which a colony is regenerated will be linked the number of mRNA (or cDNA) molecules which initiated the regeneration of that colony (at first approximation, the number of DNA molecules after n cycles, noted M(n), in a colony undergoing regeneration should be given by $M(n)=M_0 r^{(n-1)}$, where $M_0$ is the number of molecules which initiated the regeneration of the colony, r is the growing rate and n is the number of cycles);

Secondly, levels of expression can be monitored by counting, for each gene, the number of colonies which have been regenerated and comparing this number to the total number of colonies corresponding to that gene. These measurements will generally give access to the relative expression levels of the genes represented by the colonies. The identification of the colonies is preferably performed by fingerprinting, in a manner essentially similar to embodiment, section I(iv). Note that encoding the DNA samples is not required, but can be considered as an alternative to the direct identification of the DNA in the colonies. This can be of practical interest because with coding, the same codes (thus the same oligonucleotides involved in assaying the code) can be used for any set of genes, whereas without code, a different set of specific oligonucleotides has to be used for each set of genes.

This embodiment of our invention has many advantages if compared to current state of the art including: a very high throughput; no requirement for prior amplification of the mRNA (even though prior amplification is compatible with or invention); small amounts of samples and reactants are required due to the high density of samples with our invention; the presence of highly expressed genes has no incidence on the ability to monitor genes with low levels of expression; the ability to simultaneously monitor low and high levels of expression within the set of genes of interest.

When the initial DNA in the generation of the primary DNA colony is made from the DNA of a whole genome, this embodiment also provides the following features: there is no interference between genes expressed at high level and at low level even though one has not performed specific amplification of the genes of interest. This is a unique feature of the use of this invention: specific amplification is not possible because the initial assumption of this embodiment is to monitor the expression genes which may have not yet been isolated, thus which are unknown, and thus for which no specific (unique) sequences are known and which specific sequences would have been necessary for specific gene amplification. The ability of our invention to perform this type of mRNA expression monitoring is due to the fact that when the primary colonies are prepared, statistically, each piece of the initial genome will be represented by the same number of colonies.

Thus, frequent and rare DNA will initiate the same number of colonies (e.g., one colony per added genome molecule). Quantitative information might be obtained both from frequent and rare mRNAs by monitoring the growing rate of the colonies.

(viii) Isolation and Characterisation of Novel Expressed Genes

This embodiment of our invention means to solve the problem of isolating the genes which are specifically induced under given conditions, e.g., in specific tissues, different strains of a given species or under specific activation. A practical example is the identification of genes which are up or down regulated after drug administration.

The preferred embodiment for isolating genes from a specific or activated biological sample (hereafter called target sample) which are up-regulated compared with a reference biological~sample (hereafter called reference sample) is depicted in FIG. 20.

Firstly, primary colonies are prepared (FIG. 20, (a)). In its preferred form, the DNA used for this preparation is prepared genomic DNA or tagged genomic DNA, as described in sections G(i) and G(ii), respectively, where the DNA is either from the whole genome of one (or several) organism(s) or from a subset thereof (e.g., from a library of previously isolated genes), and where both the primers used for colony generation (hereafter called P1 and P2) contain a endonuclease restriction site. In FIG. 20, (a), "A" represents colonies which have arisen from genes expressed in both the reference sample and the target sample, "B" represents colonies which have arisen from genes expressed only in the reference sample, "C" represents colonies which have arisen from genes expressed only in the target sample, and "D" represents colonies arising from non-expressed genes (in real cases, all these situations may not necessarily be present simultaneously).

Secondly, primary colonies are then treated to generate secondary primers as the support for secondary colony growing (step i in FIG. 20, (a)). At this stage (b), the colonies are represented as underlined characters (A,B,C,D).

Thirdly, (step ii in FIG. 20, (b)) the secondary primers are used to regenerate colonies using mRNA or cDNA (represented by "mA+mB") extracted from the biological reference sample as a template, as described in G(v). If the template is mRNA, the first elongation step of colony regeneration will be performed with a reverse transcriptase. After enough colony growing cycles, preferably 5 to 100, only the colonies corresponding to genes expressed in the reference sample ("A" and "B") will be regenerated, as depicted in (FIG. 20, (c)).

In step (iii), the colonies are digested with a restriction enzyme (represented by RE) which recognises a site in the flanking primer sequences, P1 and P2, which are grafted on the support and which were the basis of primary colony generation. Importantly, only the colonies which have been regenerated during step (ii) will be digested. This is because the support for secondary colony growth is made of single stranded DNA molecules, which can not be digested by the restriction enzyme. Only the regenerated colonies are present in a double stranded form, and are digested. After digestion, the situation is the one depicted in FIG. 20, (d). The colonies corresponding to the genes expressed in the reference sample have totally disappeared, i.e., they are not even present as a support for secondary colony growth, and the colonies corresponding to genes expressed only in the target sample "C" and the colonies corresponding to non-expressed genes "D" are still present as a support for secondary colony generation.

In step (iv), mRNA (or cDNA) (represented by "mA+mC") extracted from the target sample is used to generate secondary colonies. Because colonies corresponding to mA and mB no longer exist, only the colonies corresponding to mC can be regenerated (i.e., only the mRNA specifically expressed in the target sample). After sufficient number of colony growing cycles (preferably 5 to 100), the situation is such that only the colonies corresponding to genes expressed specifically in the target sample are regenerated ("C", FIG. 20, (e)).

In step (v), the regenerated colonies "C" are used to generate copies of the DNA that they contain by performing several (preferably 1 to 20) colony growing cycles in the presence of the primers P1 and P2, as described in section D of the present invention. A PCR amiplification is then performed using P1 and P2 in solution (described in section D) and the amplified DNA characterised by classical methods.

The preferred embodiment for isolating genes from a specific or activated biological sample which are less expressed than in a reference biological sample is depicted in FIG. 21. The different steps involved in this procedure are very similar to those involved in the isolation of gene which are more regulated than in the reference sample, and the notation are the same as in FIG. 20. The only difference is to inverse the order used to regenerate the colonies: in step (ii), the mRNA used is the one extracted from the target biological sample ("mA+mC") instead of the mRNA extracted form the reference biological sample ("mA+mB"), and in step (iv), the mRNA used is the one extracted from the reference biological sample ("mA+mB") instead of the one extracted from the target sample ("mA+mC"). As a result, only the DNA from colonies corresponding to genes which are expressed in the reference sample but not in the target sample is recovered and amplified ("B", FIG. 21, (f)).

The invention claimed is:

1. A method for producing an array of single stranded nucleic acid templates comprising the steps of:
   A) providing a population of different nucleic acid fragments comprising a target region of unknown sequence, attaching a nucleic acid sequence to each end of each of the different nucleic acid fragments, and producing a collection of different fragments wherein each of the collection of different fragments comprises an identical universal first end and an identical universal second end;
   B) providing immobilized primers comprising at least two different sequences, each sequence of the at least two different sequences comprising a region complementary to the identical universal first end or the identical universal second end of the fragments;
   C) adding the collection of different fragments to the immobilized primers to allow the different fragments to anneal to the immobilized primers;
   D) amplifying the collection of different fragments and producing an array of amplified double stranded templates comprising the target region of unknown sequence; and
   E) cleaving just one strand of each of the amplified double stranded templates on the array to remove the one strand of each of the amplified double stranded templates from the array and to retain other strand of each of the amplified double stranded templates on the array wherein the another strand of each of the amplified double stranded templates comprises the target region of unknown sequence, thereby producing an array of single stranded nucleic acid templates.

2. The method according to claim 1, wherein the immobilized primers consist of $2^n$ different types of primers, wherein n is an integer equal to or more than 2.

3. The method according to claim 1, wherein the immobilized primers are present in about the same concentration.

4. The method according to claim 1, wherein the amplifying the collection of different fragments is carried out in the presence of a supply of nucleotides and a nucleic acid polymerase.

5. The method according to claim 1, wherein the nucleotides contain one or more detectable labels and the one or more detectable labels is/are incorporated into the amplified double stranded templates.

6. The method according to claim 1, wherein the amplifying the collection of different fragments is repeated cycles of nucleic acid amplification and is performed automatically.

7. The method of claim 5 in which the labels are fluorescent labels or radiolabels.

8. The method according to claim 1, wherein said cleaving just one strand of each of the amplified double stranded templates on the array is carried out with a ribozyme, wherein the amplified double stranded templates comprise RNA sequences and step D) is performed in the presence of a RNA polymerase and ribonucleotides.

* * * * *

UNITED STATES PATENT AND TRADEMARK OFFICE
CERTIFICATE OF CORRECTION

| | | |
|---|---|---|
| PATENT NO. | : 7,985,565 B2 | Page 1 of 1 |
| APPLICATION NO. | : 10/449010 | |
| DATED | : July 26, 2011 | |
| INVENTOR(S) | : Pascal Mayer et al. | |

It is certified that error appears in the above-identified patent and that said Letters Patent is hereby corrected as shown below:

Title Page item 57 in Abstract, at Column 2, Line 7, delete "provided" and insert -- provide --, therefor.

In claim 1, at Column 43, Line 28, delete "another" and insert -- other --, therefor.

Signed and Sealed this
Twenty-eighth Day of February, 2012

David J. Kappos
*Director of the United States Patent and Trademark Office*